United States Patent
Kralicek et al.

(10) Patent No.: US 12,044,651 B2
(45) Date of Patent: Jul. 23, 2024

(54) SENSOR DEVICE AND METHODS

(71) Applicant: SCENTIAN BIO LIMITED, Auckland (NZ)

(72) Inventors: Andrew Vladimir Kralicek, Auckland (NZ); Colm Carraher, Auckland (NZ); Han Yue Zheng, Lower Hutt (NZ); Natalie Olivia Victoria Plank, Wellington (NZ); Jadranka Travas-Sejdic, Auckland (NZ); Nihan Aydemir, Auckland (NZ); Thanihaichelvan Murugathas, Jaffna (LK); Roshan Khadka, Auckland (NZ)

(73) Assignee: SCENTIAN BIO LIMITED, Auckland (NZ)

( * ) Notice: Subject to any disclaimer, the term of this patent is extended or adjusted under 35 U.S.C. 154(b) by 1046 days.

(21) Appl. No.: 16/471,552

(22) PCT Filed: Dec. 20, 2017

(86) PCT No.: PCT/IB2017/058181
§ 371 (c)(1),
(2) Date: Jun. 19, 2019

(87) PCT Pub. No.: WO2018/116186
PCT Pub. Date: Jun. 28, 2018

(65) Prior Publication Data
US 2019/0346401 A1    Nov. 14, 2019

(30) Foreign Application Priority Data

Dec. 21, 2016 (NZ) ........................... 727745
Dec. 21, 2016 (NZ) ........................... 727747

(51) Int. Cl.
| | | |
|---|---|---|
| G01N 27/414 | (2006.01) | |
| G01N 27/12 | (2006.01) | |
| G01N 33/543 | (2006.01) | |

(52) U.S. Cl.
CPC ......... G01N 27/414 (2013.01); G01N 27/122 (2013.01); G01N 33/5438 (2013.01)

(58) Field of Classification Search
CPC ............... G01N 27/414; G01N 27/122; G01N 33/5438; G01N 27/4146; G01N 27/4145; G01N 27/124; B82Y 15/00; C07K 14/705
See application file for complete search history.

(56) References Cited

U.S. PATENT DOCUMENTS

| | | | |
|---|---|---|---|
| 6,024,924 A | 2/2000 | Schoning et al. | |
| 2011/0059544 A1* | 3/2011 | Hong ................. | G01N 27/4145 257/253 |

(Continued)

FOREIGN PATENT DOCUMENTS

| | | | | |
|---|---|---|---|---|
| CA | 2616144 A1 | 3/2009 | | |
| EP | 2848929 A1 * | 3/2015 | ......... | G01N 27/4145 |

(Continued)

OTHER PUBLICATIONS

Carraher et al. (Carraher Colm et al., Recombinant expression, detergent solubilization and purification of insect odorant receptor subunits, Protein Expression and Purification 90 (2013) 160-169, cited in IDS) (Year: 2013).*

(Continued)

*Primary Examiner* — Joshua L Allen
(74) *Attorney, Agent, or Firm* — Leydig, Voit & Mayer, Ltd.

(57) ABSTRACT

The invention provides a sensor device comprising an insect odorant receptor (OrX) in electrical communication with a substrate, wherein the sensor device is configured to detect (Continued)

a change in an electrical characteristic of the substrate. The invention also provides sensor device component comprising an insect odorant receptor (OrX) in electrical communication with a substrate. The invention also provides methods for manufacture and use of the sensor device and sensor device component. The invention also provides methods of use of the sensor to detect an analyte.

15 Claims, 39 Drawing Sheets

(56) References Cited

U.S. PATENT DOCUMENTS

| | | | | | |
|---|---|---|---|---|---|
| 2015/0065363 | A1* | 3/2015 | Johnson, Jr. | ......... | G01N 33/554 436/501 |
| 2017/0299602 | A1* | 10/2017 | Johnson, Jr. | ....... | G01N 33/6842 |

FOREIGN PATENT DOCUMENTS

| | | | | |
|---|---|---|---|---|
| EP | 2848929 | A1 | 3/2015 | |
| JP | H11-511564 | A | 10/1999 | |
| WO | WO 2000/043410 | A2 | 7/2000 | |
| WO | WO 2000/050566 | A2 | 8/2000 | |
| WO | WO 2002/068593 | A2 | 9/2002 | |
| WO | WO 2002/077200 | A2 | 10/2002 | |
| WO | WO 2005/062780 | A2 | 7/2005 | |
| WO | WO 2009/136742 | A1 | 11/2009 | |
| WO | WO 2012/050646 | A2 | 4/2012 | |
| WO | WO 2012/154403 | A2 | 11/2012 | |
| WO | WO-2013034666 | A2 * | 3/2013 | .......... C07K 14/705 |
| WO | WO 2017/122338 | A1 | 7/2017 | |
| WO | WO 2018/116186 | A1 | 6/2018 | |

OTHER PUBLICATIONS

Carraher (Colm Carraher, Characterisation of the insect odorant receptor complex, The University of Ackland, New Zealand, PhD Thesis, Sep. 2013) (Year: 2013).*
Sato et al. (Koji Sato, Shoji Takeuchi, Chemical vapor detection using a reconstituted insect olfactory receptor complex, Angew. Chem. Int. Ed. 53 (2014) 11798-11802) (Year: 2014).*
Sato et al. (Koji Sato et al., Insect olfactory receptors are heteromeric ligand-gated ion channels, Nature 152 (2008) 1002-1006) (Year: 2008).*
Bachtiar et al. (2013) "Multilayer Perceptron Classification of Unknown Volatile Chemicals from the Firing Rates of Insect Olfactory Sensory Neurons and Its Application to Biosensor Design," Neural Computation 25(1): 259-287.
Bayburt et al. (2003) "Self-assembly of single integral membrane proteins into soluble nanoscale phospholipid bilayers," Protein Sci. 12(11): 2476-2481.
Bayburt et al. (2010) "Membrane protein assembly into Nanodiscs," FEBS Lett. 584(9): 1721-1727.
Boyle et al. (2013) "Expanding the olfactory code by in silico decoding of odor-receptor chemical space," eLife 2: e01120, pp. 1-17.
Carey et al. (2010) "Odorant reception in the malaria mosquito Anopheles gambiae," Nature 464(7285): 66-71.
Claudianos et al. (2014) "Odor memories regulate olfactory receptor expression in the sensory periphery," Eur. J. Neurosci. 39(10): 1642-1654.
Corcoran et al. (2014) "A novel method to study insect olfactory receptor function using HEK293 cells," Insect Biochem Mol Biol 54: 22-32.
Dweck et al. (Feb. 2015) "Olfactory proxy detection of dietary antioxidants in Drosophila," Curr Biol 25(4): 455-466.
Figueroa et al. (2010) "Large-scale investigation of the olfactory receptor space using a microfluidic microwell array," Lab Chip 10(9): 1120-1127.

Forstner et al. (2009) "A receptor and binding protein interplay in the detection of a distinct pheromone component in the silkmoth Antheraea polyphemus," International Journal of Biological Sciences 5(7): 745-757.
Goldsmith et al. (2011) "Biomimetic chemical sensors using nanoelectronic readout of olfactory receptor proteins," ACS Nano 5(7): 5408-5416.
Grosse-Wilde et al. (2006) "A pheromone-binding protein mediates the bombykol-induced activation of a pheromone receptor in vitro," Chemical Senses 31(6): 547-555.
Hallem et al. (2006) "Coding of odors by a receptor repertoire," Cell 125(1): 143-160.
Hopf et al. (Jan. 2015) "Amino acid coevolution reveals three-dimensional structure and functional domains of insect odorant receptors," Nat Commun. 13(6): 6077, pp. 1-7.
International Preliminary Report on Patentability, dated Apr. 18, 2019, corresponding to International Application No. PCT/IB2017/058181 (filed Dec. 20, 2017), 6 pp.
International Search Report and Written Opinion, dated Apr. 3, 2018, corresponding to International Application No. PCT/IB2017/058181 (filed Dec. 20, 2017), 9 pp.
Jones et al. (2011) "Functional agonism of insect odorant receptor ion channels" with Corrections (11297-11298), Proc. Natl. Acad. Sci. U S A 108(21): 8821-8825.
Jordan et al. (2009) "Odorant receptors from the light brown apple moth (Epiphyas postvittana) recognize important volatile compounds produced by plants," Chemical Senses 34(5): 383-394.
Kuang et al. (2010) "Biomimetic Chemosensor: Designing Peptide Recognition Elements for Surface Functionalization of Carbon Nanotube Field Effect Transistors," ACS Nano 4(1): 452-458.
Kumar et al. (2013) "A conserved aspartic acid is important for agonist (VUAA1) and odorant/tuning receptor-dependent activation of the insect odorant co-receptor (Orco)," PLOS One 8(7): e70218.
Leary et al. (2012) "Single mutation to a sex pheromone receptor provides adaptive specificity between closely related moth species," Proc Natl Acad Sci 109(35): 14081-14086.
Misawa et al. (2010) "Highly sensitive and selective odorant sensor using living cells expressing insect olfactory receptors," Proc. Natl. Acad. Sci. U. S. A. 107(35): 15340-15344.
Miura et al. (2009) "A male-specific odorant receptor conserved through the evolution of sex pheromones in Ostrinia moth species," International Journal of Biological Sciences 5(4): 319-330.
Nowotny et al. (2014) "Drosophila olfactory receptors as classifiers for volatiles from disparate real world applications," Bioinspiration & Biomimetics 9: 046007, pp. 1-13.
Pask et al. (2013) "The molecular receptive range of a lactone receptor in Anopheles gambiae," Chemical Senses 38(1): 19-25.
Robertson et al. (2003) "Molecular evolution of the insect chemoreceptor gene superfamily in Drosophila melanogaster," PNAS Nov. 25, 2003 100 (suppl 2): 14537-14542.
Sakurai et al. (2004) "Identification and functional characterization of a sex pheromone receptor in the silkmoth Bombyx mori," Proceedings of the National Academy of Sciences of the United States of America 101(47): 16653-16658.
Silbering et al. (2011) "Complementary function and integrated wiring of the evolutionarily distinct Drosophila olfactory subsystems," Journal of Neuroscience 31(38): 13357-13375.
Stern et al. (2007) "Importance of the debye screening length on nanowire field effect transistor sensors," Nano Lett. 7(11): 3405-3409.
Turner et al. (2014) "Mutational analysis of cysteine residues of the insect odorant co-receptor (Orco) from Drosophila melanogaster reveals differential effects on agonist- and odorant-tuning receptor-dependent activation," Journal of Biological Chemistry 289(46): 31837-31845.
Wang et al. (2010) "Molecular basis of odor coding in the malaria vector mosquito Anopheles gambiae," Proc Natl. Acad. Sci. USA 107(9): 4418-4423.
Wanner et al. (2010) "Sex Pheromone Receptor Specificity in the European Corn Borer Moth, Ostrinia nubilalis," Plos One 5(1): e8685, pp. 1-9.
Xu et al. (2012) "Moth Sex Pheromone Receptors and Deceitful Parapheromones," Plos One 7(7): e41653, pp. 1-9.

(56) References Cited

OTHER PUBLICATIONS

Zhu et al. (Aug. 2015) "Label-free electrochemical aptasensor for femtomolar detection of 17β-estradiol," Biosensors and Bioelectronics 70: 398-403.
Anderson et al. (2009) "Molecular basis of female-specific odorant responses in Bombyx mori," Insect Biochemistry and Molecular Biology 39(3): 189-197.
Australian Exam Report No. 1 dated Aug. 2, 2022 in corresponding Application No. AU 2017383462 A1.
Bachtiar et al. (publicly available Nov. 2014) "Using Multilayer Perceptron Computation to Discover Ideal Insect Olfactory Receptor Combinations in the Mosquito and Fruit Fly for an Efficient Electronic Nose," Neural Computation (Jan. 2015) 27(1): 171-201.
Booth et al. (2011) "Development of an electrochemical polypyrrole-based DNA sensor and subsequent studies on the effects of probe and target length on performance," Biosensors and Bioelectronics 28(1): 362-367.
Booth et al. (2012) "Effects of Redox Couple on the Response of Polypyrrole-Based Electrochemical DNA Sensors," Electroanalysis 24(6): 1311-1317.
Bowie et al. (1990) "Deciphering the message in protein sequences: tolerance to amino acid substitutions," Science 247(4948): 1306-1310.
Carraher et al. (2013) "Recombinant expression, detergent solubilisation and purification of insect odorant receptor subunits," Protein Expr Purif 90(2): 160-169.
Carraher et al. (Nov. 2015) "Towards an understanding of the structural basis for insect olfaction by odorant receptors," Insect Biochemistry and Molecular Biology 66: 31-41.
Chinese First Office Action dated Jun. 30, 2021 in corresponding Application No. CN 2017800869324.
Chinese First Search dated Jun. 22, 2021 in corresponding Application No. CN 2017800869324.
Du et al. (2013) "Piezoelectric olfactory receptor biosensor prepared by aptamer-assisted immobilization," Sensors and Actuators B 187: 481-487.
Du et al. (2013) "Recent advances in olfactory receptor-based biosensors," Biosensors and Bioelectronics 42: 570-580.
Extended European Search Report dated Jul. 29, 2020 in corresponding Application No. EP 17885391.7.
Geertsma et al. (2008) "Membrane reconstitution of ABC transporters and assays of translocator function," Nature Protocols 3(2): 256-266.
Glatz et al. (2011) "Mimicking nature's noses: From receptor deorphaning to olfactory biosensing," Prog Neurobiol 93(2): 270-296.
Grosse-Wilde et al. (2007) "Candidate pheromone receptors provide the basis for the response of distinct antennal neurons to pheromonal compounds," European Journal of Neuroscience 25(8): 2364-2373.
Heller et al. (2008) "Identifying the mechanism of biosensing with carbon nanotube transistors," Nano Lett. 8(2): 591-595.
Hill et al. (2002) "G protein-coupled receptors in Anopheles gambiae," Science 298(5591): 176-178.
Hossein-Babaei et al. (2010) "Gas analysis by monitoring molecular diffusion in a microfluidic channel," Analytical Chemistry 82(19): 8349-8355.
Hossein-Babaei et al. (2012) "A miniature gas analyzer made by integrating a chemoresistor with a microchannel," Lab Chip 12(10): 1874-1880.
HUANG (1994) "On Global Sequence Alignment," Computer Applications in the Biosciences 10: 227-235.
Japanese Notice for Reasons for Refusal dated Nov. 26, 2021 in corresponding Application No. JP 2019-534131.
Japanese Search Report dated Nov. 11, 2021 in corresponding Application No. JP 2019-534131.
Jeanmougin et al. (1998) "Multiple sequence alignment with Clustal X," Trends Biochem. Sci. 23(10): 403-405.
Kannan et al. (2011) "High-Sensitivity, Label-Free DNA Sensors Using Electrochemically Active Conducting Polymers," Analytical Chemistry 83(9): 3415-3421.
Kiely et al. (2007) "Functional analysis of a Drosophila melanogaster olfactory receptor expressed in Sf9 cells," J. Neurosci. Methods 159(2): 189-194.
Lee et al. (Sep. 2015) "Bioelectronic nose combined with a microfluidic system for the detection of gaseous trimethylamine," Biosensors and Bioelectronics 71: 179-185.
Liu et al. (2013) "Identification and functional characterization of sex pheromone receptors in beet armyworm *Spodoptera exigua* (Hubner)," Insect Biochemistry and Molecular Biology 43(8): 747-754.
Liu et al. (2013) "Insect olfactory receptors as essential detectors for volatile chemicals in biomimetic odorant sensors," Applied Mechanics and Materials 461: 822-828.
Lu et al. (2014) "Olfactory biosensor using odorant-binding proteins from honeybee: Ligands of floral odors and pheromones detection by electrochemical impedance," Sensors and Actuators B: Chemical 193: 420-427.
Matsubara et al. (2004) "Application of on-chip cell cultures for the detection of allergic response," Biosensors and Bioelectronics 19(7): 741-747.
Mitsuno et al. (2008) "Identification of receptors of main sex-pheromone components of three Lepidopteran species," European Journal of Neuroscience 28(5): 893-902.
Mitsuno et al. (Mar. 2015) "Novel cell-based odorant sensor elements based on insect odorant receptors," Biosens. Bioelectron. 65: 287-294.
Montagne et al. (2015) "Chapter Three—Advances in the identification and characterization of olfactory receptors in insects," Progress in molecular biology and translational science 130: 55-80.
Plank et al. (2005) "Positioning of carbon nanotubes using soft-lithography for electronics applications," J. Vac. Sci. Technol. B Microelectron. Nanom. Struct. 23(6): 3178-3181.
Sankaran et al. (2011) "Odorant binding protein based biomimetic sensors for detection of alcohols associated with *Salmonella* contamination in packaged beef," Biosensors and Bioelectronics 26(7): 3103-3109.
Schott et al. (2013) "Insect Antenna-Based Biosensors for In Situ Detection of Volatiles," Advances in Biochemical Engineering and Biotechnology 136: 101-122.
Smart et al. (2008) "*Drosophila* odorant receptors are novel seven transmembrane domain proteins that can signal independently of heterotrimeric G proteins," Insect Biochem Mol Biol. 38(8):770-780.
Wang et al. (2011) "Functional characterization of pheromone receptors in the tobacco budworm Heliothis virescens," Insect Molecular Biology 20(1): 125-133.
Zheng et al. (Jun. 2016) "Electrostatic gating in carbon nanotube aptasensors," Nanoscale 8(28): 13659-13668.
Zheng et al. (Nov. 2015) "Carbon nanotube field effect transistor aptasensors for estrogen detection in liquids," J. Vac. Sci. Technol. B 33(6): 06F904.
Zhu et al. (Feb. 2015) "Distinguishing cytosine methylation using electrochemical, label-free detection of DNA hybridization and ds-targets," Biosensors and Bioelectronics 64: 74-80.

\* cited by examiner

A)

A)

B)

C)

D)

A)

B)

C)

D)

A)

B)

C)

D)

E)

A)

B)

C)

D)

A)

B)

a)

e)

i)

b)

f)

j)

c)

g)

k)

d)

h)

l)

SENSOR DEVICE AND METHODS

CROSS-REFERENCE TO RELATED APPLICATIONS

This application is a U.S. National Stage Application filed under 35 U.S.C. § 371 of International Application No. PCT/IB2017/058181, filed Dec. 20, 2017, which claims the benefit of New Zealand Application No. 727745, filed Dec. 21, 2016, and New Zealand Application No. 727747, filed Dec. 21, 2016. All of these applications are hereby incorporated by reference in their entireties.

TECHNICAL FIELD

The invention relates to sensors and methods for detecting analytes.

BACKGROUND

Real-time detection of analytes such as Volatile Organic Compounds (VOCs), and soluble organic chemicals is a critical challenge for health and environmental monitoring, as well as food safety and water quality, and there are strong drivers to develop affordable and rapid analyte sensors.

Convenient, sensitive and specific analyte sensors would have diverse applications including monitoring analytes associated with food quality/safety (flavours, ripening, contamination, and spoilage), biosecurity (pest and diseases), environmental monitoring (hazardous pollutants), medical diagnostics (e.g. breath diagnostics) and security (illicit compounds and explosives).

Insect olfactory receptors (ORs) can distinguish among a wide range of natural and synthetic chemicals, including VOCs. Insect ORs function as heteromeric ligand-gated cation channels (FIG. 1), and are composed of an obligate co-receptor known as Orco and an odorant-specific tuning receptor (OrX).

Insect ORs are structurally and functionally very different from mammalian and *Caenorhabditis elegans* ORs which function as G protein-coupled receptors (GPCRs).

A number of authors have described cell based assays for insect OR function[1] using *Xenopus oocytes*[2], insect cell lines[3], and human HEK293 cells[4]. However, their application was largely limited to identifying the compound specificity of insect ORs, with some being used to identify activating and inhibitory compounds for insect pest behaviour controls.

A number of published patent documents describe insect OR cell-assays[6-11]. All cover approaches to assay for novel activating and inhibitory compounds for insect pest control. In terms of cell-based sensors, two publications[12,13] describe use of cell lines expressing insect ORs in cell-based sensor formats. One publication demonstrates the use of *Xenopus oocytes* transfected with insect ORs to detect odorants using a two-electrode voltage clamp method[12], while the other[13] describe a cell line that expresses a pheromone receptor being grown on a glass microfluidic chip and pheromone binding being detected by calcium imaging using a fluorescent microscope.

All of the insect OR-based systems/sensors described above include insect OrXs together with their associated Orcos.

Commercially available portable volatile sensing technologies are limited to electronic/chemical e-noses, whose performance is substantially inferior to insect olfactory systems, in terms of sensitivity and specificity. Furthermore, to the best of the applicant's knowledge, there are no commercial products based on insect OR-based systems discussed above. Other technologies such as ion mobility spectrometers and mass spectrometers provide an improved sensitivity and specificity over e-noses but are very expensive to purchase, require extensive user training and are not very mobile.

It is therefore an object of the invention to provide an improved sensor device utilising at least one insect receptor and/or at least to provide the public with a useful choice.

SUMMARY OF THE INVENTION

The invention provides a sensor device comprising an insect OrX coupled to the display surface/substrate of the sensor. To the best of the applicant's knowledge this is the first time a purified insect OrX has been functionally immobilised on a sensor display surface/substrate.

The inventors have surprisingly shown that the novel sensor provides a highly significant increase in sensitivity relative to previously used insect OR-based systems. Further surprisingly, the inventors have shown that the novel sensor is functional in the absence of an Orco.

The Sensor Device

In the first aspect the invention provides a sensor device comprising an insect odorant receptor (OrX) in electrical communication with a substrate, wherein the sensor device is configured to detect a change in an electrical characteristic of the substrate.

In one embodiment the change in the electrical characteristic results from an interaction between the OrX and an analyte.

In a further embodiment the interaction is binding of the analyte to the OrX.

In a further embodiment the analyte is complementary to the OrX.

In a further embodiment the interaction between the analyte and the OrX is specific.

Detection of Analyte

Thus in one embodiment the sensor is capable of detecting binding of an analyte to the OrX by detecting the change in the electrical characteristic of the substrate.

In a further embodiment the sensor is capable of detecting, in an environment, the presence of an analyte that binds to the insect OrX.

Preferably detection is specific for the analyte.

Electrical Communication

In one embodiment in electrical communication means that the receptor can influence the electrical characteristic of the substrate.

In a further embodiment the interaction between the analyte and the OrX results in a conformational change in the OrX.

In a further embodiment the conformational change in the OrX results in the change in the electrical characteristic of the substrate.

Coupling of the OrX to the Substrate

In a further embodiment the OrX is coupled to the substrate.

Presentation of the OrX

In a further embodiment the OrX is present in a form that is capable of undergoing a conformational change in response to interaction with the analyte.

In a further embodiment the OrX is present in a membrane mimic.

The membrane mimic may be selected from a liposome, an amphipole, a detergent micelle, a nanovesicle, a lipid bilayer, and a nanodisc.

Preferably the membrane mimic is artificial.

The OrX may also be present in a surfactant, which may be ionic or non-ionic.

Sensitivity of Detection

In one embodiment the sensor can detect the presence of the analyte at a concentration of less than $1\times10^{-3}$M, preferably less than $1\times10^{-3}$M, more preferably less than $1\times10^{-4}$M, more preferably less than $1\times10^{-5}$M, more preferably less than $1\times10^{-6}$M, more preferably less than $1\times10^{-7}$M, more preferably less than $1\times10^{-8}$M, more preferably less than $1\times10^{-9}$M, more preferably less than $1\times10^{-10}$M, more preferably less than $1\times10^{-11}$M, more preferably less than $1\times10^{-12}$M, more preferably less than $1\times10^{-13}$M, more preferably less than $1\times10^{-14}$M, more preferably less than $1\times10^{-15}$M, more preferably less than $1\times10^{-16}$M, more preferably less than $1\times10^{-17}$M, more preferably less than $1\times10^{-18}$M.

Lack of Orco in the Sensor Device

In a further embodiment the sensor does not include an insect odorant co-receptor (Orco).

Substrate

In one embodiment the substrate is selected from, or composed of, at least one of: an electrode, a semiconductor material, carbon nanotubes (CNTs), graphene, an oxide, doped silicon, a conducting polymer, a resonator component.

In one embodiment the resonator component is, or is composed of, a piezoelectric material, at least one piezoelectric crystal, a quartz crystal. In a preferred embodiment the resonator component is a quartz crystal resonator.

Electrical Characteristic

In one embodiment the electrical characteristic is selected from at least one of: conductivity, resistance, complex resistance, impedance, electrochemical impedance, the flow of current, and the resonance frequency of oscillations induced by an alternating electric field.

Detector Component

In a further embodiment the sensor comprises a detector component which measure the change in the electrical characteristic of the substrate.

Electrochemical Impedance Spectroscopy (EIS) Sensor Device

In one embodiment of the sensor device, the substrate is the working electrode of an electrochemical cell.

In a one embodiment the electrochemical cell, in addition to the working electrode, further comprises a counter electrode.

In a further embodiment the electrochemical cell further comprises a reference electrode.

In a further embodiment the electrochemical cell further comprises a potentiostat.

In a further embodiment the electrical characteristic is electrochemical impedance.

Thus in one embodiment the sensor device comprises an OrX in electrical communication with working electrode of an electrochemical cell, wherein sensor device is configured to detect a change in the electrochemical impedance of the working electrode.

Working Electrode of EIS Sensor Device

In one embodiment the working electrode is composed of, or coated with, gold.

Presentation of the OrX in the EIS Sensor Device

The OrX may be present in a membrane mimic as described above.

In one embodiment the OrX is present in a liposome.

In a further embodiment the OrX is present in an artificial liposome.

In a further embodiment the OrX is present in a lipid bilayer.

In a further embodiment the OrX is present in an artificial lipid bilayer.

In a further embodiment the OrX is present in a nanodisc.

Coupling of the Insect OrX to the Electrode in the EIS Sensor Device

In one embodiment the insect OrX is coupled to the working electrode.

In a further embodiment the insect OrX is coupled to the working electrode via a linker molecule.

In a further embodiment the linker molecule is short enough to allow electrical communication between the OrX and the electrode.

In one embodiment the linker molecule is short enough to prevent isolation of the electrode from the receptor.

In a further embodiment the linker molecule is selected from 16-Mercaptohexadecanoic acid (16-MHDA), 6-Mercaptohexadecanoic acid (6-MHDA) and 6-Mercaptohexanoic acid (MHA).

In a preferred embodiment the linker molecule is 6-Mercaptohexanoic acid (MHA).

In a further embodiment the linker is part of a Self-Assembled Mono (SAM) layer.

Thus in one embodiment the insect OrX is coupled to the electrode via an SAM layer composed of the linker molecules.

In a preferred embodiment the insect OrX is coupled to the electrode via an SAM layer composed of 6-Mercaptohexanoic acid (MHA) linker molecules.

Detection of Analyte in the EIS Sensor

In a further embodiment the sensor is capable of detecting binding of an analyte to the insect OrX.

In a further embodiment the sensor is capable of detecting, in an environment, the presence of an analyte that binds to the insect OrX.

Preferably detection is specific for the analyte.

In a further embodiment binding of the analyte to the insect OrX changes the electrochemical impedance of the working electrode.

In a preferred embodiment the electrochemical impedance of the working electrode decreases upon binding of the analyte to the insect OrX.

In a preferred embodiment as the amount of analyte detected by the sensor, or binding to the insect OrX, changes, the electrochemical impedance of the working electrode decreases.

Detector Component

In a further embodiment the sensor comprises a detector component. In a further embodiment the detector component detects, or measures the change in electrochemical impedance of the working electrode.

Semiconductor-Based Sensor Device

In one embodiment of the sensor device, the substrate is a semiconductor material. Any suitable semiconductor material may be used.

In one embodiment of the sensor device, the semiconductor material is or is composed of at least one of: graphene, an oxide, doped silicon, conducting polymer, and carbon nanotubes (CNT).

Carbon Nanotube-Field Effect Transistor (CNT-FET) Sensor Device

In one embodiment the substrate composed of carbon nanonubes (CNT). The carbon nanonubes (CNTs) may be single wall, double wall or multiwall, or a combination thereof. In a preferred embodiment the carbon nanonubes (CNTs) are single wall.

In a further embodiment the substrate forms the channel of a carbon nanotube-field effect transistor (CNT-FET) apparatus.

In one embodiment the CNT-FET apparatus comprises a source electrode and a drain electrode.

In a further embodiment the channel is found, or formed, between the source electrode and a drain electrode.

In a further embodiment the channel is in electric communication with the source electrode and a drain electrode.

Thus in one aspect the invention provides a sensor device comprising an insect odorant receptor (OrX) in electrical communication with at least one carbon nanotube in the channel of a carbon nanotube-field effect transistor (CNT-FET) apparatus.

In a further embodiment the carbon nanotube-field effect transistor (CNT-FET) apparatus also comprised a gate electrode.

Presentation of the OrX in the CNT-FET Sensor Device

The OrX may be present in a membrane mimic as described above.

In a preferred embodiment the OrX is present in a nanodisc.

Coupling of the OrX to the Carbon Nanotube (CNT)

In one embodiment the OrX is coupled to the carbon nanotube in the channel.

In a further embodiment the coupling places the OrX in electrical communication with the carbon nanotube.

Insect OrX Functionalisation

In one embodiment the insect OrX is functionalised to facilitate coupling to the CNTs In one embodiment the insect OrX is functionalised with a his-tag.

Therefore, in one embodiment the OrX comprises a his-tag.

Preferably the his-tag is at the N-terminus of the OrX protein

CNT Functionalisation

In one embodiment CNT is functionalised to facilitate coupling to the the insect OrX In a further embodiment the CNTs are functionalised with nickel (Ni)-nitrilotriacetic acid (NTA)

Coupling

In a further embodiment the OrX is coupled to the CNTs via his-tag affinity binding.

Thus in one embodiment the his-tagged Orx binds to the Ni-NTA functionalised CNT.

Detection of Analyte in the CNT-FET Sensor

In a further embodiment the sensor is capable of detecting binding of an analyte to the insect OrX.

In a further embodiment the sensor is capable of detecting, in an environment, the presence of an analyte that binds to the insect OrX.

Preferably detection of the analyte is specific.

In a further embodiment binding of the analyte to the insect OrX changes the source-gain current in the CNT-FET apparatus.

In a preferred embodiment the source-gain current decreases upon binding of the analyte to the insect OrX.

In a preferred embodiment as the amount of analyte detected by the sensor, or binding to the insect OrX increases, the more the source-gain current decreases.

Detector Component

In a further embodiment the sensor comprises a detector component. In a further embodiment the detector component detects, or measures the change in the source-drain current.

Quartz Crystal Microbalance (QCM) Sensor Device

In one embodiment of the sensor device, the substrate is a resonator component in quartz crystal microbalance.

In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

Electrical Characteristic

In one embodiment the electrical characteristic is the resonance frequency of oscillations induced by an alternating electric field applied to the resonator component.

Electrodes of the QCM Sensor Device

In one embodiment the resonator component has at an electrode attached to two of it opposing side.

In one embodiment the electrodes are composed of, or coated with, gold.

Presentation of the OrX in the QCM Sensor Device

The OrX may be present in a membrane mimic as described above.

In one embodiment the OrX is present in a liposome.

In a further embodiment the OrX is present in an artificial liposome.

In a further embodiment the OrX is present in a lipid bilayer.

In a further embodiment the OrX is present in an artificial lipid bilayer.

In a preferred embodiment the OrX is present in a liposome.

Coupling of the Insect OrX to the Resonator Component in the QCM Sensor Device

In one embodiment the insect OrX is coupled to the resonator component.

In a further embodiment the insect OrX is coupled to the resonator component via a linker molecule.

In a further embodiment the linker molecule is short enough to allow electrical communication between the OrX and the resonator component.

In one embodiment the linker molecule is short enough to prevent isolation of the resonator component from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker molecule is 6-mercaptohexanoic acid (MHA).

In a further embodiment the linker is part of a Self-Assembled Monolayer (SAM).

Thus in one embodiment the insect OrX is coupled to the resonator component via an SAM layer composed of the linker molecules.

In a preferred embodiment the insect OrX is coupled to the resonator component via an SAM layer composed of 6-mercaptohexanoic acid (MHA) linker molecules.

Detection of Analyte with the QCM Sensor

In a further embodiment the sensor is capable of detecting binding of an analyte to the insect OrX.

In a further embodiment the sensor is capable of detecting, in an environment, the presence of an analyte that binds to the insect OrX.

Preferably detection is specific for the analyte.

In a further embodiment binding of the analyte to the insect OrX changes the resonance frequency induced by an alternating electric field applied to the resonator component.

In one embodiment the resonance frequency increases upon binding of the analyte to the insect OrX.

In a further embodiment the resonance frequency decreases upon binding of the analyte to the insect OrX.

Detector Component

In a further embodiment the sensor comprises a detector component. In a further embodiment the detector component detects, or measures the change in the resonance frequency in the resonator component induced by an alternating electric field applied to the resonator component.

In one embodiment the detector component is a frequency analyser.

Method Using the Sensor Device of the Invention to Detect Analyte Binding

In a further aspect the invention provides a method of detecting an analyte, the method comprising the steps:
- a) binding of the analyte to the insect OrX in the sensor of the invention,
- b) detecting a change in an electrical characteristic of the substrate, wherein the change in the electrical characteristic of the substrate indicates detection of the analyte.

Method Using the Sensor Device of the Invention to Detect the Presence of Analyte in an Environment In a further aspect the invention provides a method of detecting the presence of an analyte in an environment, the method comprising the steps:
- a) exposing the sensor of the invention to an environment containing the analyte,
- b) binding of the analyte to the insect OrX in the sensor
- c) detecting a change in an electrical characteristic of the substrate, wherein the change in the electrical characteristic of the substrate indicates presence of the analyte in the environment.

Method Using the EIS Sensor Device of the Invention to Detect Analyte Binding

In a further aspect the invention provides a method of detecting an analyte, the method comprising the steps:
- a) binding of the analyte to the insect OrX in the electrochemical cell of the invention,
- b) measuring a change in electrochemical impedance in the working electrode, wherein the change in electrochemical impedance indicates detection of the analyte.

Method Using EIS Sensor Device of the Invention to Detect the Presence of Analyte in an Environment In a further aspect the invention provides a method of detecting the presence of an analyte in an environment, the method comprising the steps:
- a) exposing the sensor of the invention to an environment containing the analyte,
- b) binding of the analyte to the insect OrX in the electrochemical cell of the invention,
- c) measuring a change in the electrochemical impedance of the working electrode, wherein the change in electrochemical impedance indicates presence of the analyte in the environment.

Method Using the CNT-FET Sensor Device of the Invention to Detect Analyte Binding In a further aspect the invention provides a method of detecting an analyte, the method comprising the steps:
- a) binding of the analyte to the insect OrX in the sensor of the invention,
- b) measuring a change in source-gain current in the CNT-FET apparatus, wherein the change in source-gain current indicates detection of the analyte.

Method Using the CNT-FET Sensor Device of the Invention to Detect the Presence of Analyte in an Environment In a further aspect the invention provides a method of detecting the presence of an analyte in an environment, the method comprising the steps:
- a) exposing the sensor of the invention to an environment containing the analyte,
- b) binding of the analyte to the insect OrX in the sensor
- c) measuring a change of source-gain current in the CNT-FET apparatus, wherein the change in source-gain current indicates presence of the analyte in the environment.

Method Using the QCM Sensor Device of the Invention to Detect Analyte Binding

In a further aspect the invention provides a method of detecting an analyte, the method comprising the steps:
- a) binding of the analyte to the insect OrX in the sensor of the invention,
- b) measuring a change in the resonance frequency in the resonator component induced by an alternating electric field applied to the resonator component in the QCM apparatus, wherein the change in the resonance frequency indicates detection of the analyte.

Method Using the QCM Sensor Device of the Invention to Detect the Presence of Analyte in an Environment In a further aspect the invention provides a method of detecting the presence of an analyte in an environment, the method comprising the steps:
- d) exposing the sensor of the invention to an environment containing the analyte,
- e) binding of the analyte to the insect OrX in the sensor
- f) measuring a change of the resonance frequency of the resonator component induced by an alternating electric field applied to the resonator component in the QCM apparatus, where in the change in the resonance frequency indicates presence of the analyte in the environment.

Method of Manufacturing the Sensor Device of the Invention

In a further aspect the invention provides a method of manufacturing a sensor device the method including the step of establishing electrical communication between an insect OrX and the substrate of the sensor device, wherein the sensor device is configured to detect a change in an electrical characteristic of the substrate.

In one embodiment the method includes the step of coupling of the insect OrX to the substrate.

In one embodiment the OrX is coupled to the substrate before the OrX coupled substrate is assembled in the sensor device.

Preferably the components, coupling and functionality of the sensor is/are as described herein.

Method of Manufacturing the EIS Sensor Device of the Invention

In embodiment the substrate is the working electrode of an electrochemical cell as described herein.

Thus in one embodiment method comprises the step of establishing electrical communication between an insect OrX and the working electrode of an electrochemical cell, wherein electrochemical cell is configured to detect a change in the electrochemical impedance of the working electrode thus forming the sensor device.

In one embodiment the method includes the step of coupling of the insect OrX to the working electrode.

In one embodiment the OrX is coupled to the working electrode before the OrX coupled working electrode is assembled in the sensor device.

Preferably the components, coupling and functionality of the sensor is/are as described herein.

Coupling of the Insect OrX to the Electrode

In a further embodiment the insect OrX is coupled to the electrode via a linker.

In one embodiment the linker molecule is short enough to allow electrical communication between the OrX and the electrode.

In a further embodiment the linker molecule is short enough to prevent isolation of the electrode from the receptor.

In a further embodiment the linker molecule is selected from 16-Mercaptohexadecanoic acid (16-MHDA), 6-Mecaptohexadecanoic acid (6-MHDA) and 6-Mercaptohexanoic acid (MHA).

In a preferred embodiment the linker molecule is 6-Mercaptohexanoic acid (MHA).

In a further embodiment the linker is part of a Self-Assembled Mono (SAM) layer.

Thus in one embodiment the insect Orx is coupled to the electrode via an SAM layer composed of the linker molecules.

In a preferred embodiment the insect Orx is coupled to the electrode via an SAM layer composed of 6-Mercaptohexanoic acid (MHA) linker molecules.

In a further embodiment activation of the carboxylic groups of the linker, or MHA, is performed prior to coupling of the insect OrX.

Preferably, activation of the carboxylic groups of the linker, or MHA, is performed using a solution of 1-ethyl-3-(3-dimethyl amino propyl) carbodiimide (EDC) and N-hydroxysuccinimide (NHS), prior to coupling the insect OrX to the electrode.

Lack of Orco in the Sensor Device

In a preferred embodiment the sensor does not include an insect odorant co-receptor (Orco).

Method of Manufacturing the CNT-FET Sensor Device of the Invention

In embodiment the substrate is the channel of a CNT-FET apparatus as described herein.

Thus in one embodiment method comprises the step of establishing electrical communication between an insect OrX and the channel of an of a CNT-FET apparatus, wherein the CNT-FET apparatus is configured to detect a change in the source-gain current of the CNT-FET apparatus thus forming the sensor device.

In one embodiment the method includes the step of coupling of the insect OrX to the channel.

In one embodiment the OrX is coupled to the channel before the OrX coupled channel is assembled in the sensor device.

Preferably the components, coupling and functionality of the sensor is/are as described herein.

Coupling of the OrX to the Carbon Nanotube (CNT)

In one embodiment the OrX is coupled to the carbon nanotube in the channel.

Insect OrX Functionalisation

In one embodiment the insect OrX is functionalised to facilitate coupling to the CNTs In one embodiment the insect OrX is functionalised with a his-tag.

Therefore, in one embodiment the OrX comprises a his-tag.

Preferably the his-tag is at the N-terminus of the OrX protein

CNT Functionalisation

In one embodiment CNT is functionalised to facilitate coupling to the insect OrX In a further embodiment the CNTs are functionalised with nickel (Ni)-nitrilotriacetic acid (NTA)

Coupling

In a further embodiment the OrX is coupled to the CNTs via his-tag affinity binding.

Thus in one embodiment the his-tagged OrX binds to the Ni-NTA functionalised CNT.

Lack of Orco in the Sensor Device

In a preferred embodiment the sensor does not include an insect odorant co-receptor (Orco).

Method of Manufacturing the QCM Sensor Device of the Invention

In embodiment the substrate is the quartz crystal resonator of a quartz crystal microbalance.

Thus in one embodiment method comprises the step of establishing electrical communication between an insect OrX and the resonator component of a quartz crystal microbalance, wherein quartz crystal microbalance is configured to detect a change in the resonance frequency of the resonator component induced by an alternating electric field applied to the resonator component in the QCM apparatus, thus forming the sensor device.

In one embodiment the method includes the step of coupling of the insect OrX to the resonator component.

In one embodiment the OrX is coupled to the resonator component before the OrX coupled working resonator component is assembled in the sensor device.

Preferably the resonator component is a quartz crystal resonator.

Preferably the components, coupling and functionality of the sensor is/are as described herein.

Coupling of the Insect OrX to the Resonator Component

In a further embodiment the insect OrX is coupled to the resonator component via a linker.

In one embodiment the linker molecule is short enough to allow electrical communication between the OrX and the resonator component.

In a further embodiment the linker molecule is short enough to prevent isolation of the resonator component from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker molecule is 6-mercaptohexanoic acid (MHA).

In a further embodiment the linker is part of a Self-Assembled Monolayer (SAM).

Thus in one embodiment the insect Orx is coupled to the resonator component via an SAM layer composed of the linker molecules.

In a preferred embodiment the insect Orx is coupled to the resonator component via an SAM layer composed of 6-mercaptohexanoic acid (MHA) linker molecules.

In a further embodiment activation of the carboxylic groups of the linker, or MHA, is performed prior to coupling of the insect OrX.

Preferably, activation of the carboxylic groups of the linker, or MHA, is performed using a solution of 1-ethyl-3-(3-dimethyl amino propyl) carbodiimide (EDC) and N-hydroxysuccinimide (NHS), prior to coupling the insect OrX to the resonator component.

Lack of Orco in the Sensor Device

In a preferred embodiment the sensor does not include an insect odorant co-receptor (Orco).

DETAILED DESCRIPTION OF THE INVENTION

The applicant's invention successfully combines for the first time the smelling power of insect odorant receptors (OrXs) with a convenient sensor format.

In addition to the improved convenience, the sensor device of the invention surprisingly provides highly significant improvements in sensitivity of detection versus previous assay systems based on use of insects ORs.

Furthermore, the sensor of the invention is, surprisingly, able to function in the absence of odorant co-receptor (Orco), whereas all previous assay systems based on use of insects ORs relied on inclusion of both the OrX and Orco.

Insect Odorant Receptor Complexes

Insect odorant receptors (ORs) are members of a novel family of seven-transmembrane proteins that form ligand-gated non-selective cation channels. The highly conserved insect odorant co-receptor (Orco), is thought to form the active channel in vivo, with odorant specificity conferred by a panel of ligand-binding subunits (OrX) as represented in FIG. 1.

In vivo, the N-terminus of insect an OrX protein is cytoplasmic, while the C-terminus is extracellular. This topology is the opposite that of mammalian G-protein coupled receptors (GPCRs). In addition, unlike mammalian GPCRs, insect ORs function as ligand-gated non-selective cation channels, and signal largely independently of G proteins[15].

Hopf et al 2015[16] further discusses the predicted structure of insect ORs and their unrelatedness to mammalian GPCRs.

Insect OrX proteins, which may also be described as OrX polypeptides, are well known to those skilled in the art. Suitable OrX sequences for use in the invention include those from the *Drosophila melanogaster* OR gene family ([43]) which can detect a wide range of VOCs, ([44-46]), the *Anopheles gambiae* OR gene family ([47]) which can detect a wide range of VOCs ([48, 49]); as well as OR gene families from other insect species, for a recent list of known OR families see Table I of Montagne 2015 ([1]). In one embodiment the insect OrX protein comprises a sequence disclosed in such references[1, 43] and [47,] or a variant or functional fragment thereof.

In one embodiment the OrX is a recombinantly expressed protein.

In a preferred embodiment the OrX has been purified after recombinant expression.

In one embodiment the OrX is not purified directly from an insect olfactory cells.

In a further embodiment the OrX is not present in an insect olfactory cell in the sensor device.

Substrates for Use in the Sensor Device of the Invention

The substrate for use in the sensor device of the invention may be any substrate in which a change in an electrical characteristic can be measured. Preferably the change in the electrical characteristic is as a result of interaction between the OrX and the analyte.

The substrate also provides the surface to which the OrX can be coupled.

Suitable substrates include, or are composed, of at least one of: an electrode, a semiconductor material, carbon nanotubes (CNTs), graphene, an oxide, doped silicon, a conducting polymer, a resonator component.

In one embodiment the resonator component is, or is composed of, a piezoelectric material, at least one piezoelectric crystal, and a quartz crystal. In a preferred embodiment the resonator component is a quartz crystal resonator.

Electrical Characteristics to Measure in the Sensor Device of the Invention

In one embodiment the electrical characteristic is selected from at least one of: conductivity, resistance, complex resistance, impedance, electrochemical impedance, the flow of current, and the resonance frequency of oscillations induced by an alternating electric field.

EIS Device

In one embodiment the sensor device of the invention is configured to detect a change in electrochemical impedance in the working electrode of a chemical cell. Thus the sensor device in this embodiment is configured for Electrochemical Impedance Spectroscopy (EIS).

Electrochemical Impedance Spectroscopy (EIS)

Electrochemical Impedance Spectroscopy is well known to those skilled in the art, and has long been employed for studying electrochemical systems. For impedance measurements, a small sinusoidal AC voltage probe (typically 2-10 mV) is applied, and the current response is determined. The in-phase current response determines the real (resistive) component of the impedance, while the out-of-phase current response determines the imaginary (capacitive) component. The AC probe voltage should be small enough so that the system response is linear, allowing simple equivalent circuit analysis. Impedance methods are quite powerful, in that they are capable of characterizing physicochemical processes of widely differing time constants, sampling electron transfer at high frequency and mass transfer at low frequency.

Impedance results are commonly fitted to equivalent circuits of resistors and capacitors, such as the Randles circuit which is often used to interpret simple electrochemical systems. A schematic representation of the Randles circuit [Rs+CPE/(Rct+W)] is shown in FIG. 3 comprising of a solution resistance (Rs) in series with a constant phase element (CPE) and in parallel with charge transfer resistance (Rct) and Warburg diffusion element (W).

If an analyte affects one or more of these equivalent circuit parameters and these parameters are not affected by interfering species, then impedance methods can be used for analyte detection.

The Warburg impedance, which can be used to measure effective diffusion coefficients, is seldom useful for analytical applications. The equivalent circuit elements that are most often useful for analyte detection are Rct and CPE. The measured capacitance usually arises from the series combination of several elements, such as analyte binding to a sensing layer on a gold (Au) electrode.

Electrochemical Impedance Spectroscopy (EIS) Devices

EIS device typically comprise an electrochemical cell with:
- a working electrode (WE)
- a counter electrode (CE)
- a reference electrode (RE)
- a potentiostat/galvanostat (PGSTAT)

Depending on the application, the connections of the instrument to the electrochemical cell can be (or must be) set up in different ways.

In potentiostatic mode, a potentiostat/galvanostat (PG-STAT) will accurately control the potential of the Counter Electrode (CE) against the Working Electrode (WE) so that the potential difference between the working electrode (WE) and the Reference Electrode (RE) is well defined, and correspond to the value specified by the user. In galvanostatic mode, the current flow between the WE and the CE is controlled. The potential difference between the RE and WE and the current flowing between the CE and WE are continuously monitored. By using a PGSTAT, the value specified by the user (i.e. applied potential or current) is accurately controlled, anytime during the measurement by using a negative feedback mechanism.

The counter electrode (CE), is an electrode which is used to close the current circuit in the electrochemical cell. It is usually made of an inert material (e.g. Pt, Au, graphite, glassy carbon) and usually it does not participate in the electrochemical reaction. Because the current is flowing between the WE and the CE, the total surface area of the CE (source/sink of electrons) must be higher than the area of the WE so that it will not be a limiting factor in the kinetics of the electrochemical process under investigation.

The reference electrode (RE) is an electrode which has a stable and well-known electrode potential and it is used as a point of reference in the electrochemical cell for the potential control and measurement. The high stability of the reference electrode potential is usually reached by employing a redox system with constant (buffered or saturated) concentrations of each participants of the redox reaction. Moreover, the current flow through the reference electrode is kept close to zero (ideally, zero) which is achieved by using the CE to close the current circuit in the cell together with a very high input impedance on the electrometer (>100 GOhm).

The working electrode (WE) is the electrode in an electrochemical system on which the reaction of interest is occurring. Common working electrodes can be made of inert materials such as Au, Ag, Pt, glassy carbon (GC) and Hg drop and film.

The EIS device may also include a component to measure changes in an electrical property of the working electrode. For example, this component may be a frequency analyser. The frequency analyser may be linked to the potentiostat/galvanostat.

CNT-FET Device

In one embodiment the sensor device of the invention is configured to detect a change in source-gain current of the CNT-FET apparatus.

Carbon Nanotube Field-Effect Transistor (CNT-FET)

A carbon nanotube field-effect transistor (CNT-FET) is a field-effect transistor that utilizes a single carbon nanotube or an array of carbon nanotubes as the channel material instead of bulk silicon in the traditional metal-oxide-semiconductor field-effect transistor (MOS-FET) structure.

CNT-FET Devices

CNT-FET devices typically comprise:
a) a source electrode (SE)
b) a drain electrode (DE)
c) a gate electrode (GE), and
d) at least one channel composed of carbon nanotubes (CNTs)

The gate electrode is used to control the current across the source and drain electrodes. When the gate electrode is on, current flow is able to be modulated across the source and drain electrodes through the channel.

The electrodes are typically composed of at least one metal. Preferred metals include, but are not limited to: platinum, gold, chrome, copper, aluminium, tickle, palladium and titanium.

In a preferred embodiment the channel is composed of carbon nanotubes

The CNT-FET device may also include a component to measure changes in the source-drain current.

QCM Device

In one embodiment the sensor device of the invention is configured to detect a change in resonant oscillation frequency of the resonator component in a quartz crystal microbalance (QCM).

In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

Quartz Crystal Microbalance (QCM)

Quartz crystal microbalance (QCM) technology is well known to those skilled in the art, and measures a mass variation per unit area by measuring the change in frequency of a quartz crystal resonator. The resonance is disturbed by the addition or removal of a small mass due to oxide growth/decay or film deposition at the surface of the acoustic resonator. The QCM can be used under vacuum, in gas phase and in liquid environments. It is highly effective at determining the affinity of molecules (proteins, in particular) to surfaces functionalized with recognition sites. QCM has also been used to investigate interactions between biomolecules. Frequency measurements are easily made to high precision, hence, it is easy to measure mass densities down to a level of below 1 $\mu g/cm^2$. In addition to measuring the frequency, the dissipation factor (equivalent to the resonance bandwidth) is often measured to help analysis. The dissipation factor is the inverse quality factor of the resonance, $Q^{-1}=w/f_r$; it quantifies the damping in the system and is related to the sample's viscoelastic properties.

Quartz is one member of a family of crystals that experience the piezoelectric effect. The relationship between applied voltage and mechanical deformation is well known; this allows probing an acoustic resonance by electrical means. Applying alternating current to the quartz crystal will induce oscillations. With an alternating current between the electrodes of a properly cut crystal, a standing shear wave is generated. The Q factor, which is the ratio of frequency and bandwidth, can be as high as 106. Such a narrow resonance leads to highly stable oscillators and a high accuracy in the determination of the resonance frequency. The QCM exploits this ease and precision for sensing. Common equipment allows resolution down to 1 Hz on crystals with a fundamental resonant frequency in the 4-6 MHz range.

The frequency of oscillation of the quartz crystal is partially dependent on the thickness of the crystal. During normal operation, all the other influencing variables remain constant; thus a change in thickness correlates directly to a change in frequency. As mass is deposited on the surface of the crystal, the thickness increases; consequently the frequency of oscillation decreases from the initial value. With some simplifying assumptions, this frequency change can be quantified and correlated precisely to the mass change using the Sauerbrey equation.

Quartz Crystal Microbalance (QCM) Devices

A typical setup for the QCM contains water cooling tubes, the retaining unit, frequency sensing equipment through a microdot feed-through, an oscillation source, and a measurement and recording device.

The QCM consists of a resonator component (typically a thin piezoelectric plate) with electrodes evaporated onto both sides. Due to the piezo-effect, an AC voltage across the electrodes induces a shear deformation and vice versa. The electromechanical coupling provides a simple way to detect an acoustic resonance by electrical means. Otherwise, it is of minor importance.

Sensor Device of the Invention

In the first aspect the invention provides a sensor device comprising an insect odorant receptor (OrX) in electrical communication with a substrate, wherein the sensor device is configured to detect a change in an electrical characteristic of the substrate.

Sensor Component

In a further aspect the invention provides a component for a sensor device, the component comprising an OrX in electrical communication with a substrate as herein defined. This component is useful for adding to a sensor device according to the invention.

In one aspect the invention provides a sensor device component comprising an insect odorant receptor (OrX) in electrical communication with a substrate.

In one aspect the invention provides as sensor device comprising the sensor device component of the invention, wherein the sensor device is configured to detect a change in an electrical characteristic of the substrate.

In a further aspect the invention provides a method of manufacturing a sensor device component, the method including the step of establishing electrical communication between an insect OrX and a substrate.

In a further aspect the invention provides a method of assembling a sensor device, the method comprising adding sensor device component of the invention to the sensor device, wherein the assembled sensor device is configured to detect a change in an electrical characteristic of the substrate.

In certain embodiments of the sensor device component and sensor device, the insect odorant receptor (OrX), electrical communication, substrate, configuration, and detection, are as described herein.

Electrochemical Impedance Spectroscopy (EIS) Apparatus

In one embodiment the sensor device comprises an electrochemical cell.

In one embodiment the electrochemical cell comprises at least two electrodes.

In a further embodiment the electrochemical cell comprises at least:
a) a working electrode (WE), and
b) a counter electrode (CE)

In a preferred embodiment the electrochemical cell also comprises a reference electrode (RE).

In a further embodiment the electrochemical cell comprises a potentiostat/galvanostat (PGSTAT)

In a preferred embodiment the electrochemical cell comprises all of:
a) a working electrode (WE),
b) a counter electrode (CE),
c) a reference electrode (RE), and
d) potentiostat/galvanostat (PGSTAT).

Counter Electrode

In one embodiment the counter electrode is composed of, or coated with a material selected from platinum (Pt), gold (Au), graphite or glassy carbon (GC).

Preferably the counter electrode is composed of a platinum (Pt).

Preferably the counter electrode is a platinum (Pt) wire.

Reference Electrode

Preferably the reference electrode is a silver/silver chloride (Ag/AgCl) reference electrode Working Electrode In one embodiment the Electrochemical Impedance Spectroscopy (EIS) apparatus comprises at least one working electrode.

The electrode may be composed of, or coated with, any suitable material. The electrode may be composed of, or coated with, a material selected from gold (Au), silver Ag), platinum (Pt), carbon nanotubes (CNT) and glassy carbon (GC).

In a preferred embodiment the electrode is composed of, or coated with, gold.

Potentiostat/Galvanostat (PGSTAT)

Preferably the potentiostat/galvanostat (PGSTAT) is used in potentiostatic mode.

Detector Component

In a further embodiment the sensor comprises a detector component. The detector component detects, or measures the change in the electrical characteristic of the substrate.

In one embodiment the detector component is a frequency analyser. In a further embodiment the frequency analyser is linked to the potentiostat/galvanostat (PGSTAT).

Preparation of Insect OrXs

Methods for recombinantly expressing and purifying insect OrXs are known to those skilled in the art[14].

Presentation of the Insect OrX

In a further embodiment the OrX is present in a form that is capable of undergoing a conformational change in response to interaction with the analyte.

In one embodiment the insect OrX is present in a membrane mimic.

A membrane mimic as the name suggests mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In one embodiment the membrane mimic is a liposome.

In one embodiment the membrane mimic is an artificial liposome.

In a further embodiment the membrane mimic is a lipid bilayer.

In a further embodiment the membrane mimic is an artificial lipid bilayer.

Methods for reconstituting insect receptors in liposomes are known in the art[14].

Formation of a Lipid Bilayers Comprising the Insect OrX on the Working Electrode Without wishing to be bound by theory, the applicants postulate that in some embodiments when the insect OrXs in liposomes, are applied to the working electrode, the liposome changes structure to form a lipid bilayer on the electrode. The applicants postulate that the insect OrXs are embedded in the lipid bilayer in similar or same conformation as found in cell membranes in vivo, such that the ligand/analyte binding domain of the receptor of the accessible to the ligand/analyte.

Without wishing to be bound by theory, the applicants postulate that in other embodiments the liposomes remains as liposomes when bound to the working electrode. This is exemplified in FIG. 21.

Coupling of the OrX to the Substrate

In a further embodiment the OrX is coupled to the substrate.

Numerous methods for coupling proteins to substrates are known to those skilled in the art. Such methods include use of covalent chemical coupling, photochemical cross-linking, surface coating/modification, gold surface chemistry, protein affinity tags, biotin-streptavidin linkages, antibody immobilization, and engineered surface-binding peptide sequences.

The OrX proteins for use in the present devices may also include an amine group, a histidine tag, or some other functionalization used to couple the protein to the substrate. In the case of a protein having an amine group, the user may use the amine group to displace a leaving group coupled to the substrate so as to bind the protein to the substrate. The coupling need not necessarily be accomplished by a nucleophile-leaving group reaction, as coupling may occur by covalent bond (e.g., an amide bond), an ionic bond, by hydrogen bonding, or by metallic coordination. As one example of coordination, the OrX protein may be coupled to the substrate by coordination between a histidine tag and nickel. An OrX protein may also be coupled to the substrate by way of a cysteine residue. In some embodiments, the OrX protein to be attached naturally includes a cysteine residue. This could be naturally occurring or such a residue could be intentionally incorporated into a natural or recombinant protein. Further information may be found in WO2012050646.

In some embodiments, a surface of the substrate comprises a functional group linking the substrate to the transmembrane protein. In one non-limiting example, the surface of the material may be functionalized with carboxylated diazonium salts, which spontaneously form covalent bonds to substrates such as carbon nanotubes. Amine and amide functionalities are considered suitable, as are phenolic/aromatic functionalities.

Linker for EIS

In a further embodiment the insect OrX is coupled to the electrode via a linker.

In one embodiment the linker molecule is short enough to allow electrical communication between the OrX and the electrode.

In a further embodiment the linker molecule is short enough to prevent isolation of the electrode from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker is 6-Mercaptohexanoic acid (MHA).

In a further embodiment linker is part of a Self-Assembled Mono (SAM) layer.

Thus in one embodiment the SAM layer is composed 6-mercaptohexanoic acid (MHA).

In a further embodiment activation of the carboxylic groups of the MHA is performed prior to coupling of the insect OrX.

Preferably, activation of the carboxylic groups of the MHA is performed using a solution of 1-ethyl-3-(3-dimethyl amino propyl) carbodiimide (EDC) and N-hydroxysuccinimide (NHS), prior to coupling the insect OrX to the electrode.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OR changes the electrochemical impedance in the working electrode.

Carbon Nanotube Field-Effect Transistor (CNT-FET) Apparatus

Preferably the carbon nanotube field-effect transistor (CNT-FET) apparatus comprises at least two terminals. In a further embodiment the CNT-FET) apparatus comprises at least a source electrode and a drain electrode.

In one embodiment the CNT-FET) apparatus comprises:
a) a source electrode
b) a drain electrode
c) a gate electrode
d) at least one channel composed of carbon nanotubes (CNTs)

Preferably the gate electrode is a silver/silver chloride (Ag/AgCl) wire.

Detector Component

In a further embodiment the sensor comprises a detector component. The detector component detects, or measures the change in source-drain current.

Changes in electrical characteristics can be measured using conventional electronic instrumentation that is operated manually or under computer control. For example, a computerized laboratory set up might include a National Instrument PCI-6722 DAQ board to apply the bias voltage and various values of gate voltage. A Keithley 6485 Picoammeter could then be used to measure current, providing a full I-Vg curve. In the case where one wished to measure many devices located on a single substrate, a switching matrix (Keithley 7001) or other multiplexer could be used.

An Agilent 4156C parameter analyser can also be used for all electrical measurements[20]. The parameter analyser has excellent sensitivity and can accurately measure currents on the femto-amp scale.

Presentation of the Insect OrX

In a further embodiment the OrX is present in a form that is capable of undergoing a conformational change in response to interaction with the analyte.

In one embodiment the insect OrX is present in a membrane mimic.

A membrane mimic as the name suggests mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In a preferred embodiment the membrane mimic is a nanodisc.

Coupling of the OrX to the Channel in the CNT-FET Device of the Invention

In one embodiment the OrX is coupled to the carbon nanotube in the channel.

Insect OrX Functionalisation

In one embodiment the insect OrX is functionalised to facilitate coupling to the CNTs In one embodiment the insect OrX is functionalised with a his-tag.

Therefore, in one embodiment the OrX comprises a his-tag.

Preferably the his-tag is at the N-terminus of the OrX protein

CNT Functionalisation

In one embodiment CNT is functionalised to facilitate coupling to the the insect OrX In a further embodiment the CNTs are functionalised with nickel (Ni)-nitrilotriacetic acid (NTA)

Coupling

In a further embodiment the OrX is coupled to the CNTs via his-tag affinity binding.

Thus in one embodiment the his-tagged Orx binds to the Ni-NTA functionalised CNT.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OR changes the electrical source-gain current in the channel of the CNT-FET apparatus of the invention.

Quartz Crystal Microbalance (QCM) Apparatus

Preferably the quartz crystal microbalance (QCM) apparatus comprises:
a) a resonator component
b) an oscillation source component
c) a frequency sensing component Resonator Component In one embodiment the resonator component is, or is composed of, a piezoelectric material, at least one piezoelectric crystal, and at least one quartz crystal. In a preferred embodiment the resonator component is a quartz crystal resonator.

In one embodiment the quartz crystals are coated with gold.

In one embodiment the resonator component has an electrode attached to two of it opposing sides.

In one embodiment the electrodes are composed of, or coated with, gold.

In a preferred embodiment the resonator component is in electrical communication with at least one insect OrX Oscillation Source Component In one embodiment the oscillation source component is configured to apply an alternating electric field to the resonator component.

In one embodiment alternating electric field is applied via the electrodes attached to opposing sides of the resonator component.

Frequency Sensing Component

In one embodiment the frequency sensing component is configured to measure the oscillation frequency of the resonator component. In one embodiment the frequency sensing component is configured to measure changes in the oscillation frequency of the resonator component.

Presentation of the Insect OrX

In a further embodiment the OrX is present in a form that is capable of undergoing a conformational change in response to interaction with the analyte.

In one embodiment the insect OrX is present in a membrane mimic.

A membrane mimic, as the name suggests, mimics a natural membrane, and can support the receptor in a confirmation the same as, or similar to, that found in vivo.

The membrane mimic may be selected from a liposome, an amphipole, a detergent micelle, a nanovesicle, a lipid bilayer, and a nanodisc.

Preferably the membrane mimic is artificial.

In a preferred embodiment the membrane mimic is a liposome.

In a further embodiment the membrane mimic is a lipid bilayer.

In a further embodiment the membrane mimic is an artificial lipid bilayer.

Methods for reconstituting insect receptors in liposomes are known in the art[14].

Formation of a Lipid Bilayers Comprising the Insect OrX on the Resonator Component Without wishing to be bound by theory, the applicants postulate that in some embodiments when the insect OrXs in liposomes, are applied to the working electrode, the liposome changes structure to form a lipid bilayer on the resonator component. The applicants postulate that the insect OrXs are embedded in the lipid bilayer in similar or same conformation as found in cell membranes in vivo, such that the ligand/analyte binding domain of the receptor of the accessible to the ligand/analyte.

Without wishing to be bound by theory, the applicants postulate that in other embodiments the liposomes remains as liposomes when bound to the working electrode. This is exemplified in FIG. 21.

Linker for QCM

In a further embodiment the insect OrX is coupled to the resonator component via a linker.

In one embodiment the linker molecule is short enough to allow electrical communication between the OrX and the resonator component.

In a further embodiment the linker molecule is short enough to prevent isolation of the resonator component from the receptor.

In a further embodiment the linker molecule is selected from 16-mercaptohexadecanoic acid (16-MHDA), 6-mecaptohexadecanoic acid (6-MHDA) and 6-mercaptohexanoic acid (MHA).

In a preferred embodiment the linker is 6-mercaptohexanoic acid (MHA).

In a further embodiment linker is part of a Self-Assembled Monolayer (SAM).

Thus in one embodiment the SAM layer is composed 6-mercaptohexanoic acid (MHA).

In a further embodiment activation of the carboxylic groups of the MHA is performed prior to coupling of the insect OrX.

Preferably, activation of the carboxylic groups of the MHA is performed using a solution of 1-ethyl-3-(3-dimethyl amino propyl) carbodiimide (EDC) and N-hydroxysuccinimide (NHS), prior to coupling the insect OrX to the electrode.

Detection of Analyte

In a further embodiment the sensor is capable of detecting binding of an analyte to the insect OrX.

In a further embodiment the sensor is capable of detecting in an environment the presence of an analyte that binds to the insect OrX.

Preferably detection of the analyte is specific.

In a further embodiment binding of the analyte to the insect OrX changes the resonance frequency of the resonator component induced by an alternating electric field applied to the resonator component.

Sensitivity of Detection

As discussed above, the sensor of the invention works surprising well. The applicants have shown that the sensor device of the invention is considerably more sensitive than any of known assay involving use of insect ORs.

In one embodiment the sensor can detect the presence of the analyte at a concentration of less than $1\times10^{-3}$M, preferably less than $1\times10^{-3}$M, more preferably less than $1\times10^{-4}$M, more preferably less than $1\times10^{-5}$M, more preferably less than $1\times10^{-6}$M, more preferably less than $1\times10^{-7}$M, more preferably less than $1\times10^{-8}$M, more preferably less than $1\times10^{-9}$M, more preferably less than $1\times10^{-10}$M, more preferably less than $1\times10^{-11}$M, more preferably less than $1\times10^{-12}$M, more preferably less than $1\times10^{-13}$M, more preferably less than $1\times10^{-14}$M, more preferably less than $1\times10^{-15}$M, more preferably less than $1\times10^{-16}$M, more preferably less than $1\times10^{-17}$M, more preferably less than $1\times10^{-18}$M.

Dynamic Range

In one embodiment the sensor has a dynamic range for detection of anylate of at least 2, preferably at least 3, more preferably at least 4, more preferably at least 5, more preferably at least 6, more preferably at least 7, more preferably at least 8, more preferably at least 9, more preferably at least 10 orders of magnitude of analyte concentration.

Lack of Orco in the Sensor Device

All previously known systems/assays using insect odorant receptors utilise the combination of the insect OrX and the odorant co-receptor (Orco). This indicates a very strong bias in the prior art for the requirement of both the OrX and Orco components in order to produce an insect odorant receptor (OR) complex with OrX/Orco in the appropriate combination that is capable specifically binding cognate ligand and transducing a response to binding of the ligand.

As previously discussed insect OR complexes (of Orco and OrX) form ligand gated ion channels, and it is transport of ions through the ion channel that transduces the signal in vivo, and presumably in the sensor systems/assays of the prior art.

Thus a further and highly surprising feature of the present invention is the capability of the sensor of the invention to detect ligand/analyte binding in the absence of the Orco co-receptor.

In one embodiment the sensor comprises less than a 10:1, preferably less than a 1:1, preferably less than a 0.1:1, preferably less than a 0.01:1, preferably less than a 0.001:1, preferably less than a 0.0001:1, preferably less than a 0.00001:1 ratio of OrX:Orco.

In a preferred embodiment the sensor does not include an insect odorant co-receptor (Orco).

Other Advantages of the Sensor of the Invention

The sensor or the invention provides numerous further potential advantages over previously known insect OR based systems/assays in terms of convenience, portability, stability, rapid detection, sensitivity, and ease of measurement.

Analyte Medium

The analyte may be in a gaseous or liquid medium.

Optional Capture Component

The sensor device may additionally comprise a component to capture the anaylte and present the analyte to the receptor. This component may be useful for capturing volatile analytes in some embodiments for presentation to the OrX. This may involve us of microchannels to handle the target VOC either in a liquid or gaseous phase ([50]). Microfluidic systems have been designed to deliver target molecules to sensor surfaces in the liquid ([51, 52]) and the gaseous phase ([53, 52, 54]).

Multiplexing

The invention contemplates multiplex approaches using multiple different OrX proteins. proteins. In this way, the user may construct a multiplexed device that is sensitive to multiple analytes. Such multiplexed devices may include tens, hundreds, or even thousands of sensors as herein described. A multiplex device may also include two or more sensors that are coupled to the same OrX so as to introduce a double-check into the device.

The invention also contemplates use of chips with multiple sensor substrates each comprising a different or the same receptor. The sensor device component of the invention may be such a chip.

Method Using Sensor Device of the Invention

The invention provides methods of use of the sensor device of the invention to detect an analyte, and/or the presence of analyte in an environment, as described above.

Controls and Calibration

The user may compare the electrical characteristic of the device to a corresponding electrical characteristic measured when the device is exposed to a control, a known analyte, or both. The user may also generate an estimate of the presence of one or more analytes in the sample. This may be accomplished by comparing the electrical characteristic observed in a sample to a calibration curve of that electrical characteristic that corresponds to data points gathered from a control or standard having a known amount of an analyte of interest. In this way, the user may estimate the concentration of an analyte present in a sample to which the device has been contacted.

The user may construct a library of one or more electrical characteristics of the device that correspond to the device's exposure to one or more known analytes. For example, a user may construct a library of results that represents the electrical characteristic observed when a device is exposed to various concentrations of analytes.

Method of Manufacturing the Sensor Device of the Invention

Sensor Device

In a further aspect the invention provides a method of manufacturing a sensor device the method including the step of establishing electrical communication between an insect OrX and the substrate of the sensor device, wherein the sensor device is configured to detect a change in an electrical characteristic of the substrate.

In one embodiment the method includes the step of coupling of the insect OrX to the substrate.

In one embodiment the OrX is coupled to the substrate before the OrX coupled substrate is assembled in the sensor device.

Preferably the components, coupling and functionality of the sensor is/are as described herein.

Sensor Component

In a further aspect the invention provides a method for producing a component for a sensor device, the component comprising an OrX in electrical communication with a substrate as herein defined. The method comprises establishing electrical communication between the OrX and the substrate, as described herein. This component is useful for adding to a sensor device according to the invention.

In a further embodiment the invention provides a method for producing a sensor device, the method comprising adding the component to other components, as herein described, to produce a sensor device according to the invention.

Method of Manufacturing the EIS Sensor Device of the Invention

In embodiment the substrate is the working electrode of an electrochemical cell as described herein.

Thus in one embodiment method comprises the step of establishing electrical communication between an insect OrX and the working electrode of an electrochemical cell, wherein electrochemical cell is configured to detect a change in the electrochemical impedance of the working electrode thus forming the sensor device.

By way of example a suitable method for manufacture of the EIS device of the invention is described in Example section. This example is not intended to limit the scope of the invention.

Method of Manufacturing the CNT-FET Sensor Device of the Invention

In embodiment the substrate is the channel of an of an CNT-FET apparatus as described herein.

Thus in one embodiment method comprises the step of establishing electrical communication between an insect OrX and the channel of an of an CNT-FET apparatus, wherein the channel of an of an CNT-FET apparatus is configured to detect a change in the source-gain current of the CNT-FET apparatus thus forming the sensor device.

By way of example a suitable method for manufacture of the CNT-FET device of the invention is described in Example section. This example is not intended to limit the scope of the invention.

Method of Manufacturing the QCM Sensor Device of the Invention

In embodiment the substrate is the resonator component of a quartz crystal microbalance (QCM) as described herein.

Thus in one embodiment method comprises the step of establishing electrical communication between an insect OrX and the resonator component of a quartz crystal microbalance (QCM), wherein QCM is configured to detect a change in the the resonance frequency of oscillations induced by an alternating electric field applied to the resonator component, thus forming the sensor device.

By way of example a suitable method for manufacture of the QCM device of the invention is described in Example section. This example is not intended to limit the scope of the invention.

General Definitions and Methods

OrX Proteins/Polypeptides and Fragments

The term "polypeptide", as used herein, encompasses amino acid chains of any length but preferably at least 5 amino acids, including full-length proteins, in which amino acid residues are linked by covalent peptide bonds. Polypeptides for use in the present invention are preferably produced partially or wholly using recombinant or synthetic techniques.

A "fragment" of a polypeptide is a subsequence of the polypeptide that preferably performs a function of and/or provides three dimensional structure of the polypeptide.

A "functional fragment" of an OrX polypeptide is a subsequence of an OrX that can perform the function of binding an analyte, and undergoing a conformational change in upon anylate binding, wherein the conformational change results in a change in an electrical property of a substrate to which the functional fragment is bound.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

Variants

A variant of an OrX polypeptide refers to polypeptide sequences different from the specifically identified sequences, wherein one or more amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the identified polypeptides possess biological activities that are the same or similar to those of the inventive polypeptides or polypeptides. Preferably a OrX polypeptide variant can perform the function of binding an analyte, and undergoing a conformational change in upon anylate binding, wherein the conformational change results in a change in an electrical property of a substrate to which the functional fragment is bound.

Variant polypeptide sequences preferably exhibit at least 70%, more preferably at least 80%, more preferably at least 90%, more preferably at least 95%, more preferably at least 96%, more preferably at least 97%, more preferably at least 98%, and most preferably at least 99% identity to a sequences of the present invention. Identity is preferably calculated over the entire length of an identified polypeptide.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp://ftp.ncbi.nih.gov/blast/.

Polypeptide sequence identity may also be calculated over the entire length of the overlap between a candidate and subject polynucleotide sequences using global sequence alignment programs. EMBOSS-needle (available at http:/www.ebi.ac.uk/emboss/align/) and GAP (Huang, X. (1994) On Global Sequence Alignment. Computer Applications in the Biosciences 10, 227-235) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-405)

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Methods for Producing Polypeptides

The polypeptides used in the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco California, or automated synthesis, for example using an Applied Biosystems 431A Peptide Synthesizer (Foster City, California). Mutated forms of the polypeptides may also be produced during such syntheses.

Preferably, the polypeptides and variant polypeptides, are expressed recombinantly in suitable host cells and separated from the cells as discussed below. Polynucleotides, for expressing the polypeptides, can be conveniently synthesised by methods well known to those skilled in the art. The polynucleotide sequences may be naturally occurring, or may be adapted from naturally occurring sequences, for example through use of preferred codon usage for the cell in which the sequence sequence is recombinantly expressed.

Methods for Producing Constructs and Vectors

The genetic constructs for use in invention comprise one or more polynucleotide sequences encoding OrX polypeptides for use in the the invention, and may be useful for transforming, for example, bacterial, fungal, insect, mammalian or plant organisms.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors Host cells comprising polynucleotides are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides for use in the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE FIGURES

The present invention will be better understood with reference to the accompanying non-limiting drawings in which.

EXAMPLES

Figure 1:
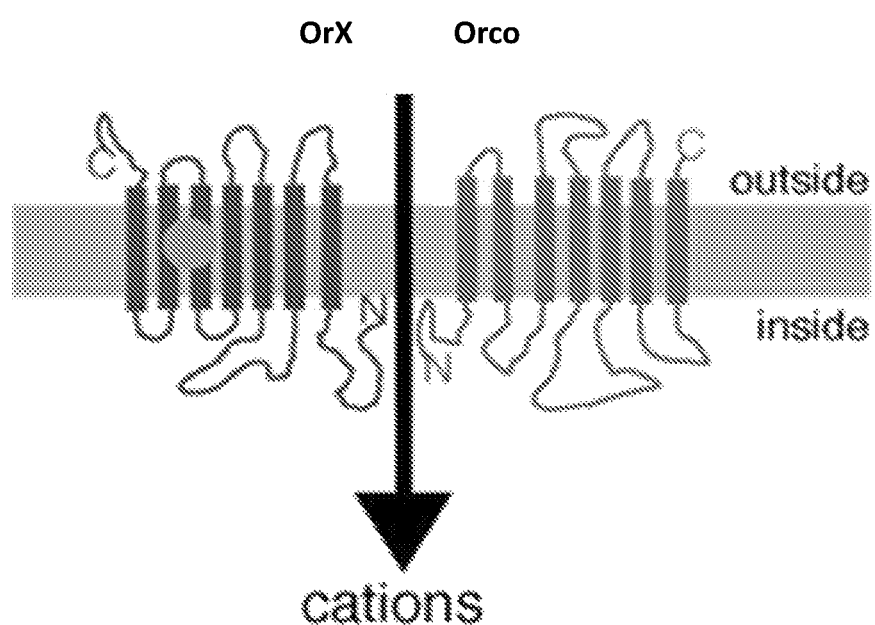
FIG. 1. Schematic representation of the insect OR membrane complex, comprised of an odorant binding OrX subunit and an Orco subunit to produce a ligand-gated non-selective cation channel. The orange circle represents the bound odorant.

The invention will now be illustrated with reference to the following non-limiting example.

It is not the intention to limit the scope of the invention to the abovementioned example only. As would be appreciated by a skilled person in the art, many variations are possible without departing from the scope of the invention.

Example 1

Exemplification of the Sensor of the Invention with Electrical Impedance Spectroscopy (EIS)

1.0 Experimental Methods 1.1 Materials

N-(3-dimethylaminopropyl)-N'-ethylcarbodiimide (EDC), N-hydroxysuccinimide (NHS), phosphate buffered saline (PBS) pellets, 6-Mercaptohexanoic acid (MHA), dimethyl sulfoxide (DMSO) were purchased from Sigma Aldrich. All aqueous solutions were prepared with distilled water (Milli-Q 18.2 MΩ), filtered through Microscience Hydraflon filters (0.22 μm) and flushed with $N_2$ for 10 minutes unless otherwise stated. 1.6 mm gold (Au) disk electrodes, platinum (Pt) spiral auxiliary electrode and Ag/AgCl reference electrode were purchased from BASI.

1.2 Preparation of Liposome Associated OR Subunits

Liposomes were prepared using a phospholipid solution produced by evaporating solutions containing: phosphatidylethanolamine (PE), phosphatidylserine (PS), phosphatidylcholine (PC), and cholesterol (CH) at a molar ratio of 5:3:3:1 in a small glass tube under a stream of $N_2$ gas, then desiccating under vacuum for 1 h.

These lipids were resuspended in 1 mL of rehydration buffer (10 mM HEPES pH 7.5, 300 mM NaCl) by vortexing for 5 min followed by sonicating on a Microson ultrasonic cell disrupter (Medisonic, USA) five times at 20% power for 10-20 s, placing the sample on ice between each sonication step for 1 min. To promote the formation of liposomes, 10 freeze/thaw steps were performed by transferring the tube from liquid nitrogen to a 40° C. water bath.

Liposomes were then sized by passing the lipid solution 11 times through a 100-nm polycarbonate membrane using an Avestin LiposoFAST extruder unit (Avestin, Germany). Glycerol was added at 10% of the final volume and aliquots at 10 mg/mL were snap frozen in liquid nitrogen and stored at −80° C.

Purified OR subunits[43] were reconstituted into the synthetic liposomes in a similar manner to the protocol of Geertsma et al. (2008)[34].

Prior to their use, liposomes were defrosted on ice and then destabilized by incubating with 0.2% CHAPS for 15 min at room temperature. Then 200 µg of purified odorant receptor[14] was added to 1 mg of liposomes and rotated at 10 rpm for 1 h at room temperature. Excess detergent was removed by four additions of 25 mg of Bio-Beads SM-2 (Bio-Rad, USA) and incubation at 4° C. for 30 min, 2 h, overnight and a further 2 h respectively. The Bio-Beads were removed after each incubation period. The OR integrated liposomes were pelleted by centrifugation at 100,000 g for 1 h, and were resuspended in 500 µL of rehydration buffer. Integration of OrXs into liposomes was assessed by density gradient ultracentrifugation (DGU) using Accudenz (Accurate Chemical & Scientific Corporation, USA). The integrated liposomes were brought to 40% Accudenz by the addition of an equal volume of 80% Accudenz solution, placed at the bottom of an ultracentrifugation tube, and overlaid with 30% Accudenz solution, and DGU buffer (25 mM HEPES pH 7.5, 100 mM NaCl, 10% glycerol). The sample was then centrifuged at 100,000 g for 4 h at 4° C. Liposomes will float to the top of the gradient after Accudenz DGU due to their low density. 1.3 Electrode Cleaning Gold disk (2 mm) electrodes were cleaned with polishing with Alumina paste for 2 minutes, ultra-sonicated in pure ethanol and then Milli-Q water for 5 minutes each. Then, for thiol desorption, −1.4 V applied for 30 seconds each in 0.1M NaOH in a 3 terminal electrochemical cell. Electrodes were again polished with Alumina paste for 2 minutes, ultra-sonicated in pure ethanol and then Milli-Q water for 5 minutes each. Any remaining organic molecules were cleaned via cycling in 0.5M $H_2SO_4$ for 5 cycles between −0.2 and 1.6V at 50 mV/sec scan rate.

1.4 Self-Assembled Mono Layer (SAM) Preparation and Activation

The cleaned electrodes were immersed into a 2 mM ethanolic solution of 6-mercaptohexanoic acid (MHA) overnight. After that, electrodes were treated with absolute ethanol and Milli-Q water.

Activation of the carboxylic groups of the MHA was performed by incubating electrodes in a PBS (pH:6.5) solution containing a mixture of 100 mM 1-ethyl-3-(3-dimethyl amino propyl) carbodiimide (EDC) and 50 mM N-hydroxysuccinimide (NHS) at 28° C. for 60 minutes.

1.5 Liposome Incubation

Following the —COOH activation, electrodes were incubated in 100 µL of a 1:100 dilution of liposomes in PBS (pH 7.4) at room temperature for 20 minutes. Then they were rinsed gently with excess PBS (pH 7.4).

1.6 Target Odorant Solution Preparation and Incubation

Target solutions were diluted in PBS (pH 7.4) containing 1% DMSO to give concentrations of, 128 pM, 640 pM, 3.2 nM, 16 nM, 80 nM, 400 nM and 2 µM. Electrodes were incubated in relevant odorant solutions for 5 minutes each and washed gently with PBS (pH 7.4).

TABLE 1

List of the odorant receptors and relevant positive and negative ligands.

| Odorant receptor | Reference | Known ligand | Control |
|---|---|---|---|
| Or10a | 43 | Methyl salicylate | Methyl hexanoate |
| Or22a | 43 | Methyl hexanoate | Methyl salicylate |
| Or35a | 43 | E2-hexenal | VUUA1 |

1.7 Electrochemical Impedance Spectroscopy (EIS) Measurements

EIS measurements were performed subsequently in a three terminal electrochemical cell comprising a platinum (Pt) wire as counter electrode (CE), Ag/AgCl (3 M KCl, +0.197 V vs. SHE) reference electrode (RE), and 1.6 mm gold disk electrode with liposomes as working electrode (WE) between 100 kHz-0.2 Hz with applying −0.7V against the reference. Charge transfer resistance of the surface decreased following each odorant incubation and stayed unchanged after an addition of 2 µM of odorant.

2.0 Results

Figure 2:
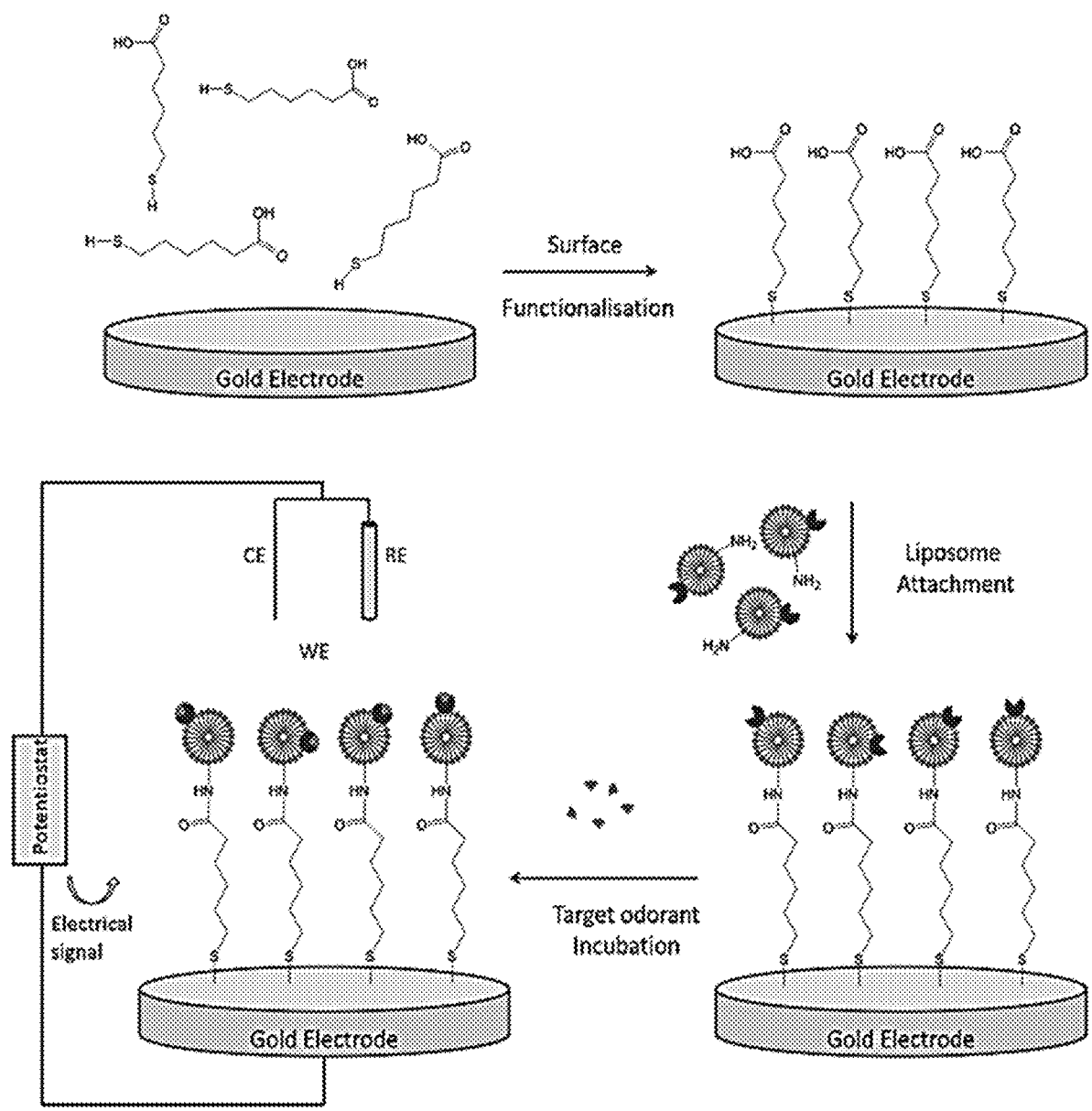
FIG. 2. Schematic representation of sensor preparation starting with electrode cleaning, followed by SAM formation and completed with the covalent attachment of liposomes onto the SAM layer. Electrochemical read-out is obtained from EIS measurements carried out in three terminal electrochemical set-ups. Circles with cut out segments represent liposome-integrated insect OrXs, and small triangles represent VOC ligands.

Clean gold surface was incubated with MHA overnight leading surface functionalisation with —COOH groups. Then liposomes carrying receptors (either Or35a, Or22a or Or10a) were covalently attached to the MHA via NHS-EDC chemistry (FIG. 2). EIS measurements were performed prior and after target (ligand) incubation with increasing concentrations. Receptors and ligands used in this study can be seen in Table 1.

Figure 3:
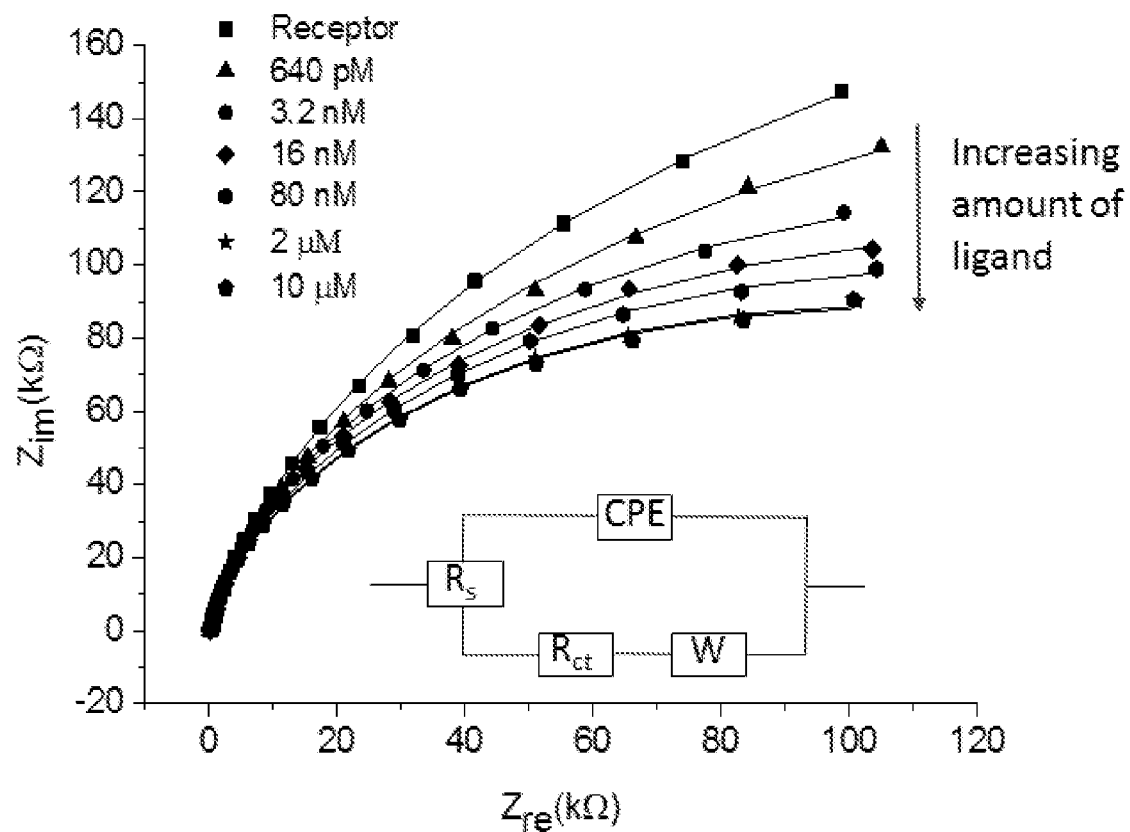
FIG. 3. Impedance evolution of an or35a functionalised electrode versus E2-hexenal with a concentration range from 640 pM to 10 µM. Experimental data are presented as symbols and the equivalent circuit fitting curves as solid lines.

It is expected that receptor-ligand interaction alters the overall surface charge and such changes can be observed with EIS. FIG. 3 represents the impedance spectra evolution led by subsequent ligand (E2-Hexanal) incubation on an electrode functionalised with Or35a. For all type of receptors studied in this paper, impedance of the electrodes decreased upon interaction with increased amount of ligands.

Charge transfer resistance ($R_{ct}$) of electrodes were calculated by fitting obtained data to a Randles' equivalent circuit $[R_s+CPE/(R_{ct}+W)]$ comprising of a solution resistance ($R_s$) in series with a constant phase element (CPE) and in parallel with charge transfer resistance ($R_{ct}$) and Warburg diffusion element. Then obtained values of $R_{ct}$ were normalised to $R^0_{ct}$ ($\Delta R_{ct}$), where $R^0_{ct}$ represents the electrodes prior to ligand incubation. Calibration curves were obtained by defining sensor response as $\Delta R_{ct}/R^0_{ct}$ versus log[C(Ligand)] (FIG. 4).

Figure 4:
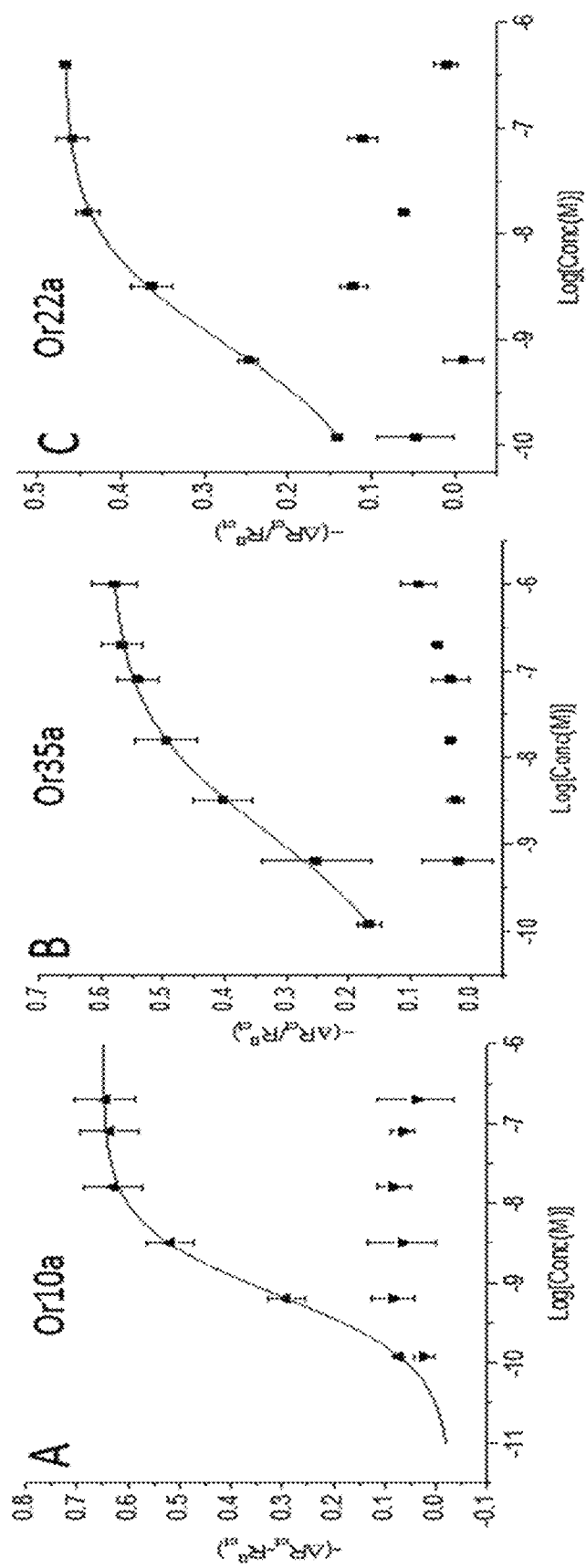
FIG. 4. Dose response curves for A) Or10a incubated in Methyl salicylate, B) Or35a incubated in E2-hexenal and C) Or22a incubated in Methyl hexanoate with a concentration range of 128 pM to 2 µM. Negative controls; Or10a Methyl hexanoate, Or35a VUAA1, Or22a Methyl salicylate, respectively.

FIG. 4 reveals the reproducibility of detection which is highlighted by the relatively small error bars, obtained from 3 repeats (or10a and or35a) and 2 repeats (or22a) of the sensing experiments. Obtained sensors possess extremely low detection limits within the dynamic range of 3-4 orders of magnitude. When signal/background variability (noise) is considered to be $>3^{35-38}$, the lowest detectable concentrations of odorants were calculated to be $3.3 \times 10^{-10}$ M methyl salicylate for Or10a, $3.6 \times 10^{-11}$ M E2-hexenal for Or35a and $2.8 \times 10^{-10}$ M methyl hexanoate for Or22a. These detection limits are considerably lower than previous studies where odorant binding proteins were directly immobilised onto sensor surfaces without using liposomes. For example, in the case of an odorant binding protein (BdorOBP2) which was directly immobilised onto gold substrates, the sensor provided a detection limit of around micromolar ($10^{-6}$ M) for queen pheromone (methy-p-hydroxyl benzoate), alarm pheromone (isoamyl acetate), linalool, geraniol, β-ionone, 4-allylveratrole, phenylacetaldehyde, dibutyl phthalate[39]. In another study, the peptide solution containing a sequence of the *Drosophila* OBP LUSH was again directly immobilised onto gold surface and detection limits of $4.9 \times 10^{-5}$ M for 1-hexanol and $5.6 \times 10^{-5}$ M for 3-methly butanol were achieved[40]. In a recent study, instead of gold, carbon nanotubes were employed as the sensing element and again OBP proteins were directly immobilised without any media[41]. Authors reported that $1.8 \times 10^{-2}$M 2-heptanone and $0.52 \times 10^{-10}$ M TNT could be detected.

Sensitivity of the obtained sensors was calculated by using the slope of the linear range (lowest three concentrations) of each sensor[36, 42, 38] and found to be 0.313 units/[log(conc/M)] for Or10a, 0.116 units/[log(conc/M)] for Or35a and 0.156 units/[log(conc/M)] for Or22a.

3.0 Discussion

The applicants tested different Self-Assembled Mono layers (SAM layers) initially before identifying 6-mercaptohexanoic acid (MHA) as a linker of optimal length to bind the liposomes on to the gold electrode surface. Previously, 16-mercaptohexadecanoic (16-MHDA) acid was used to functionalize the gold surface and bind the liposomes onto the gold electrode. Results from that experiment did not show high sensitivity suggesting the liposomes were too far away from the electrode surface to give a detectable signal. To overcome that obstacle the applicants used the shorter 6-mercaptohexanoic acid instead. The applicants postulated that this linker being shorter would provide faster electron transfer between gold and liposomes, thus, any event occurring on the surface can be monitored in a more sensitive fashion. In the case of the two papers which immobilised mammalian odorant receptors in crude cell membranes, they used either 16-mercaptohexadecanoic acid (16-MHDA)[34] or 6-mecaptohexadecanoic acid (6-MHDA)[14] for SAM formation.

Comparative data shows that the insect OR-EIS biosensor format as disclosed here is more sensitive than other sensor formats that have been used with insect odorant receptors.

Table 2 summarises the published data on odorant receptor based devices. The present device provides between 100-10,000-fold greater sensitivity than cell-based sensors.

TABLE 2

Comparison of insect odorant receptor sensor device data.

| Sensor/assay approach | Receptor - analyte | Sensitivity limit | $EC_{50}$ | Ref |
|---|---|---|---|---|
| Stable Sf21 cell line on microfluidics chip - fluorescence | BmOR1/Ocro - Bombykol pheromone | $1 \times 10^{-6}$ M | $4.39 \times 10^{-6}$ M | 13 |
| | BmOR3/Orco - Bombykal pheromone | $0.3 \times 10^{-6}$ M | $2.03 \times 10^{-6}$ M | |
| *Xenopus* oocytes on a microfluidics device -two electrode voltage clamping (TEVC) | BmOR1/Orco - Bombykol pheromone | $10^{-8} - 10^{-6}$ M* | $0.25 \times 10^{-6}$ M | 12 |
| | BmOR3/Orco - Bombykal pheromone | $10^{-8} - 10^{-6}$ M* | $0.38 \times 10^{-6}$ M | |
| | PxOR1/Orco - Z11-16:Ald | $10^{-8} - 10^{-6}$ M* | $2.52 \times 10^{-6}$ M | |
| | DOr85b/Orco to 2-heptanone | $10^{-8} - 10^{-6}$ M* | $45.6 \times 10^{-6}$ M | |
| Insect OrX-EIS device | DmOr10a - methyl salicylate | $3.3 \times 10^{-10}$ M | $\sim 10^{-9}$ M | Present study |
| | DmOr22a - methyl hexanoate | $2.8 \times 10^{-10}$ M | $\sim 10^{-8}$ M | |
| | DmOr35a - E2-hexenal | $3.6 \times 10^{-11}$ M | $\sim 10^{-8}$ M | |

*indicates value has been estimated from a visual assessment of dose response data plotted on a graph in the cited reference.

Table 3 summarises data obtained from cell assays. The present insect OrX-EIS sensor data is more sensitive than OrX/Orco expressed in HEK293 cells and *Xenopus oocytes*. Note in these systems some pheromone receptors (PRs) exhibit much lower sensitivity than normal odorant receptors, this is to be expected as these receptors are finely tuned to their pheromone target molecules.

TABLE 3

Overview of insect ORX/Orco cell assay data.

| Sensor/assay approach | Receptor - Analyte | Sensitivity limit | Ec50 | Ref |
|---|---|---|---|---|
| Insect Sf9 transient cell assay | EpOR1/Orco - geraniol | $10^{-14}$ M* | $1.8 \times 10^{-12}$ M | 17 |
| Insect Sf9 transient cell assay | EpOR3/Orco - Citral | $10^{-15}$ M* | $1.1 \times 10^{-13}$ M | 17 |
| Insect Sf9 transient cell assay | DmOr22a/Orco - ethyl butyrate | $10^{-12}$ M* | $1.58 \times 10^{-11}$ M | 3 |
| Insect Sf9 transient cell assay | BmOr19/Orco - linalool | $10^{-10}$ M* | $4.69 \times 10^{-9}$ M | 18 |
| Insect Sf9 transient cell assay | BmOr45/Orco - benzoic acid | $10^{-11}$ M* | $1.44 \times 10^{-10}$ M | 18 |
| Insect Sf9 transient cell assay | BmOr47/Orco - benzoic acid | $10^{-14}$ M* | $1.42 \times 10^{-11}$ M | 18 |
| Insect Sf9 transient cell assay | Am151/Orco - Floral mixture | $10^{-10}$ M* | $1.54 \times 10^{-9}$ M | 4 |
| Insect Sf9 transient cell assay | Am152/Orco - Floral mixture | $10^{-10}$ M* | $6.55 \times 10^{-9}$ M | 4 |
| HEK293 stable cell assay | EpOR3/Orco - geranyl acetate | | $1.0 \times 10^{-6}$ M | 19 |
| HEK293 stable cell assay | ApolOR1/Orco - (+ApolPBP2, (E,Z) -6,11-hexadecadienal: pheromone) | $10^{-15}$ M* | $10^{-13}$ M? | 20 |
| HEK293 stable cell assay | HR13/Orco - PBP2 (+ pheromone) | $10^{-13}$ M | 200 fM | 21 |
| HEK293 stable cell assay | HR13/Orco- DMSO (+ pheromone) | $10^{-10}$ M | 1.2 nM | 21 |
| HEK293 stable cell assay | BmOR-1/Orco - PBP (+ pheromone) | $10^{-12}$ M | | 22 |
| HEK293 stable cell assay | DmOr22a/Orco - methyl hexanoate | Log = −7.5* | Log = −6.38 | 23 |
| HEK293 stable cell assay | AgOr65/Orco - eugenol | Log = −7* | Log = −6.54 | 23 |
| HEK293 stable cell assay | DmOr22a/Orco - methyl hexanoate) | Log = −7* | $1.17 \times 10^{-6}$ M | 24 |
| HEK293 stable cell assay | AgOr48/Orco - g-dodecalactone) | Log = −8* | Log = −7.01 | 25 |
| *Xenopus* oocytes | ECB (Z) OR3/Orco - E11 pheromone | $10^{-9}$ M | $12.5 \times 10^{-9}$ M | 2 |
| *Xenopus* oocytes | ACB OR3/Ocro - E12 pheromone | $1 \times 10^{-9}$ M | $7 \times 10^{-9}$ M | 2 |
| *Xenopus* oocytes | SexiOR13/Orco - Z9, E12-14:OAc pheromone. | | $3.158 \times 10^{-6}$ M | 26 |
| *Xenopus* oocytes | SexiOR16/Orco - Z9-14:OH pheromone. | | $9.690 \times 10^{-7}$ M | 26 |
| *Xenopus* oocytes | OscaOR1/Orco - E11-14:OH pheromone. | $10^{-7}$ M* | $10^{-6}$ M | 27 |
| *Xenopus* oocytes | MsiOR1/Orco - Z11-16:Ac pheromone | $10^{-7}$ M* | $10^{-6}$ M | 28 |
| *Xenopus* oocytes | DiOR1/Orco - EI1-16:Ald pheromone | $10^{-7}$ M* | $10^{-6}$ M | 28 |
| *Xenopus* oocytes | BmOr1/Orco - bombykol pheromone | | $34 \times 10^{-6}$ M | 29 |
| *Xenopus* oocytes | BmOr1/Orco - bombykol pheromone | | $5.9 \times 10^{-6}$ M | 30 |
| *Xenopus* oocytes | HVOR6/Orco - Z9-14:ald pheromone | | $9.79 \times 10^{-7}$ M | 31 |
| *Xenopus* oocytes | HVOR13/Orco - Z11-16:ald pheromone | | $9.79 \times 10^{-7}$ M | 31 |
| *Xenopus* oocytes | OnOr1/Orco- E12-14:OAc pheromone | | $2.6 \times 10^{-7}$ M | 32 |
| *Xenopus* oocytes | AgOR1/Orco - 4-methylphenol | | $4.12 \times 10^{-7}$ M | 33 |
| *Xenopus* oocytes | AgOR2/Orco - indole | | $1.67 \times 10^{-8}$ M | 33 |
| *Xenopus* oocytes | AgOR8/Orco - 1-octen-3-ol | | $1.86 \times 10^{-7}$ M | 33 |

TABLE 3-continued

Overview of insect ORX/Orco cell assay data.

| Sensor/assay approach | Receptor - Analyte | Sensitivity limit | Ec50 | Ref |
|---|---|---|---|---|
| Xenopus oocytes | AgOr10/Orco - indole | | $1.37 \times 10^{-7}$ M | 33 |
| Xenopus oocytes | AgOr65/Orco - eugenol | | $3.44 \times 10^{-8}$ M | 33 |

*indicates value has been estimated from a visual assessment of dose response data plotted on a graph.

Example 2

Exemplification of the Sensor of the Invention with a Carbon Nanotube-Field Effect Transistor (CNT-FET)

1. Summary

The applicants have produced a convenient, sensitive sensor device using insect OrX sequences. *Drosophila melanogaster* OR35a[43] insect OrX receptors embedded in nanodiscs [55,56] were functionalized on the CNT FETs via 1-pyrenebutanoic acid succinimidyl ester (PBASE) and polyhistidine functionalization. The CNT FETs have shown a clear electronic response to the target ligand E-2-hexenal in real time current measurement mode starting at 1 fM concentration. The specificity of the binding is verified by testing the OR35a functionalized CNT FETs response to control materials, PBS and methyl hexanoate. To further ensure the specificity the response of pristine CNT FET and empty nanodisc functionalized CNT FETs to E-2-hexenal are also tested.

2. Experimental Methods 2.1 Carbon Nanotube Transistor Device Fabrication

Figure 5:
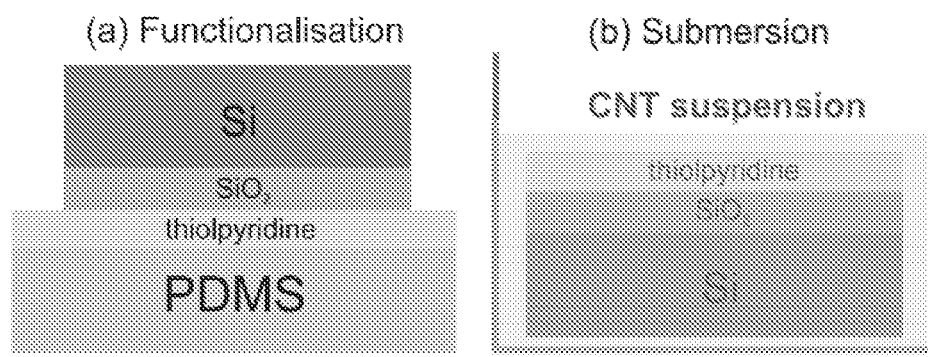
FIG. 5. Schematic representation of CNT deposition process: (a) $SiO_2$/Si is functionalized with 2-thiol-pyridine via a polydimethylsiloxane (PDMS) stamping method. (b) 2-thiol-pyridine functionalized CNT FET is submerged in the premade CNT DCB suspension.

To fabricate carbon nanotube field effect transistor (CNT FET) sensor platforms CNTs are first deposited on $SiO_2$/Si substrates ($SiO_2$=100 nm) using a solution deposition route with no surfactants.[58, 59] A sharp tweezer tip amount of CNTs bucky paper (99.9% IsoNanotube-S from NanoIntegris) is dispersed in dichlorobenzene (DCB) via sonication for one hour. The $SiO_2$ substrates are functionalized with a thin layer of 2-thiol-pyridine (Sigma aldrich) via a polydimethylsiloxane (PDMS) stamping method,[58, 59] as shown in FIG. 5(a). The 2-thiol-pyridine functionalized $SiO_2$/Si substrates are then submerged in the CNT DCB suspension for times ranging from 30 minutes up to 6 hours as shown in FIG. 5(b)[58, 59]. The submersion time allows us to control the CNT thin film network morphology. The substrates are removed from the CNT suspension and cleaned in ethanol and dried in clean $N_2$. The result is a uniform thin film CNT network covering the entire substrate surface.

Figure 6:
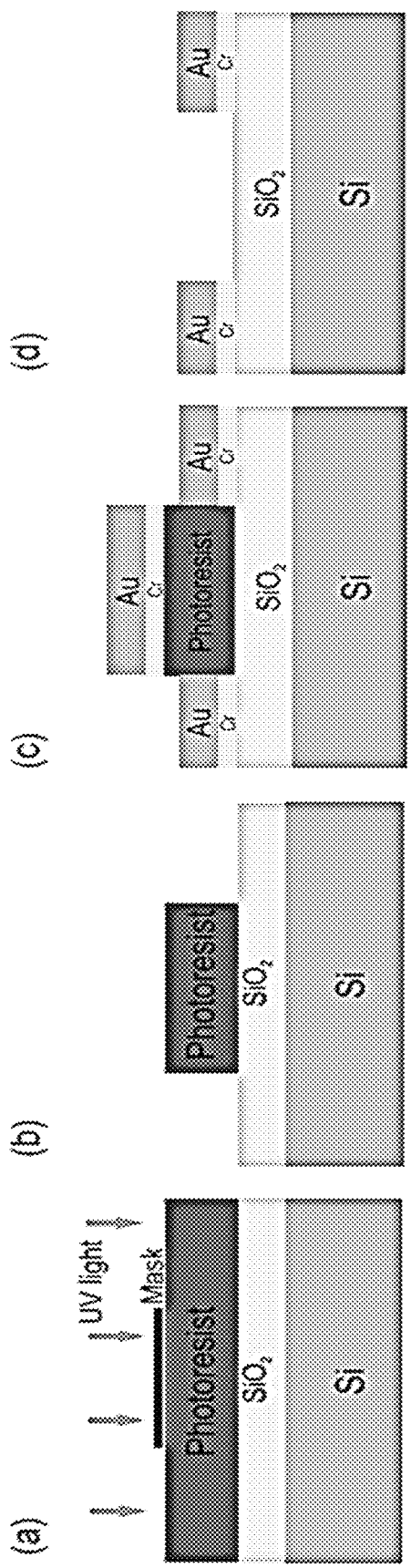
FIG. 6. Electrodes are fabricated on a CNT film coated substrate after a standard microelectronic fabrication: (a) Bring a mask to substrate before exposure under UV light; (b) Post developing in AZ326 developer; (c) Metal deposition by thermal evaporation; (d) Post lift-off in acetone.

As the entire substrate is coated with CNTs it is then essential to control the locations of the CNTs that will form the active channels of the FET devices. To do so the CNT films are coated with photoresist before being patterned at controlled locations using optical lithography. The photoresist coated CNTs form the protected CNT FET channel regions. Reactive ion etching (Oxford Instruments Plasmalab 80) is then used to etch off the exposed CNTs. The etch conditions are 600 mTorr, 200 watts, 40 sccm $O_2$ flow and etch time 3 minutes. This results in areas of the CNT thin films of 100 μm (length) by 100 μm (width) remaining at controlled locations. The source and drain electrodes are then defined by a second photolithography step followed by evaporation of the Cr/Au (5 nm/50 nm) electrodes and lift-off. The process is presented schematically in FIG. 6.

Figure 7:
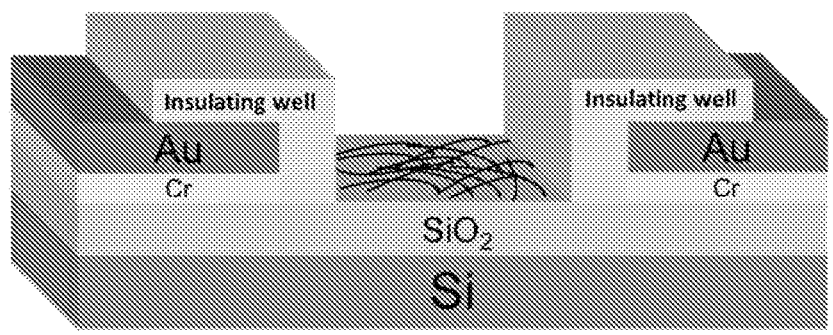
FIG. 7. Schematic of CNT FET structure after electrodes are encapsulated by photoresist as an insulating well.

Finally, electrodes are encapsulated with AZ1518 photoresist by photolithography to act as an electrically insulating well, which prevents electrical leakage currents and electrode damage during sensing experiments, FIG. 7.

Figure 8:
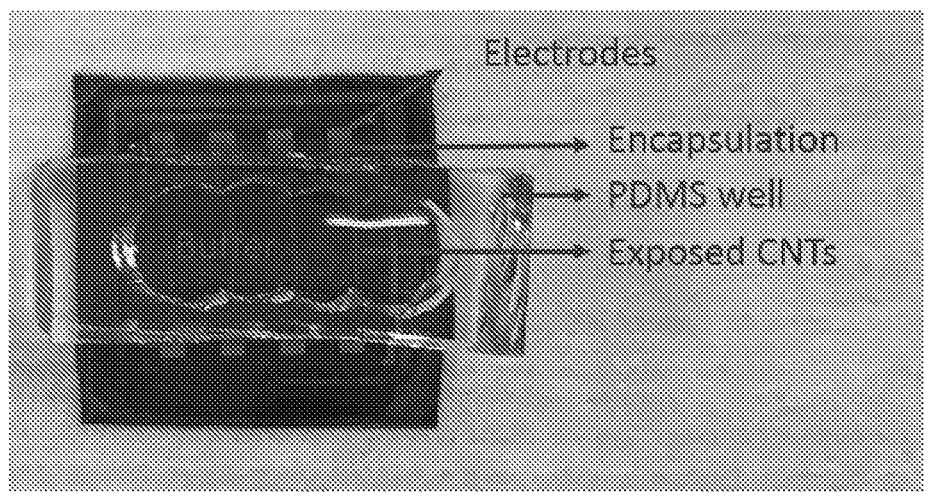
FIG. 8. Photograph image of a handmade PDMS well on the top of anAZ1518 encapsulated CNT FET device.

After the electrode encapsulation, the exposed CNT area becomes 100 μm (width) by 10 μm (length), and this is ultimately the active sensing region of the devices[20]. The photoresist encapsulated CNT FET devices are then baked on a 200° C. hot plate for 10 minutes and gradually cooled down to room temperature. A handmade polydimethylsiloxane (PDMS) well, as shown in FIG. 8, is then permanently attached to the substrate for the CNT FET functionalization and the electrical testing.

2.2 Olfactory Receptor Immobilization 2.2.1 Non-Covalent Functionalisation of Carbon Nanotubes In order to immobilize olfactory receptors on the CNT surfaces without damaging the electronic properties of the CNTs, a non-covalent functionalisation route is chosen. The OrX functionalisation is via a his-tag chemical reaction, where the CNT surfaces are initially functionalized with 1-pyrenebutanoic acid succinimidyl ester (PBASE) (95% purity, Sigma Aldrich). The PBASE solution is made at 10 mM concentration in dimethyl sulfoxide (DMSO) solvent and is stirred at 1600 rpm for 30 s until the PBASE is completely dissolved in DMSO. 120 μl of PBASE solution is added to the PDMS testing well for an hour at room temperature. After PBASE functionalization, to wash off excess PBASE, CNT FETs are cleaned in pure DMSO solvent three times. To remove residual DMSO from the device substrates the samples are washed three times in phosphate buffer saline (PBS, pH=7.4).

2.2.2 Nitrilotriacetic Acid Functionalization

The PBASE functionalized CNT FETs are then functionalized with nitrilotriacetic acid (NTA, Mw~191.14 g/mol) by submerging into 11.3 mM concentration of NTA solution for 2 hours. The 11.3 mM NTA in PBS is diluted from 100 mM NTA stock solution (stock solution is usually kept at 4° C. fridge when not in use) and 120 μl of NTA solution is added into the PDMS well for functionalization at room temperature. The excess NTA is cleaned by washing in PBS three times followed by soaking in deionized water (DI water, 18.2 Ω·cm) for at least one hour.

2.2.3 Nickel Sulfate Functionalization

The NTA functionalized CNTs are incubated in 11.3 mM nickel sulphate ($NiSO_4$, Mw~154.76 g/mol) solution for 30 minutes. The 11.3 mM $NiSO_4$ in PBS is diluted from 100 mM $NiSO_4$ stock solution (stock solution is kept at 4° C. fridge when not in use). 120 μl of $NiSO_4$ solution is added into the PDMS well for functionalization at room temperature. The excess $NiSO_4$ is removed by washing in PBS three times.

2.2.4 Olfactory Receptor Functionalization

OR/nanodiscs[55, 56] are immobilized on Ni-NTA functionalized CNT FETs via his-tag affinity binding. To prepare the nanodisc solution, the bulk OrX/nanodisc solutions are diluted in PBS buffer at either 1:10 or 1:100 dilution. To make 1:10 dilution, 10 μl of stock nanodisc solution is added into 100 μl of PBS. To make 1:100 dilution, 1 μl of stock nanodisc solution is added into 100 µl PBS. The OrX/nanodisc stock solution is usually stored in a −80° C. freezer when not in use or stored in a −20° C. freezer for up to one week. Diluted nanodiscs are added into the PDMS well and the entire CNT surface is then soaked in nanodiscs for 30 minutes for functionalization at room temperature. After the functionalization process, excess nanodiscs are cleaned by washing in PBS three times.

2.3 Electrical Measurements

Figure 9:
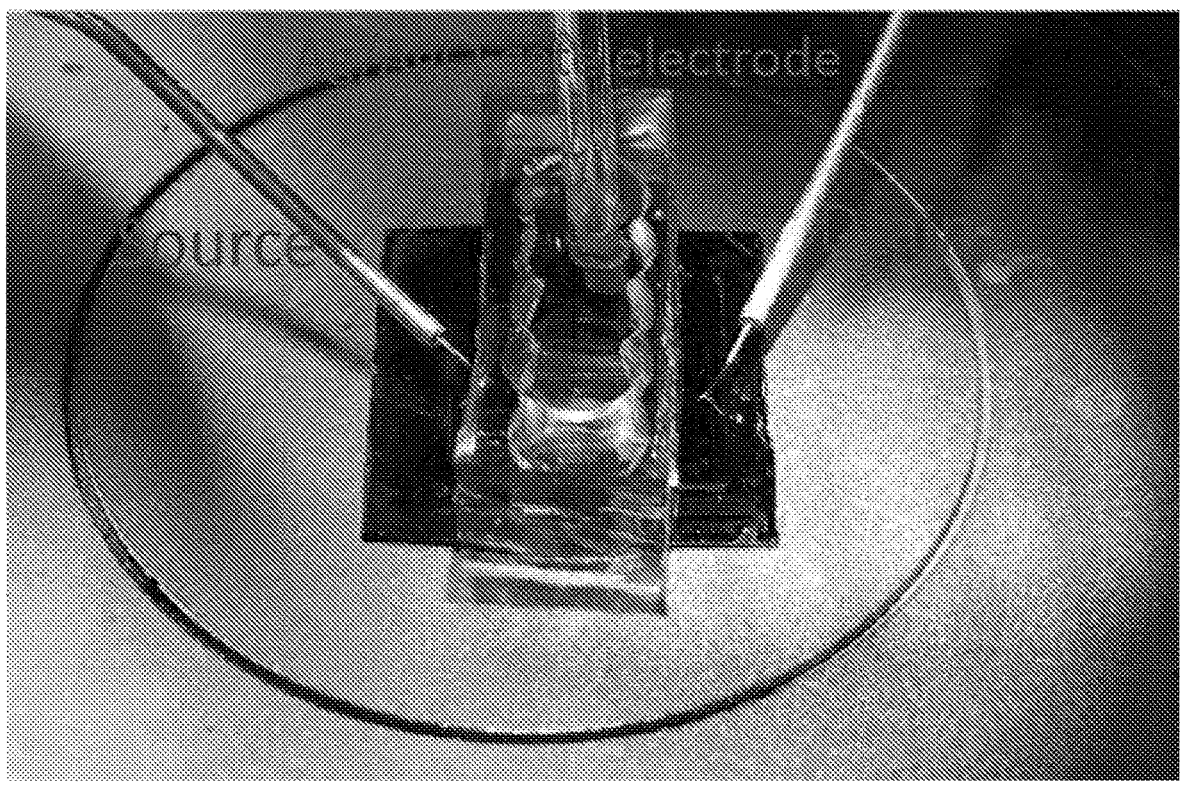
FIG. 9. Sensor set-up for electrical measurement: an Ag/AgCl electrode is inserted into the PBS liquid as the gate electrode. Two probes contacted with electrodes on the CNT FET are the source and drain electrodes.

In order to carry out the electrical measurements the devices were set up with the PDMS well and source, drain and gate electrodes, via micromanipulators and a Rucker and Kolls probe station, as shown in FIG. 9. Before starting the electrical measurements, 100 µl of PBS buffer (containing 1% DMSO) was added into the testing well. The gate electrode is an Ag/AgCl wire (In Vivo Metric) sheathed in plastic where the exposed area at the end of Ag/AgCl was completely inserted into the PBS buffer to avoid any electrical artefacts that are known to occur when changing the active area of the gate electrode. An Agilent 4156C parameter analyser is used for all electrical measurements[20]. The parameter analyser has excellent sensitivity and can accurately measure currents on the femto-amp scale.

During transfer ($V_{lg}$–$I_{ds}$) measurements the gate voltage ($V_{lg}$) is swept between −500 mV to +1 V and the source drain voltage ($V_{ds}$) is set as fixed values (50 mV, 100 mV or 200 mV). For our real time sensing measurement the $V_{lg}$ is set to 0 and $V_{ds}$ is set as fixed values (50 mV, 100 mV or 200 mV, with a time step of 1 s.

2.4 Ligand Dilution

The E-2-hexenal ligand solution is diluted from our 100 mM stock solution, to the concentration ranges required for the sensing experiments. To prepare the stock 100 mM E-2-hexenal in DMSO, we take 5 µl volume of 8.4 M E-2-hexenal (purchased from Sigma Aldrich) and mix in 415 µl of DMSO, and store at 4° C. in the fridge when not in use. To further dilute the solution down to the testing range, PBS buffer is used. The measurement range of E-2-hexenal in PBS (containing 1% DMSO) is 1 fM-1 nM (10 fold increase) or 64 pM-200 nM (5 fold increase). During the real time measurement, PBS solution (containing 1% DMSO) is initially added as a control and the analytes are added additionally with increased concentrations.

Figure 10:
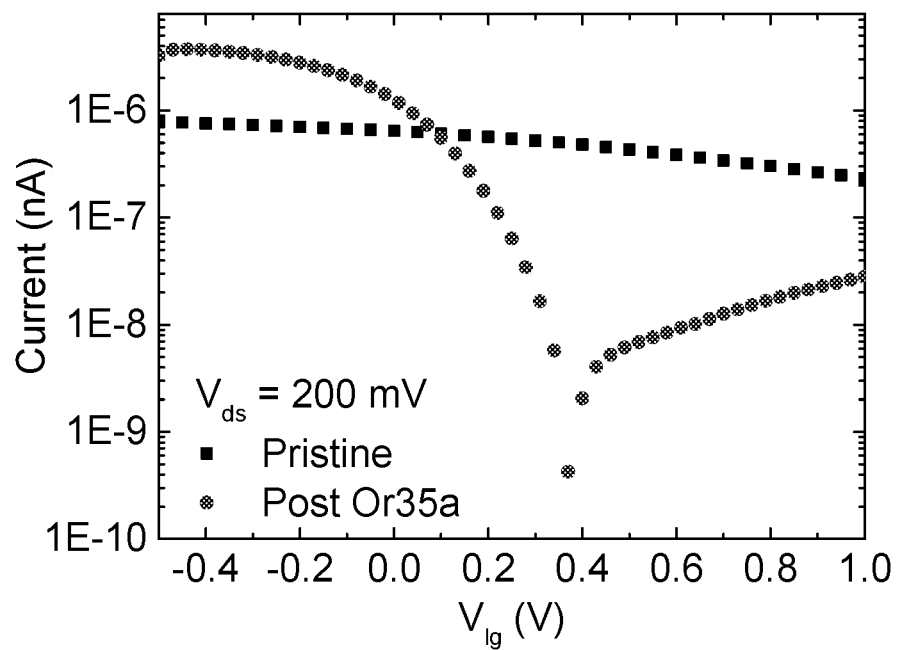
FIG. 10. Transfer characteristics of a pristine CNT FET and the same device after immobilization of Or35a nanodiscs: $V_{ds}$=200 mV, in PBS buffer.

3. Results and Discussion 3.1 Transfer Characteristics of CNT FETs Post OR35a/Nanodiscs Functionalization Before doing sensing measurements the CNT FET transfer characteristics are measured to determine the success of the functionalization process. FIG. 10 compares the OR35a nanodisc functionalized CNT FET (circles) with the pristine CNT FET (squares), where it is clear that the threshold voltage has shifted towards the negative voltage direction after the OR35a nanodisc functionalization. The threshold voltage in the forward I-V scan has shifted from 0.6 V (pristine) to 0.42 V (with OR35a nanodiscs). This is likely due to the electrostatic gating effect from positive charges of $Ni^+$ ($NiSO_4$) as well as the carrier scattered by nanodiscs attached on the sidewall of CNTs[60]. This is evidence of successful immobilization of OrX/nanodiscs, similar to our previous research, when the negative charges of aptamers tethered to the CNTs caused a positive shift in the threshold voltage[58,61]. For CNT FETs successfully functionalized with ORs, the threshold voltage is always shifted in the negative voltage direction.

3.2. OR35a Nanodiscs and Ligand Binding 3.2.1. CNT FETs Functionalized with OR35a Nanodiscs (1:10 Dilution)

Figure 11:
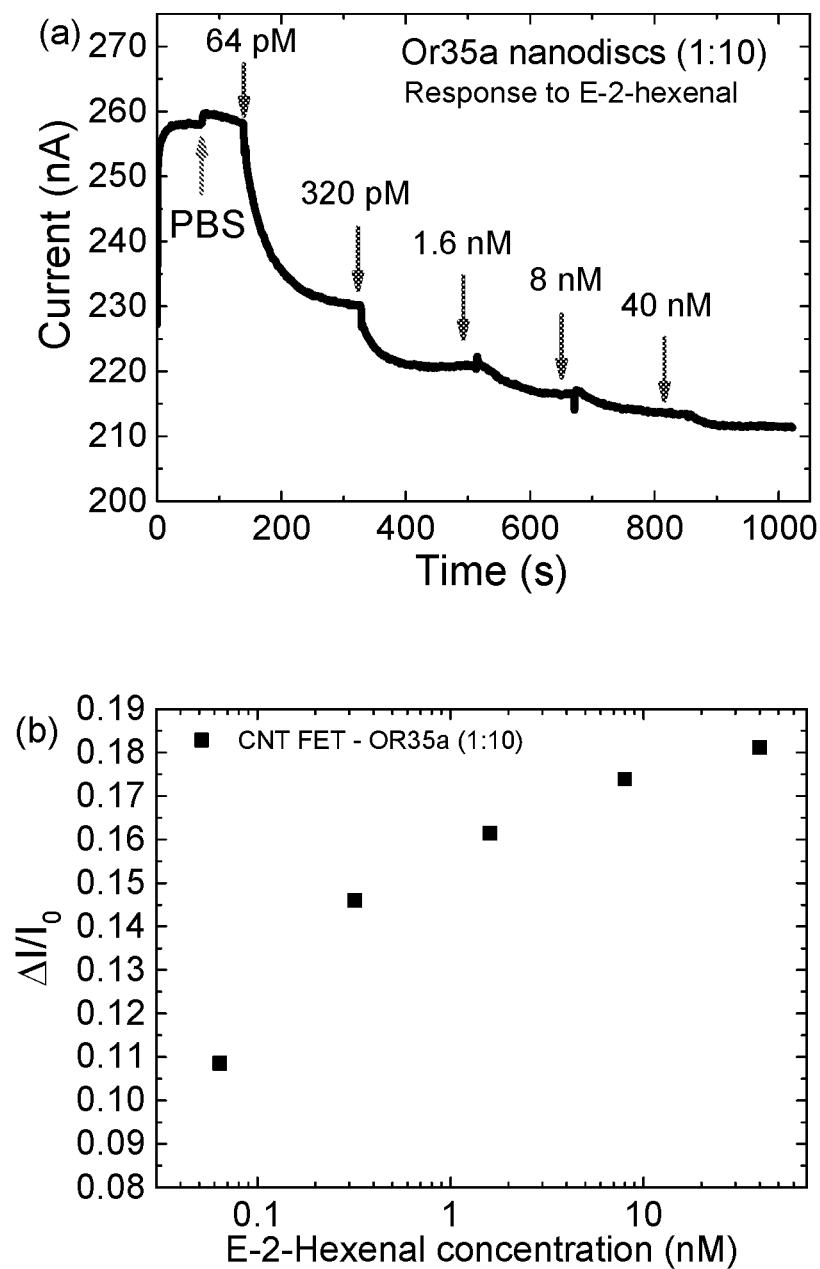
FIG. 11. Real time response to PBS and the target ligand E-2-hexenal from CNT FETs functionalized with OR35a nanodiscs (1:10 dilution): (a) the real time current response and (b) the normalized ($\Delta I/I_0$) vs E-2-hexenal concentration in logarithmic scale.

The CNT FET was functionalized as described above with OR35a nanodiscs at 1:10 dilution. PBS buffer is added to the testing well then E-2-hexenal is added in the sequence of 64 pM, 320 pM, 1.6 nM, 8 nM, 40 nM and 200 nM every 3 minutes, while constantly monitoring the source-drain current of the device. In FIG. 11(a) there is a small increase in current with addition of PBS buffer, whereas the current shows an immediate large decrease after exposure to 64 pM E-2-hexenal. This decrease in current is due to the binding of OR35a with E-2-hexenal changing the effective gating to the CNT FETs[58, 60, 62]. Further current decreases are observed upon exposure to 320 pM, 1.6 nM, 8 nM and 40 nM E-2-hexenal respectively.

FIG. 11(b) shows the dependency of the normalized current response current on the concentration of E-2-hexenal. The change in current ΔI is calculated by $\Delta I = I - I_0$ based on the real time measurement in FIG. 11(a) where I is the stabilized current after exposure to E-2-hexenal and $I_0$ is the initial current before adding 64 pM E-2-hexenal to the testing well. At 64 pM, $\Delta I/I_0$ is changed by 10%. To achieve S like Langmuir adsorption curve, lower concentration and more measurements are required, as here our initial measurement was carried out with E-2-hexenal at 64 pM concentration. Here, the $\Delta I/I_0$ continues to increase as higher concentrations of E-2-hexenal are added to the device well.

3.3 Control Experiments

Figure 12:
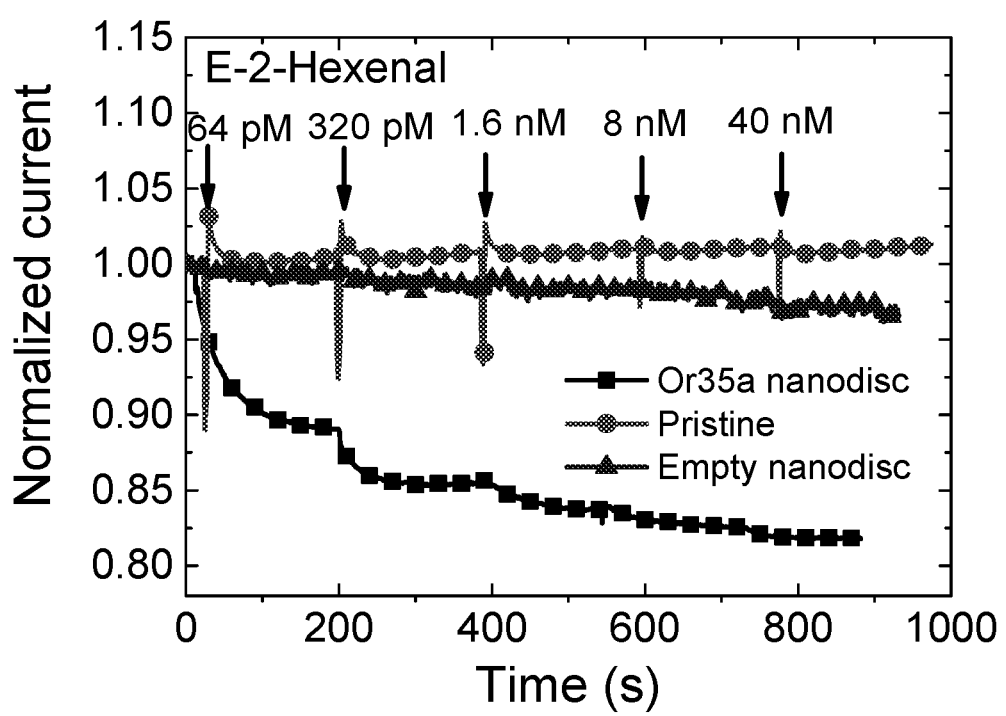
FIG. 12. Real time measurements for the E-2-hexenal response from the CNT FET. functionalized with Or35a nanodiscs (1:10), a pristine CNT FET and CNT FETs functionalized with empty nanodiscs: All devices have $V_{lg}$=0, $V_{ds}$=100 mV and t=1 s.

To ensure the current response is truly from the binding of OR35a with E-2-hexenal, control experiments were carried out. These measurements are E-2-hexenal response from pristine CNT FETs and CNT FETs functionalized with empty nanodiscs. The real time current measurements are plotted in FIG. 12 to show the comparison.

3.3.3 Verifying OR35 Nanodiscs Do Not Response to Control Ligand

Figure 13:
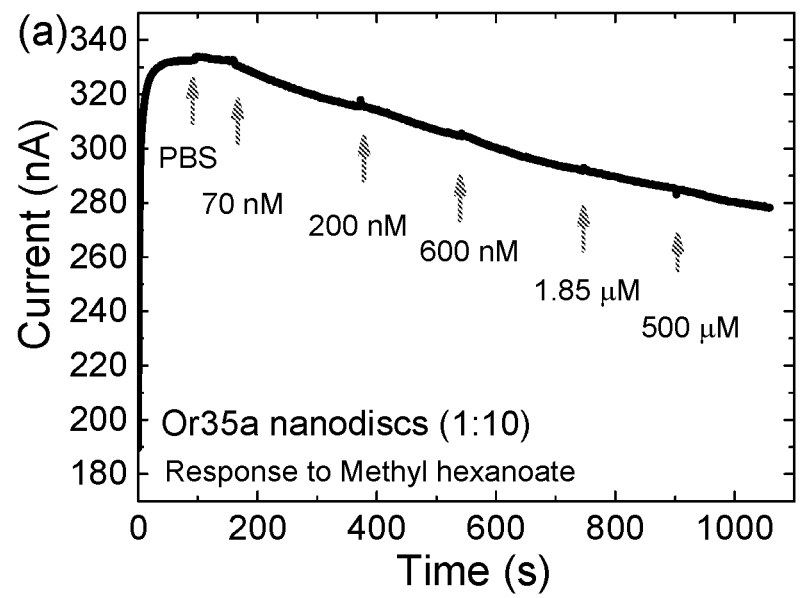
FIG. 13. OR35a-nanodisc (1:10) functionalized CNT FETs response to control ligand methyl hexanoate at $V_{lg}$=0, $V_{ds}$=100 mV, t=1 s: (a) Current response; (b) Normalized current where $I_0$ is the current before starting adding analytes.
Figure 13:
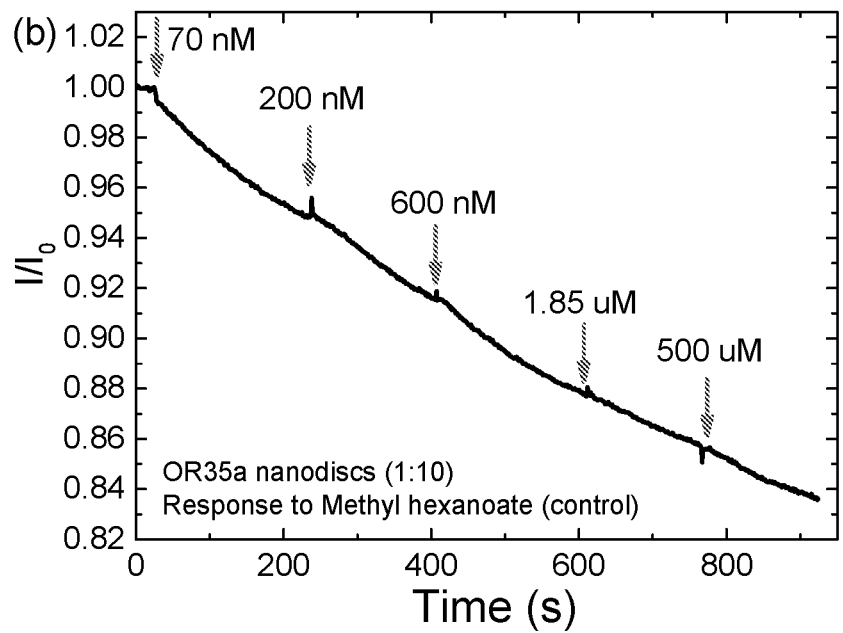

The electrical response of the OR35a nanodiscs to a non-specific ligand, in this case methyl hexanoate, is also measured, FIG. 13. The measured concentration range in FIG. 13 is from 70 nM to 500 µM which is higher than the measurement range of E-2-hexenal concentration in FIG. 12. Unlike results presented in FIG. 11, where a clear step-like response at the time of adding E-2-hexenal is observed and current reaches stability after 3 minutes, the real time measurement for methyl hexanoate ligand in FIG. 13 shows a background drift current with time but no clear response.

4. Conclusion

This study has demonstrated the recognition ability of OR35a and promising olfactory biosensor application based on electronic device platforms. OR35a embedded in nanodiscs are functionalized on the CNT FETs via polyhistidine tag after CNTs are functionalized with Ni-NTA. Ni-NTA is linked on N-hydroxysuccinimide groups of PBASE functionalized CNT FETs. By using this method, the OR35a nanodisc functionalized CNT FET demonstrates a response to 64 pM E-2-hexenal ligand in real time and no response to PBS buffer. Compared with results from the pristine CNT FET, as well as empty nanodisc functionalized CNT FET, no clear current response to E-2-hexenal is observed. The specific binding of OR35a has also been verified by testing the response to PBS and a control ligand methyl hexanoate from the OR35a functionalized CNT FETs. The OR35a nanodisc functionalized CNT FETs have demonstrated specific and sensitive detection of E-2-hexenal in real time.

Comparative data shows that the insect OrX-CNT-FET biosensor format disclosed here is more sensitive than other sensor formats that have been used with insect odorant receptors.

Table 4 summarises the published data odorant receptor based devices. We estimate that the present device provides between 100-10,000-fold greater sensitivity than cell-based sensors.

TABLE 4

Comparison of insect odorant receptor sensor device data.

| Sensor/assay approach | Receptor - analyte | Sensitivity limit | Ec50 | Ref |
|---|---|---|---|---|
| Stable Sf21 cell line on microfluidics chip-fluorescence | BmOR1/Ocro - Bombykol pheromone | $1 \times 10^{-6}$ M | $4.39 \times 10^{-6}$ M | 13 |
| | BmOR3/Orco - Bombykal pheromone | $0.3 \times 10^{-6}$ M | $2.03 \times 10^{-6}$ M | |
| Xenopus oocytes on a microfluidics device -two electrode voltage clamping (TEVC) | BmOR1/Orco - Bombykol pheromone | $10^{-8} - 10^{-6}$ M* | $0.25 \times 10^{-6}$ M | 12 |
| | BmOR3/Orco - Bombykal pheromone | $10^{-8} - 10^{-6}$ M* | $0.38 \times 10^{-6}$ M | |
| | PxOR1/Orco - Z11-16:Ald | $10^{-8} - 10^{-6}$ M* | $2.52 \times 10^{-6}$ M | |
| | DOr85b/Orco to 2-heptanone | $10^{-8} - 10^{-6}$ M* | $45.6 \times 10^{-6}$ M | |
| Insect OrX-EIS device | DmOr35a - E2-hexenal | $1 \times 10^{-15}$ M | $\sim 0.3 \times 10^{-9}$ M | Present study |

* indicates value has been estimated from a visual assessment of dose response data plotted on a graph in the cited reference.

Table 3 summarises data obtained from cell assays. The present insect OrX-CNT-FET sensor data is more sensitive than OrX/Orco expressed in HEK293 cells and *Xenopus oocytes*. Note in these systems some pheromone receptors (PRs) exhibit much lower sensitivity than normal odorant receptors, this is to be expected as these receptors are finely tuned to their pheromone target molecules.

Example 3

Further Exemplification of the Sensor of the Invention with a Carbon Nanotube-Field Effect Transistor (CNT-FET)

1. Summary

The applicants have further exemplified the convenient, sensitive sensor device using insect OrX sequences. Four *Drosophila melanogaster* OrX receptors (Or10a, Or22a, OR35a and Or71a)[43,63] were each embedded in nanodiscs[55,56] and functionalized on the CNT FETs via 1-pyrenebutanoic acid succinimidyl ester (PBASE) and amine group reaction (present on the OrX and membrane scaffold proteins) under further optimized conditions. Each of the OrX functionalized CNT FETs have shown a clear electronic response to their target ligands (Or10a to methyl salicylate, Or22a to methyl hexanoate, Or35a to E-2-hexenal, and Or71a to 4-ethyl guaiacol) in real time current measurement mode starting at 1 fM concentration. The specificity of the binding is verified by testing each OrX functionalized CNT FETs response to control materials, PBS and non-responding ligands. To further ensure the specificity the response of pristine CNT FET and empty nanodisc functionalized CNT FETs to the target ligands are also tested.

2. Experimental Methods 2.1 Materials

Membrane scaffold protein MSP1E3D1 was purchased from Cube Biotech (#26152) and resuspended to 5 mg/mL in water. 1-palmitoyl-2-oleoyl-sn-glycero-3-phosphocholine (POPC) was purchased from Avanti polar lipids (#850457) and a stock solution at 100 mg/mL in chloroform was stored at −20° C. until needed.

2.2 Carbon Nanotube Transistor Device Fabrication

In this set of experiments random channel CNT FET sensor platforms were fabricated on $SiO_2$/Si substrates ($SiO_2$=100 nm) using a simple solution deposition route and standard photolithography techniques.[20,21] Firstly, the SWNT suspension was prepared in anhydrous 1,2-dichlorobenzene (DCB) using ultra-sonication. 99% semiconductor grade SWNT Bucky paper (Nano Integris) was weighed and dispersed in DCB to obtain 5 μg/ml suspension. The dispersion was sonicated until a clear solution was obtained. The temperature was kept at 25° C. throughout the sonication process. Then the $SiO_2$/Si substrate was functionalised with thiolpyridine molecules by a simple stamping method as shown in FIG. 5(a). The thiolpyridine solution was prepared by dissolving 10 mg of 2-Mercaptopyridine (99%, Sigma Aldrich) in 1 ml of methanol. The solution was spun coated on a polydimethylsiloxane (PDMS) surface at 2000 rpm for one minute. Before the spin coating process, the PDMS surface was cleaned by a 50 W Oxygen plasma for 1 minute to improve the wettability. The cleaned substrates were placed upside down on the PDMS surface for three minutes and washed in ethanol to remove the excess thiolpyridine molecules. Then the substrates were transferred into the CNT suspension and immersed into the suspension for 10 minutes. The samples were removed from the suspension and dipped into Ethanol for another 10 minutes to remove the thiolpyridine molecules in the SWNT network. The alignment markers were deposited by defining the markers by photolithography and thermal evaporation of 5 nm Chromium and 50 nm of Gold. The metal Lift off was done by acetone immersion for 15 minutes followed by an Isopropyl alcohol (IPA) wash and $N_2$ blow dry. The result is a uniform thin film CNT network covering the entire substrate surface.

Coating of CNT films with photoresist and subsequent patterning, and encapsulation of electrodes with photoresist is as described in Example 2 section 2.1.

2.2 Olfactory Receptor Immobilization
2.2.1 Preparation of Purified OR Subunits The purification procedure is a variation on the one detailed in Carraher et al. 2013[14]. To his-tag affinity purify protein from baculovirus-infected Sf9 cells, 500 mL at $2\times10^6$ mL$^{-1}$ were infected with baculovirus at an MOI of 0.1, and incubated at 27° C. for 72 h. The cell pellet was collected by centrifugation at 3800 g for 10 min at room temperature and then resuspended in 40 mL of resuspension buffer A (20 mM Tris/HCl pH 7.5, 100 mM NaCl, 1× protease inhibitor cocktail (Roche Diagnostics GmbH, Germany)), with 25 U/mL Benzonase, then lysed by two passes on an Emulsiflex C5 emulsifier (Avestin, Germany) at 10,000-15,000 psi. The sample was then centrifuged at 1000 g for 5 min to remove whole cells and nuclei. The supernatant was removed and spun at 100,000 g for 1 h at 4° C. The membrane pellet was resuspended in 40 mL of buffer A with 1% w/v detergent (Zwittergent 3-16) and rotated for 1 h at room temperature at 10 rpm. The sample was then centrifuged at 100,000 g for 1 h at 18° C. The supernatant was removed and loaded onto a 1 mL NiNTA column (GE Healthcare) where the zwittergent 3-16 detergent was exchanged to Fos-Choline 14 (FC-14). The column was washed in ten column volumes of buffer B (20 mM Tris/HCl pH 7.5, 3.6 mM FC-14) with 300 mM NaCl and 20 mM imidazole, and a further ten column volumes of buffer B with 100 mM NaCl and 50 mM imidazole. Protein was eluted with four column volumes buffer B with 100 mM NaCl and 500 mM imidazole. Purity was assessed on Coomassie stained SDS-PAGE gels and Western blotting.

Purification was completed with a final size exclusion chromatography (SEC) step. The elution fractions from the NiNTA purification were pooled and centrifuged at 20,000 g for 5 min to remove aggregates and contaminants. Then 5 mL of sample was injected onto a Superdex 200 16/60 column (GE Healthcare) attached to an Akta-Pure chromatography system (GE Healthcare). The sample was run at 1 mL/min in buffer B with 100 mM NaCl, and 2 mL fractions were collected and concentrated using a 100 kDa MWCO Vivaspin2 filter unit (Sartorius, Goettingen Germany) and stored at −80° C.

2.2.2 Preparation of Nanodisc Associated OR Subunits

Nanodiscs were prepared using a protocol modified from Bayburt et al. 2010 and 2003[55, 56]. Nanodiscs were formed at an MSP:protein:lipid ratio of 1:0.2:150. The required amount of lipid was removed from the 100 mg/mL stock and dried under a constant stream of nitrogen gas, then further dried under vacuum overnight. The lipids were resuspended in the required volume of buffer (20 mM Tris/HCl pH 7.5, 100 mM NaCl, 50 mM sodium cholate) and sonicated, resulting in a clear lipid stock at 20 mg/mL concentration. Purified odorant receptor protein in detergent buffer was mixed with the MSP1E3D1 and POPC lipid at the required ratio and incubated on ice for 1 hour. To initiate the reconstitution by removing detergents from the system, Bio-beads SM2 (Bio-Rad #1523920) were added to the sample at a 1:1 weight:volume ratio and the mixture was incubated at 4° C. overnight with constant rotation. Bio-beads were then removed and the incorporated nanodiscs were frozen at −80° C. until required.

The incorporation was confirmed by Coomassie stained SDS-PAGE gels. A sample of the reconstitution mixture prior to the addition of Bio-beads was compared to a sample after the bio-bead incubation step by Coomassie stained SDS-PAGE gel, the MSP1E3D1 and OR bands were clearly identified. The removal of the detergent by the Bio-beads would have caused the OR protein to precipitate if it had not been incorporated into the nanodiscs and thus the OR would not be present in the sample after Bio-bead incubation.

2.2.3 Covalent Functionalization of Carbon Nanotubes

In order to immobilize olfactory receptor nanodiscs on the CNT surfaces a covalent functionalisation route is chosen. The OR functionalisation was achieved via an amine/ester reaction, where the CNT surfaces are initially functionalized with 1-pyrenebutanoic acid succinimidyl ester (PBASE) (95% purity, Sigma Aldrich). To do this, 120 μl volume of PBASE solution is added to the CNT channel for one hour at room temperature. The PBASE solution is made at 10 mM concentration in methanol by ultra-sonication for one minute. After PBASE functionalization, to wash off excess PBASE, CNT FETs are cleaned in methanol three times. To remove residual methanol the device are washed three times in phosphate buffer saline (PBS, pH=7.4).

OR-nanodiscs are immobilized on the PBASE functionalized CNT FETs via an amine/ester reaction specific to the amine groups present on the membrane scaffold protein (MSP) and OR subunits which make up the OR associated nanodisc. To prepare the nanodisc solution, the bulk OR-nanodisc solutions are diluted in PBS buffer at 1:100 dilution. The OR-nanodisc stock solution is usually stored in a −80° C. freezer when not in use. Diluted nanodiscs are added into the PDMS well and the entire CNT surface is then soaked in nanodiscs for 30 minutes for functionalization at room temperature. After the functionalization process, excess nanodiscs are removed by washing in PBS three times.

2.2.4 Film Characterizations

Atomic force microscopy was used for characterizing the CNT film morphology. Nano surfe (NaioAFM) was used and images were taken at tapping mode. The films were characterized before and after nanodisc functionalization.

2.2.5 Electrical Measurements

Electrical measurements were performed as described in Example 2 section 2.3 with the following changes. The gate electrode is an Ag/AgCl wire (BASi, MF 2052). During transfer ($V_{lg}$–$I_{ds}$) measurements the gate voltage ($V_{lg}$) is swept between −500 mV to +1 V and the source drain voltage ($V_{ds}$) is set as 100 mV. For our real time sensing measurement the $V_{lg}$ is set to 0 and $V_{ds}$ is set as 100 mV with a time step of 1 s.

The ligand solution is diluted from a 100 mM stock solution, to the concentration ranges required for the sensing experiments. Stock solutions of ligands were made up to 100 mM concentration in DMSO, and stored at 4° C. when not in use. To further dilute the solution down to the testing range, PBS buffer is used. The measurement range of ligand in PBS (containing 1% DMSO) is 1 fM-10 pM (in 10 fold increases). During the real time measurement, PBS solution (containing 1% DMSO) is initially added as control and the analytes are added additionally with increased concentrations.

2.2.6 Ligand Dilution

The ligand solution is diluted from a 100 mM stock solution, to the concentration ranges required for the sensing experiments. Stock solutions of ligands were made up to 100 mM concentration in DMSO, and stored at 4° C. when not in use. To further dilute the solution down to the testing range, PBS buffer is used. The measurement range of ligand in PBS (containing 1% DMSO) is 1 fM-10 pM (in 10 fold increases). During the real time measurement, PBS solution (containing 1% DMSO) is initially added as control and the analytes are added additionally with increased concentrations.

Figure 14:
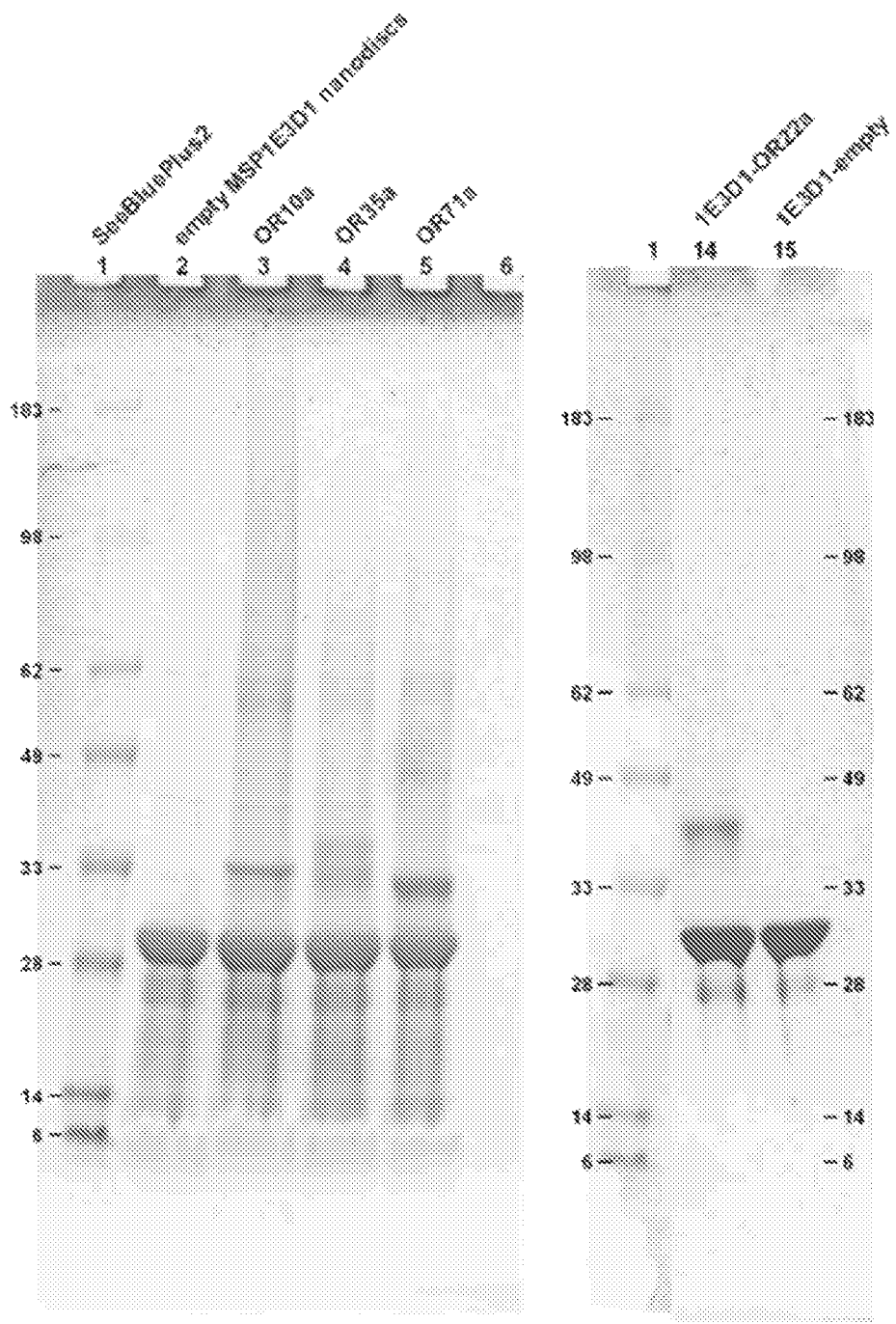
FIG. 14. Coomassie stained SDS-PAGE gels (A) empty 1E3D1 nanodiscs and nanodiscs containing the Or10a, Or35a, Or71a and Or22a receptors; and (B) atomic force microscopy images of pristine CNTs and an example of Or22a nanodisc functionalised CNTs—the yellow dots are the Or22a associated nanodiscs.
Figure 14:
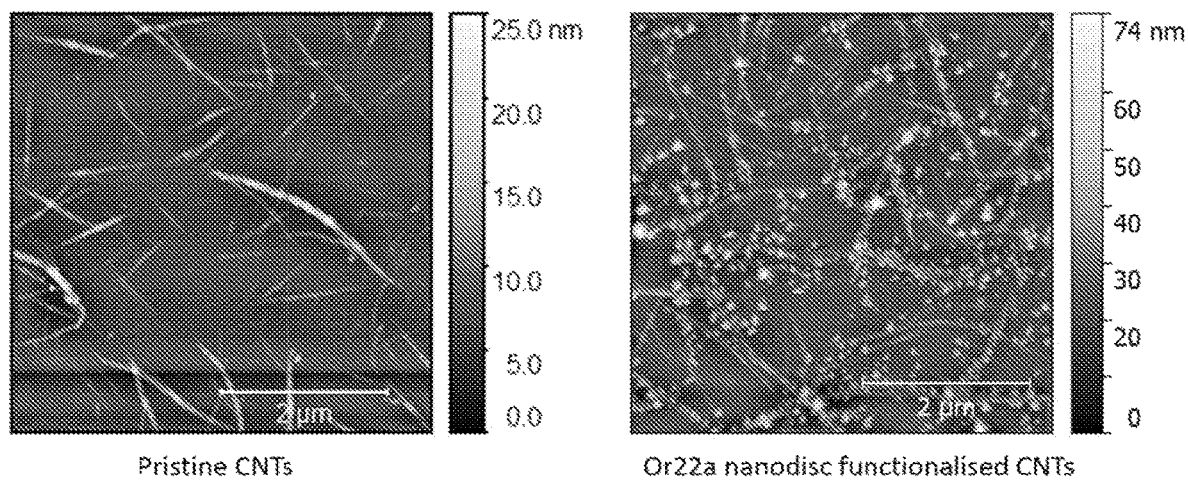

3.0 Results 3.1 Transfer Characteristics of CNT FETs Post OrX-Nanodisc Covalent Functionalization FIG. 14a shows a Coomassie stained SDS-PAGE gel analysis of each of the OrX associated nanodiscs, and example AFM images of pristine and OrX nanodisc functionalised CNTs confirming the immobilisation of the OrX nanodiscs to the CNTs (FIG. 14b), note the white dots on the CNTs. FIG. 15a compares the OR10a nanodisc functionalized CNT FET (blue line) with the pristine CNT FET (black line), where it is clear that the threshold voltage has shifted towards the negative voltage direction after the OR10a nanodisc functionalization. As described in Example 2 section 3.1 this is evidence of successful immobilization of OrX-nanodiscs. As shown in FIGS. 16a, 17a, and 18a, CNT FETs successfully functionalized with Or22a, Or35a and Or71a respectively, the threshold voltage is always shifted in the negative voltage direction.

3.2. OrX Associated Nanodiscs and Respective Ligand Binding 3.2.1. CNT FETs Covalently Functionalized with OrX Nanodiscs (1:100 Dilution)

Figure 15:
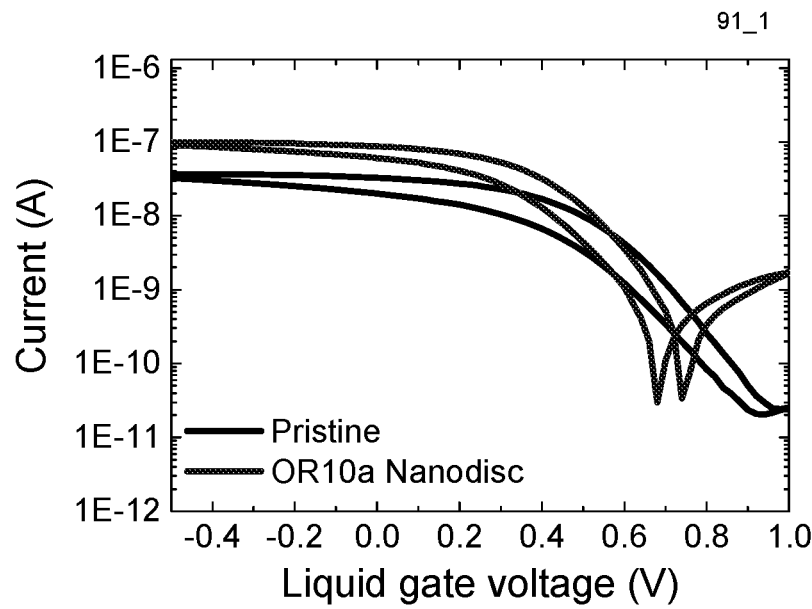
FIG. 15. (A) Transfer characteristics of a pristine CNT FET and the same device after immobilization of Or10a nanodiscs: $V_{ds}$=100 mV, in PBS buffer. (B) real-time current response to PBS and the target ligand methyl salicylate (MeSal) from CNT FETs covalently functionalized with OR10a nanodiscs (1:100 dilution). (C) real-time current response to PBS and the target ligand methyl salicylate (MeSal) from CNT FETs covalently functionalized with empty nanodiscs (1:100 dilution). (D) normalized ($\Delta I/I_0$) vs methyl salicylate concentration and the negative control ligand E2-hexenal (E2Hex) in logarithmic scale from CNT FETs covalently functionalized with OR10a nanodiscs (1:100 dilution). (E) normalized ($\Delta I/I_0$) vs methyl salicylate concentration in logarithmic scale from CNT FETs covalently functionalized with empty nanodiscs (1:100 dilution).
Figure 15:
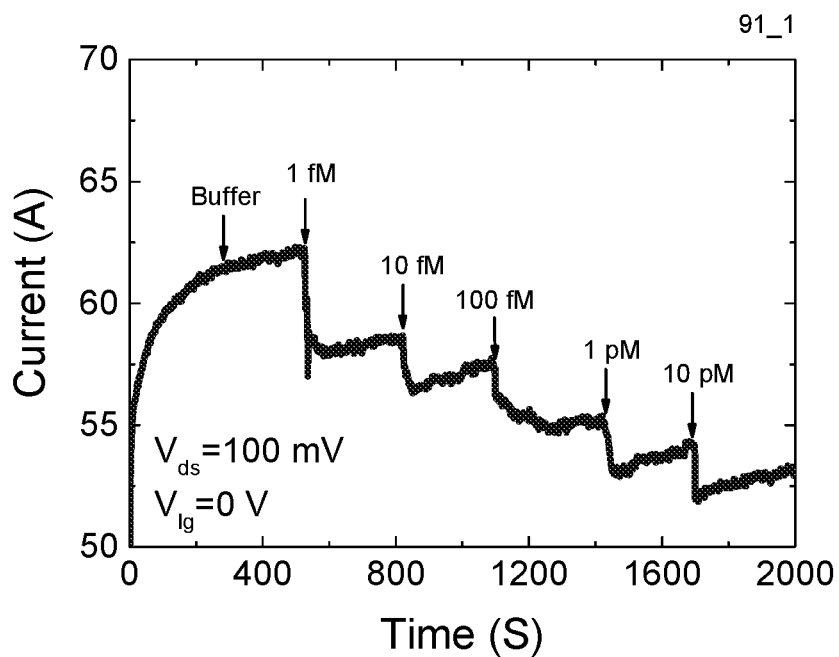
Figure 15:
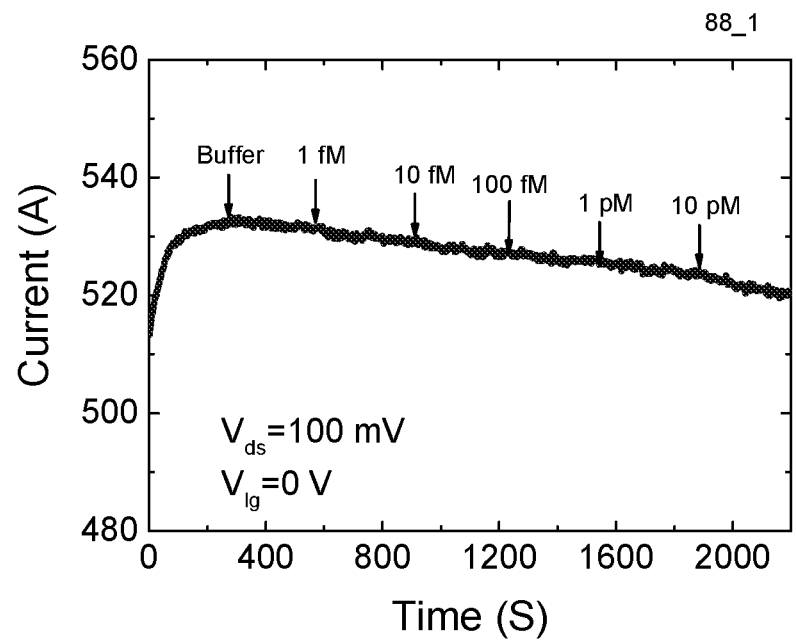
Figure 15:
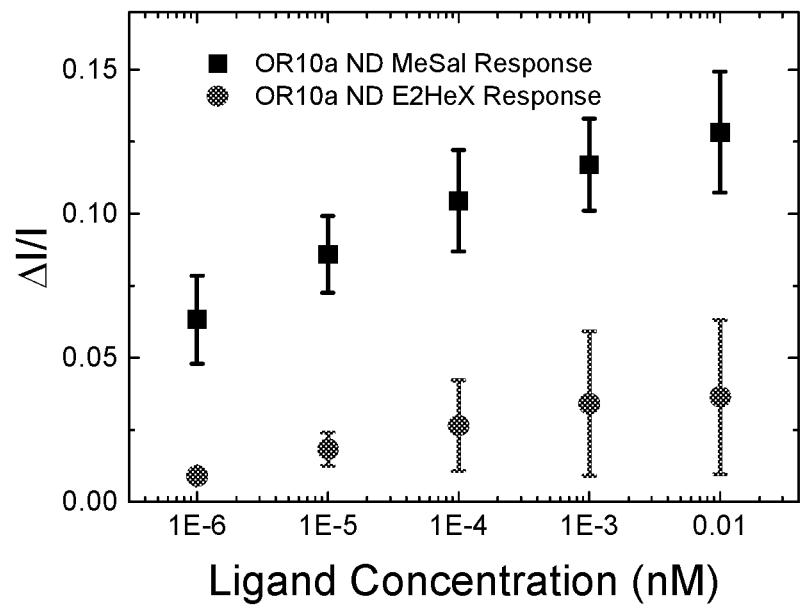
Figure 15:
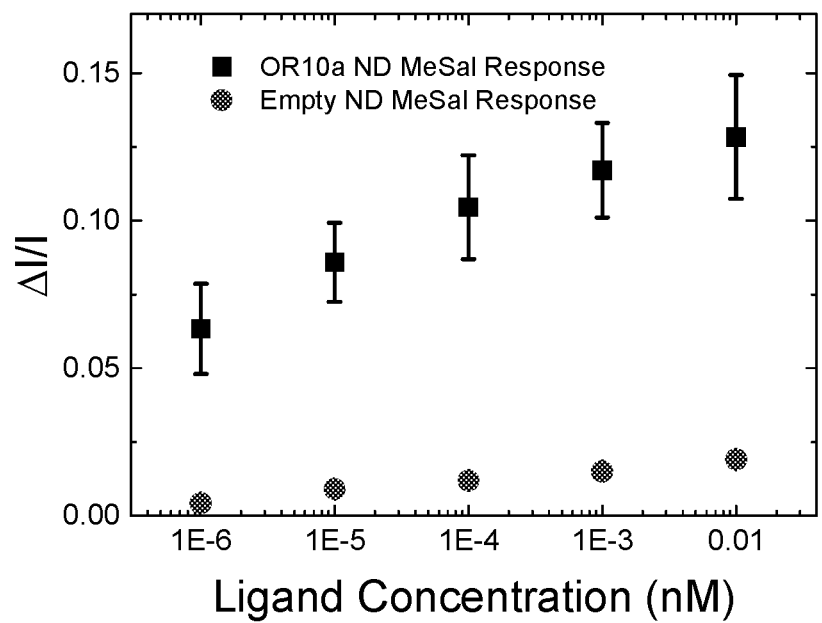

FIG. 15(b) shows that there is a small increase in current from CNT FETs covalently functionalized by OR10a nanodiscs (1:100 dilution) with addition of PBS buffer, whereas the current shows consistently large decreases after exposure to increasing additions of methyl salicylate. This decrease in current is due to the binding of OR10a with methyl salicylate changing the effective gating to the CNT FETs[58, 60, 62]. FIG. 15(c) shows that there is a no increase in current from CNT FETs covalently functionalized with empty nanodiscs (1:100 dilution) with addition of increasing amounts of methyl salicylate confirming the role of Or10a in binding methyl salicylate. FIG. 15(d) shows the dependency of the normalized current response current on the concentration of methyl salicylate, with no response being observed for the control ligand E2-hexenal. FIG. 15(e) shows there is no change in the normalised current response for CNT-FETs covalently functionalized with empty nanodiscs (1:100 dilution). FIGS. 15(d & e) indicate that the limits of detection exhibited by Or10a nanodiscs for methyl salicylate are below 1 fM.

Figure 16:
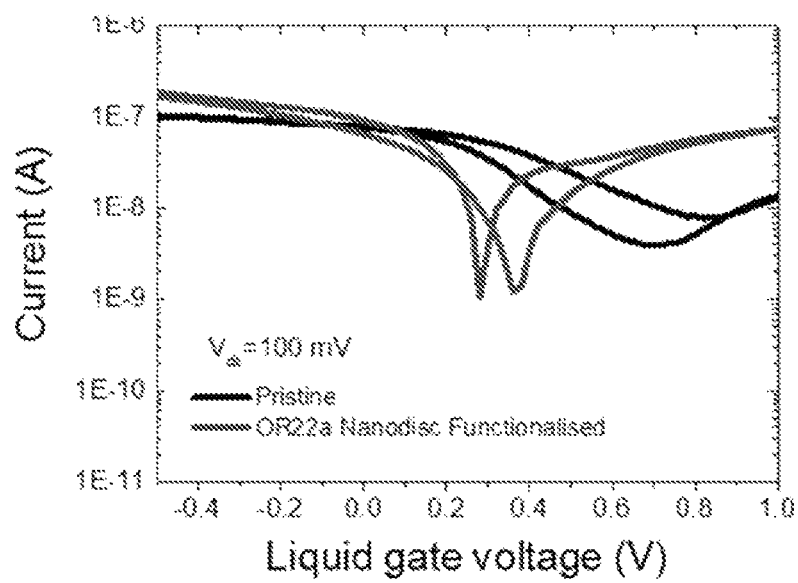
FIG. 16. (A) Transfer characteristics of a pristine CNT FET and the same device after immobilization of Or22a nanodiscs: $V_{ds}$=100 mV, in PBS buffer. (B) real-time current response to PBS and the target ligand methyl hexanoate (MeHex) from CNT FETs covalently functionalized with OR22a nanodiscs (1:100 dilution). (C) real-time current response to PBS and the target ligand methyl hexanoate (MeHex) from CNT FETs covalently functionalized with empty nanodiscs (1:100 dilution). (D) normalized ($\Delta I/I_0$) vs methyl hexanoate concentration and the negative control ligand E2-hexenal (E2Hex) in logarithmic scale from CNT FETs covalently functionalized with OR22a nanodiscs (1:100 dilution). (E) normalized ($\Delta I/I_0$) vs methyl hexanoate concentration in logarithmic scale from CNT FETs covalently functionalized with empty nanodiscs (1:100 dilution).
Figure 16:
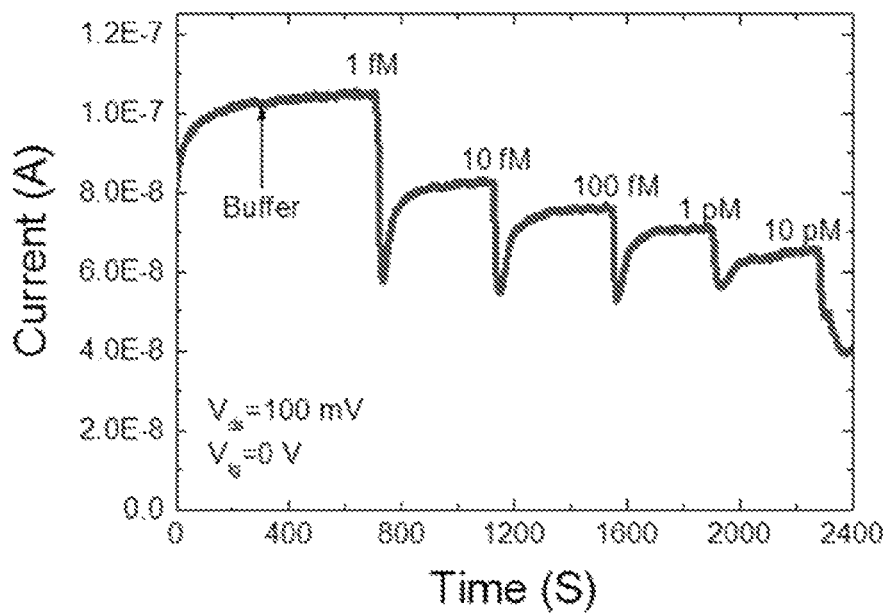
Figure 16:
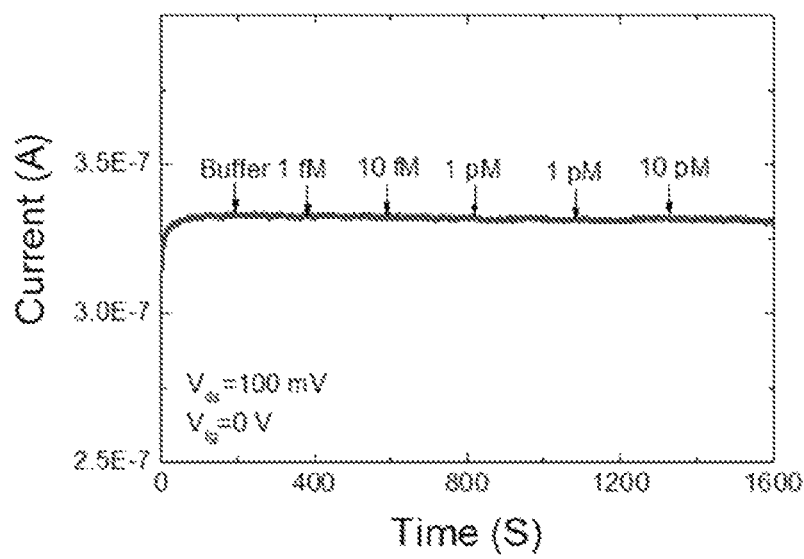
Figure 16:
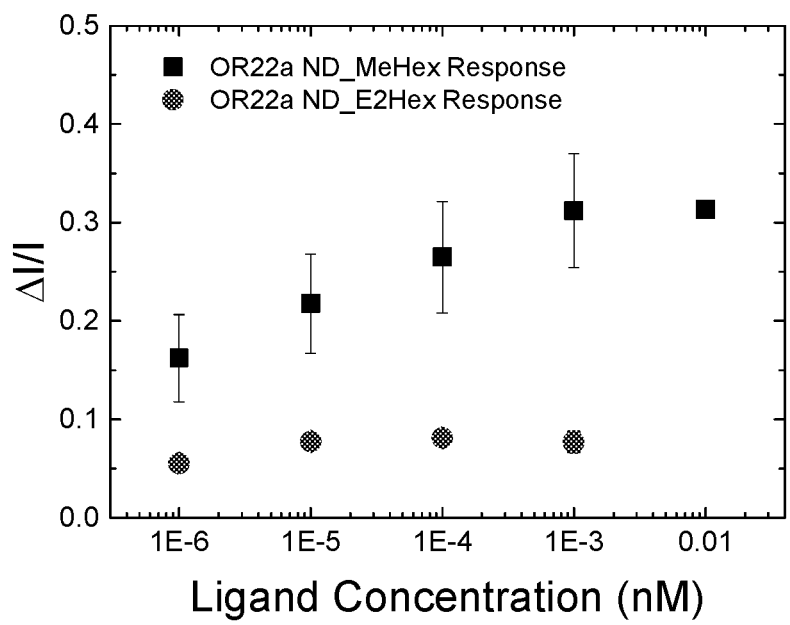
Figure 16:
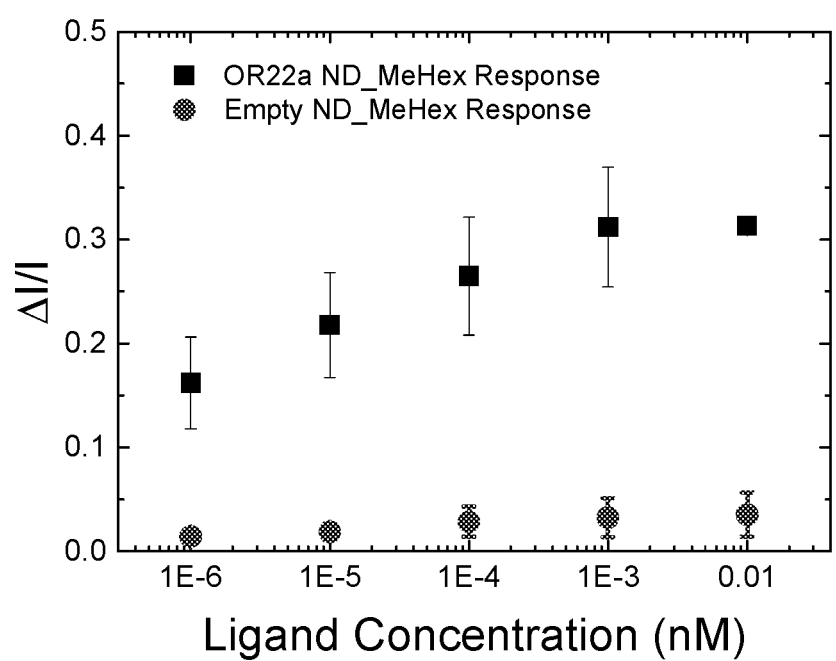
Figure 17:
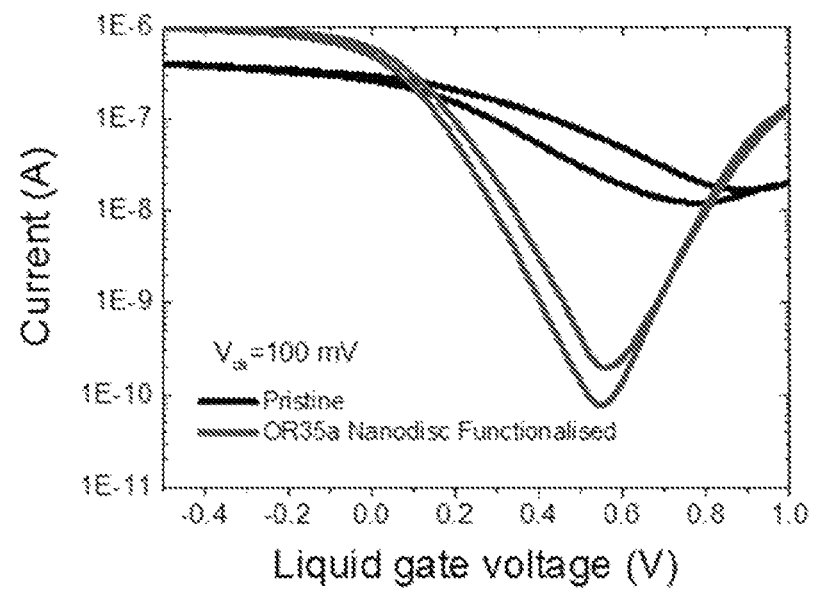
FIG. 17. (A) transfer characteristics of a pristine CNT FET and the same device after immobilization of Or35a nanodiscs: $V_{ds}$=100 mV, in PBS buffer. (B) real-time current response to PBS and the target ligand E2-hexenal (E2Hex) from CNT FETs covalently functionalized with OR35a nanodiscs (1:100 dilution). (C) real-time current response to PBS and the target ligand E2-hexenal (E2Hex) from CNT FETs covalently functionalized with empty nanodiscs (1:100 dilution). (D) normalized ($\Delta I/I_0$) vs E2-hexenal (E2Hex) concentration and the negative control ligand methyl hexanoate (MeHex) in logarithmic scale from CNT FETs covalently functionalized with OR35a nanodiscs (1:100 dilution). (E) normalized ($\Delta I/I_0$) vs E2-hexenal (E2Hex) concentration in logarithmic scale from CNT FETs covalently functionalized with empty nanodiscs (1:100 dilution).
Figure 17:
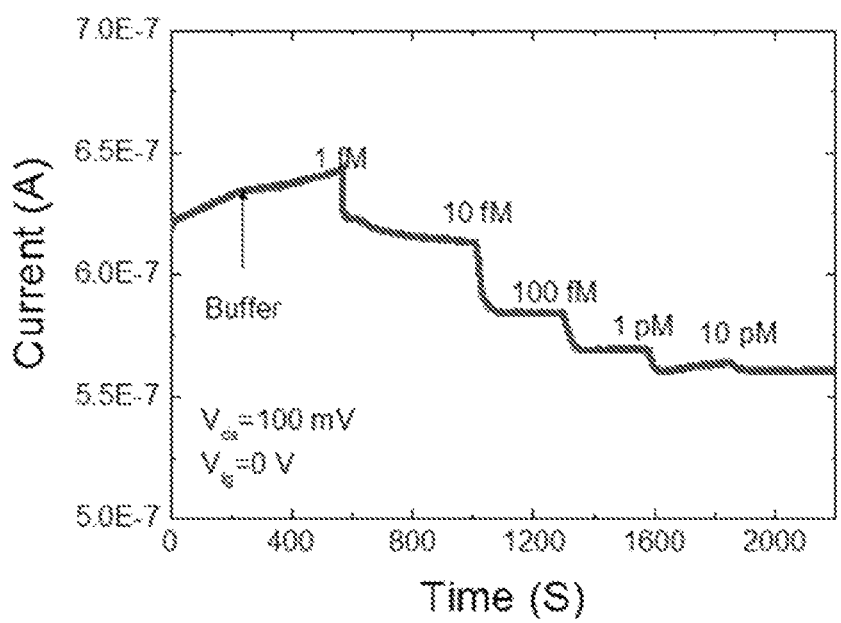
Figure 17:
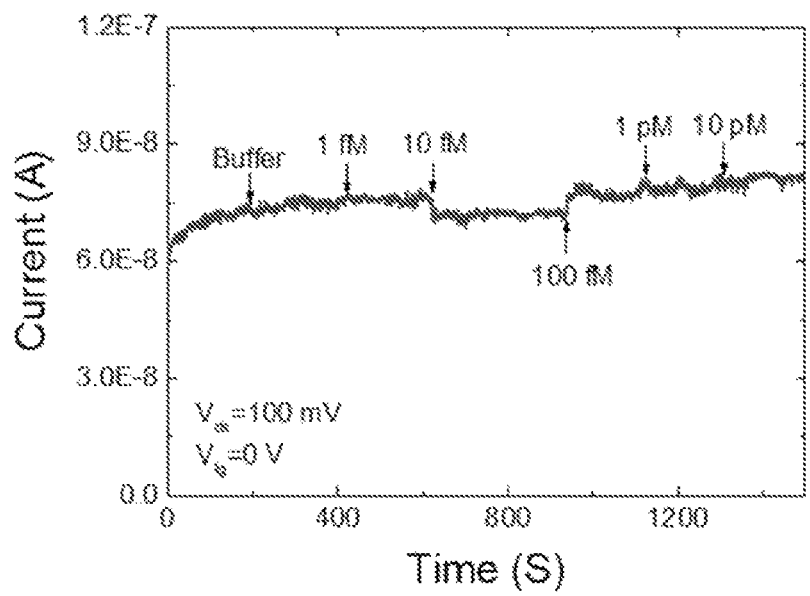
Figure 17:
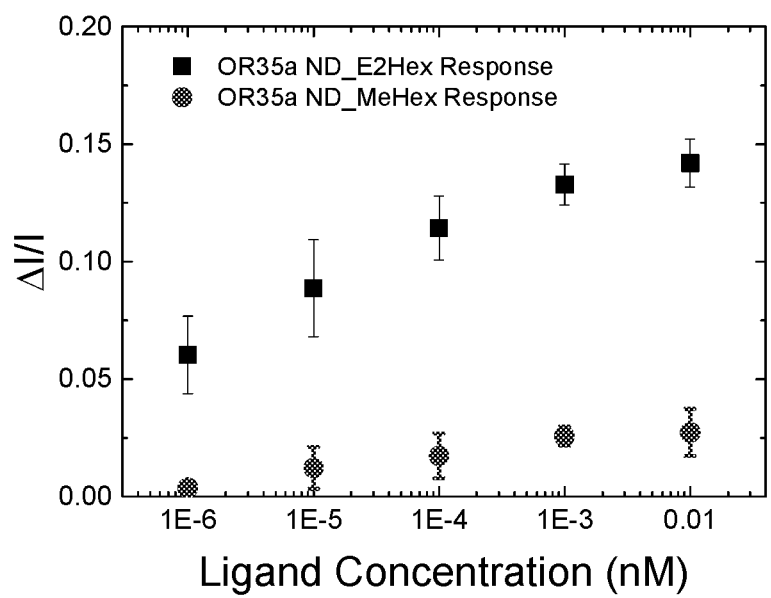
Figure 17:
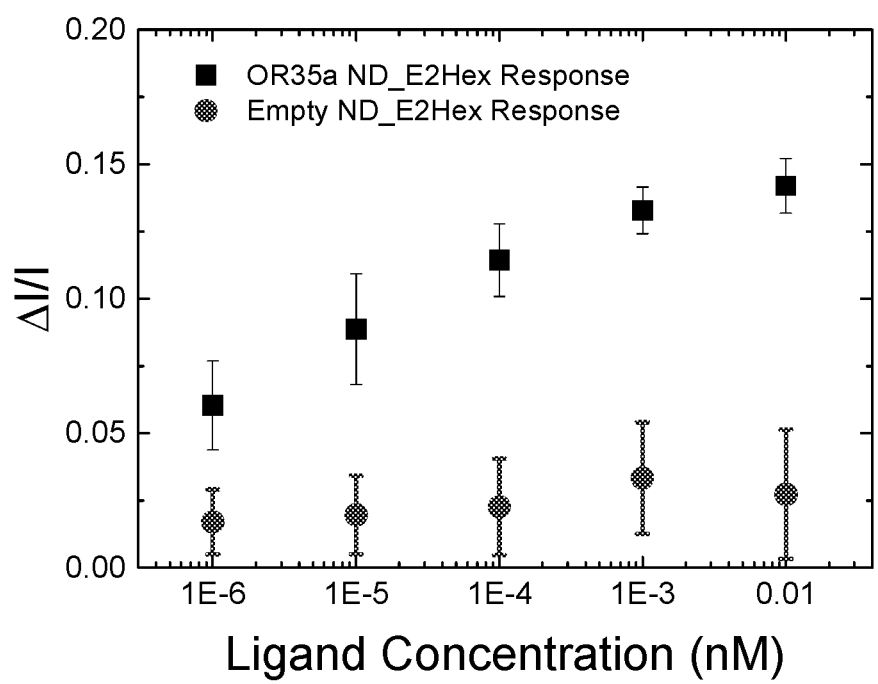
Figure 18:
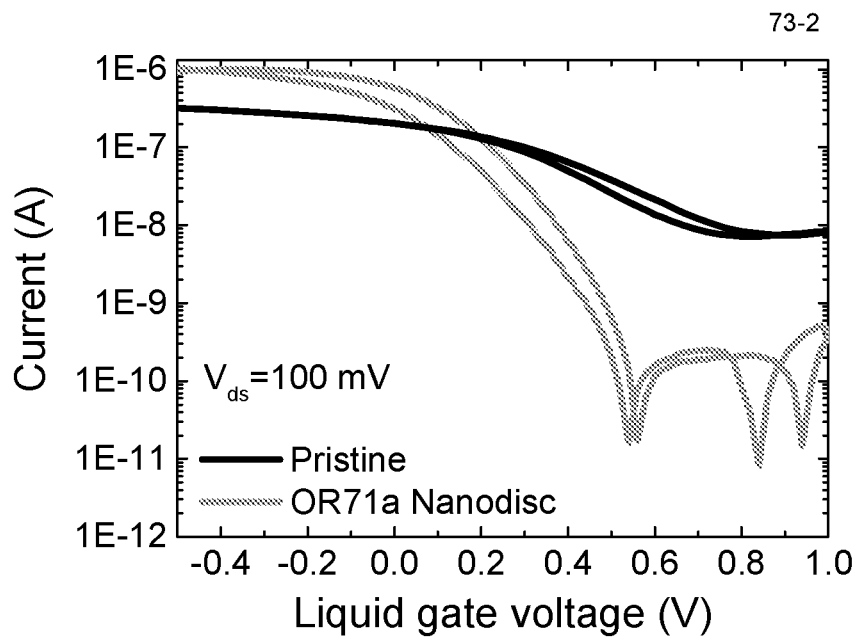
FIG. 18. (A) shows transfer characteristics of a pristine CNT FET and the same device after immobilization of Or71a nanodiscs: $V_{ds}$=100 mV, in PBS buffer. (B) real-time current response to PBS and the target ligand 4-ethyl guaiacol (4EG) from CNT FETs covalently functionalized with OR71a nanodiscs (1:100 dilution). (C) real-time current response to PBS and the target ligand 4-ethyl guaiacol (4EG) from CNT FETs covalently functionalized with empty nanodiscs (1:100 dilution). (D) normalized ($\Delta I/I_0$) vs 4-ethyl guaiacol (4EG) concentration in logarithmic scale from CNT FETs covalently functionalized with OR71a nanodiscs (1:100 dilution) and from CNT FETs covalently functionalized with empty nanodiscs (1:100 dilution).
Figure 18:
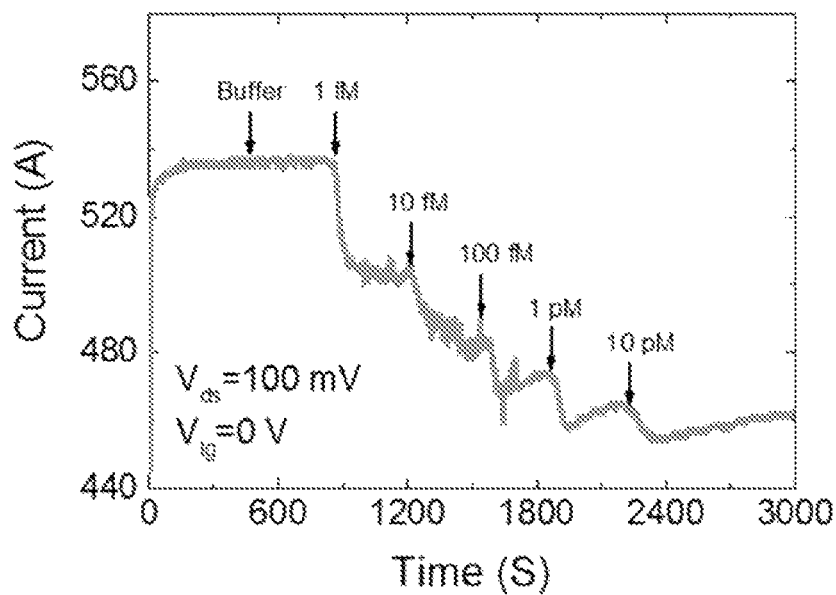
Figure 18:
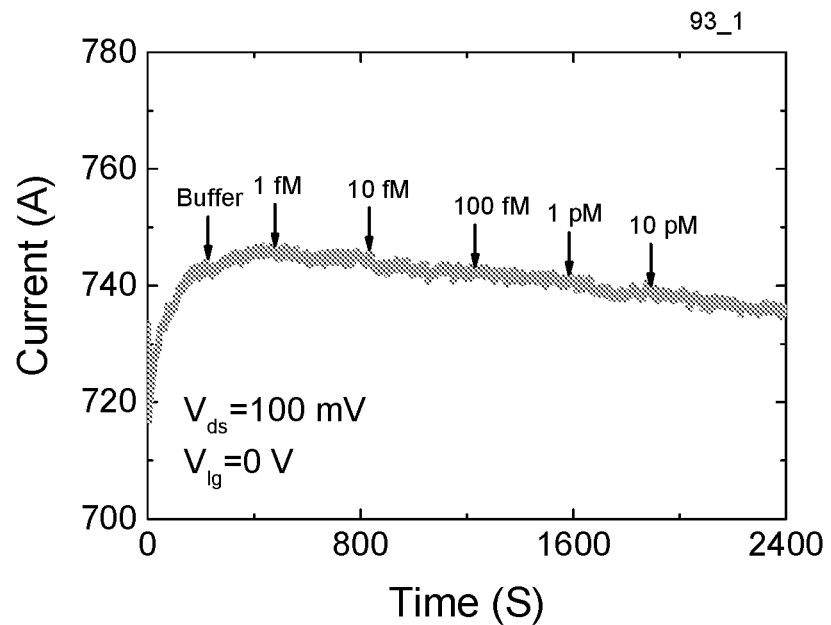
Figure 18:
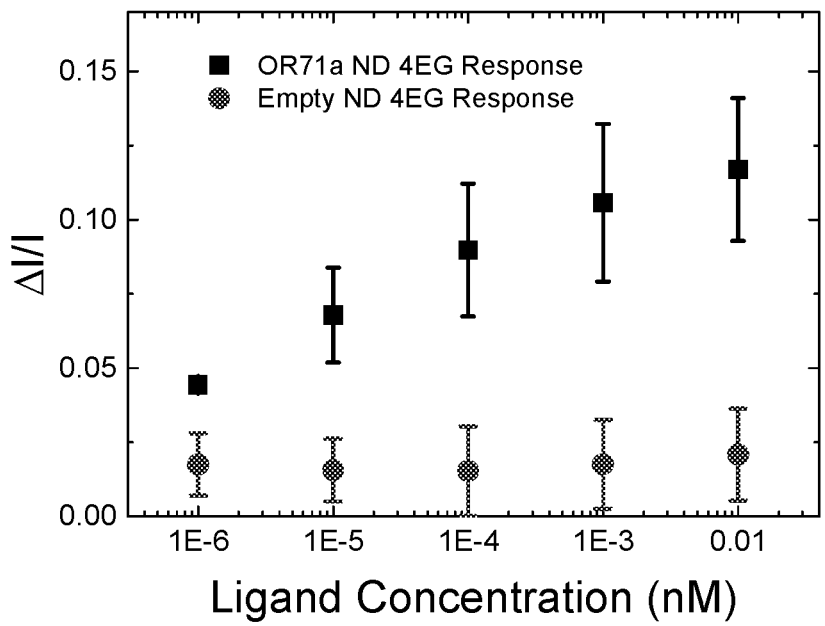

FIGS. 16, 17 and 18 show similar results for CNT FETs covalently functionalized with Or22a (target ligand—methyl hexanoate, control ligand—E2-hexenal), Or35a (target ligand—E2-hexenal, control ligand—methyl hexanoate) and Or71a (target ligand—4-ethyl guaiacol), respectively, and indicate that the limits of detection for each OrX nanodiscs and their respective target ligands are all below 1 fM 4. Conclusion This study has further demonstrated the recognition ability of OrXs and promising olfactory biosensor application based on electronic device platforms. OrXs embedded in nanodiscs are covalently functionalized on the CNT FETs and show current responses to 1 fM target ligands in real time and no response to PBS buffer. This is five-fold more sensitive that the CNT-FET sensor described in Example 2, with a dynamic range of at least four orders of magnitude. Compared with results from empty nanodisc functionalized CNT FETs, no clear current response to target ligands are observed. The specific binding of each OrX has also been verified by testing the response to PBS and control ligands from the OrX functionalized CNT FETs. The OrX-nanodisc functionalized CNT FETs have demonstrated specific and sensitive detection of their target ligands in real time.

Example 4

Further Exemplification of the Sensor of the Invention with Electrical Impedance Spectroscopy (EIS)

1. Summary

The applicants have further exemplified the convenient, sensitive sensor device using insect OrX sequences. Three OrX receptors (Or10a and Or22a, and OR35a)[43, 63] were each embedded in nanodiscs[55,56] and functionalized on gold electrodes for EIS measurements. Each of the OrX functionalized gold electrodes have shown a clear electronic response to their target ligands (Or10a to methyl salicylate, Or22a to methyl hexanoate, and Or35a to E-2-hexenal) in real time starting at fM level concentrations. The specificity of the binding was verified by testing each OrX nanodisc functionalized electrode response to non-responding ligands. To further ensure the specificity the response of empty nanodiscs functionalized gold electrodes to the target ligands were also tested.

2. Experimental Methods 2.1 Materials 6-mercaptohexanoic acid (MHA), N-hydroxysuccinimide (NHS), 1-ethyl-3-(3-dimethylaminopropyl)-carbodiimide) (EDC), phosphate buffer saline (PBS) tablets, methyl salicylate, methyl hexanoate, ethyl hexanoate, E2-hexenal and 4-ethylguaiacol were obtained from Sigma-Aldrich. 1.6 mm diameter gold (Au) disk electrode, coiled platinum (Pt) wire electrode and leakless silver/silver chloride (Ag/AgCl) electrode were purchased from BASi for electrochemical measurements.

2.2 Preparation of Nanodisc Associated OR Subunits 2.2.1 Preparation of Purified OR Subunits OR subunits were prepared as described in Example 3 section 2.3.1

2.2.2 Preparation of Nanodisc Associated OR Subunits

Nanodiscs were prepared as described in Example 3 section 2.3.2

2.3 Electrode Preparation

Gold disk electrodes (1.6 mm diameter) were polished on alumina polishing pad with polishing alumina slurry for one minute for each electrode. The polished electrodes were rinsed with deionised water (Milli-Q, 18.2 MΩ cm) followed by ultrasonication in ethanol (LR grade) and deionised water until the residual alumina slurry was completely removed from the electrodes. Chronoamperometry at −1.2 V was applied onto all of the ultrasonicated electrodes to desorb the SAMs of the thiol present on the surface of the electrodes for 30 seconds using 0.1 M sodium hydroxide (NaOH) electrolyte solution in a three terminal electrochemical cell, Ag/AgCl (3 M NaCl, 0.209 V vs. SHE) reference electrode, coiled platinum wire as a counter electrode and gold disk as a working electrode, using a PalmSens3 potentiostat. Then, the electrodes were again rinsed with deionised water and ultrasonicated in ethanol and deionised water consecutively. Finally, cyclic voltammetry was performed for 10 cycles between −0.2 and 1.6 V, at a scan rate of 100 mV/s in 0.5 M sulphuric acid ($H_2SO_4$) solution to remove any other impurities (a three electrode cell, Ag/AgCl (in 3 M NaCl, 0.209 V vs. SHE) reference electrode, coiled platinum wire as a counter electrode and gold disk as a working electrode).

2.4 Self-Assembled Mono Layer (SAM) Preparation and EDC: NHS Activation 2 mM MHA was prepared by dissolving 1.36 µl of MHA in 5 ml ethanol (AR grade). The cleaned electrodes were immersed into MHA solution and incubated overnight. The next day, all the electrodes were washed with ethanol and deionised water thoroughly in order to remove the unreacted acid. A 2:1 mol:mol ratio of EDC:NHS (100 mM EDC, 50 mM NHS) was prepared in 2 ml PBS (pH=6.5) solution. Then, the electrodes were incubated in this solution at 28° C. for an hour to activate the carboxylic (COOH) groups of the MHA.

2.5 OR Associated Nanodisc Immobilisation on Electrodes

PBS solution was prepared by immersing one tablet of PBS in 200 ml of milli-Q water (according to manufacturers instructions) and filtered using 0.2-µm syringe filter. The pH of the prepared buffer solution was measured with a pH meter. ORs were diluted 100 fold in PBS buffer solution (pH=7.4) and the COOH-activated electrodes were incubated in that buffer solution at room temperature for one hour. Then, the electrodes were washed extensively with PBS buffer solution to wash out any unbound nanodiscs.

2.5 Target Odorant Solution Preparation and Incubation

PBS solution (pH=7.4) was used as an electrolyte to conduct electrochemical measurements; EIS and CV. PBS buffer was degassed for 15 minutes prior to electrochemical measurements. The ligand solution was diluted from a 100 mM stock solution, to the concentration ranges required for the sensing experiments. Stock solutions of ligands were made up to 100 mM concentration in DMSO, and stored at 4° C. when not in use. To further dilute the solution down to the testing range, PBS buffer was used. The measurement range of ligand in PBS (containing 1% DMSO) was 1 fM-100 nM (in 10 fold increases) for Or10a nanodiscs, 100 fM-100 pM (in 10 fold increases) for Or22a nanodiscs, and 10 aM-1 pM (in 10 fold increases) for Or35a nanodiscs.

2.6 Electrochemical Impedance Spectroscopy (EIS) Measurements

OR immobilized electrodes were incubated in relevant odorant solution for ~30 minutes each and washed gently with PBS before EIS measurements. EIS measurements were performed subsequently in a three terminal electrochemical cell comprising of a platinum (Pt) wire as counter electrode (CE), Ag/AgCl (3 M KCl, +0.197 V vs. SHE) reference electrode (RE), and 1.6 mm gold disk electrode with nanodiscs as working electrode (WE) between 100 mHz to 100 kHz with applying −0.7V against the reference.

3.0 Results

Figure 19:
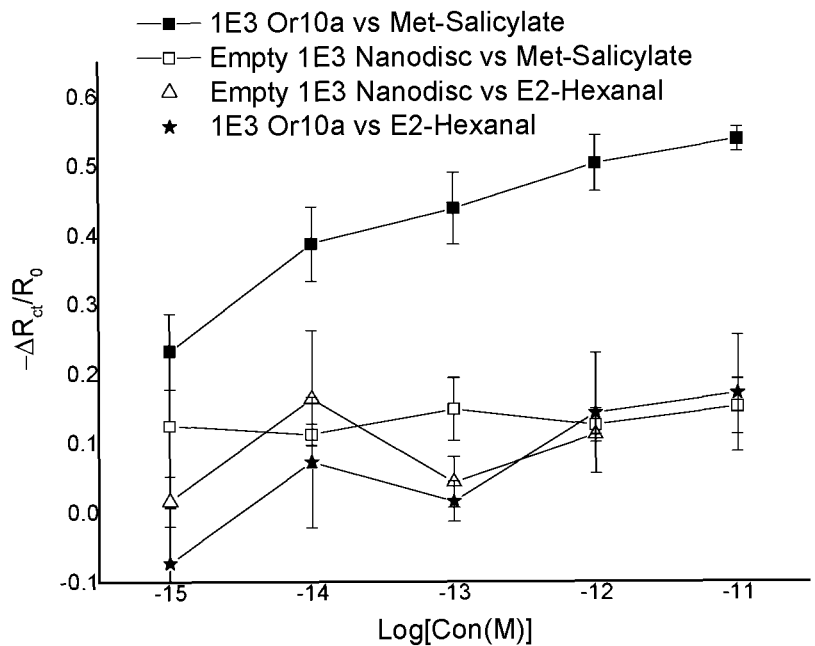
FIG. 19. Dose response curves for gold electrodes functionalized with A) Or10a nanodiscs in response to the target ligand Methyl salicylate and control ligand E2-hexenal. B) Or22a nanodiscs in response to the target ligand Methyl hexanoate and control ligand E2-hexenal. C) Or35a nanodiscs in response to the target ligand E2-hexenal and the control ligand methyl salicylate. In all three examples, target and control ligand binding measurements were also performed with gold electrodes functionalised with empty nanodiscs.
Figure 19:
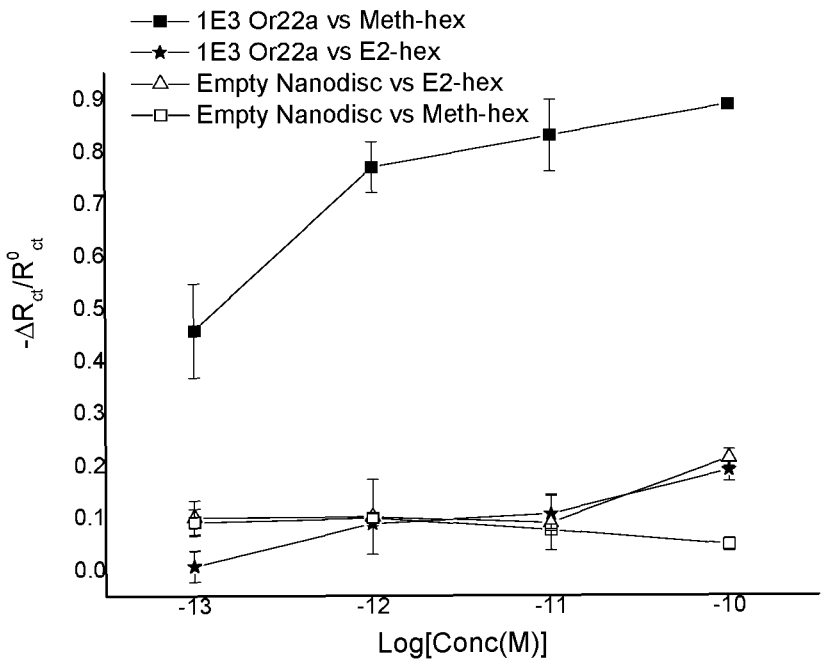
Figure 19:
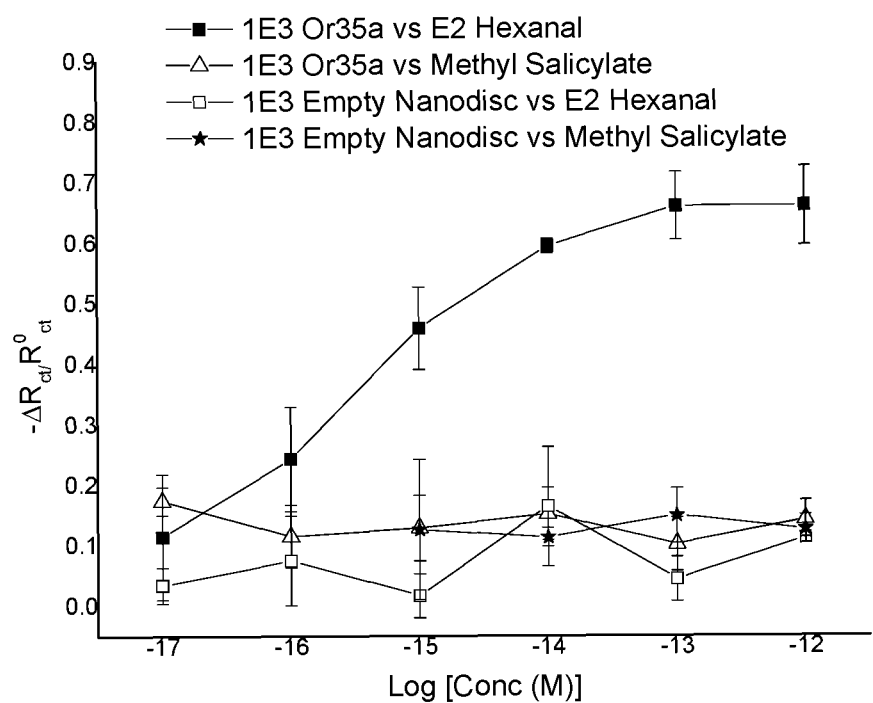

EIS measurements were performed and analysed as described in Example 1 Section 2.0. EIS measurements were performed on gold electrodes functionalised with OrXs (either Or10a, Or22a or Or35a) or empty nanodiscs prior to and after target ligand or control ligand incubation with increasing concentrations. Calibration curves were obtained by defining sensor response as $\Delta R_{ct}/R^{0}_{ct}$ versus log[C(Ligand)] (FIG. 19). FIG. 19(a) shows that Or10a nanodiscs respond sensitively (LOD of 10 fM) and selectively to methyl salicylate, and as expected do not respond to the control ligand E2-hexenal. FIG. 19(b) shows that Or22a nanodiscs respond sensitively (LOD of <100 pM) and selectively to methyl hexanoate, and as expected do not respond to the control ligand E2-hexenal. FIG. 19(c) shows that Or35a nanodiscs respond sensitively (LOD of <1 fM) and selectively to E2-hexenal, and as expected does not respond to the control ligand methyl salicylate. In each of the figures, empty nanodiscs do not respond to any of the target ligands tested demonstrating that the presence of each OrX is the key to the detection of each target ligand.

4. Conclusion

This study has further demonstrated the recognition ability of OrXs and promising olfactory biosensor application based on electronic device platforms. OrXs embedded in nanodiscs functionalized on the gold electrodes show electrochemical impedance responses to fM target ligands, and display a dynamic range of four orders of magnitude. No impedance response to target ligands is observed from empty nanodiscs functionalized electrodes. The specific binding of each OrX has also been verified by testing the response to control ligands from the OrX nanodisc functionalized electrodes. The OrX nanodiscs functionalized electrodes have shown great promise to specifically and sensitively detect their target ligands.

Example 5

Further Exemplification of the Sensor of the Invention with Electrical Impedance Spectroscopy (EIS)

Summary

The applicants have further exemplified the convenient, sensitive sensor device using insect OrX sequences. Three OrX receptors (Or10a, Or22a, OR71a)[43, 63] were each embedded in liposomes[55,56] and functionalized on gold electrodes for EIS measurements under further optimized experimental conditions. Each of the OrX functionalized gold electrodes has shown a clear electronic response to its target ligands (Or10a to methyl salicylate, Or22a to methyl hexanoate, Or71a to 4-ethyl-guaiacol) starting at fM concentrations. The specificity of the binding is verified by testing each OrX liposome functionalized electrode response to non-responding ligands. To further ensure the specificity the response of empty nanodiscs functionalized gold electrodes to the target ligands were also tested.

1. Experimental Methods 2.1 Materials

As described in Example 4 section 2.1

2.2 Preparation of Liposome Associated OR Subunits 2.2.1 Preparation of Purified OR Subunits OR subunits were prepared as described in Example 3 section 2.3.1

2.2.2 Preparation of Liposome Associated OR Subunits

OR and OR/Orco associated liposomes were prepared as described in Example 1 section 1.2.

2.3 Electrode Preparation

As described in Example 4 section 2.3

2.4 Self-Assembled Mono Layer (SAM) Preparation and EDC: NHS Activation

As described in Example 4 section 2.4

2.5 OR Associated Nanodisc Immobilisation on Electrodes

As described in Example 4 section 2.5

2.6 Target Odorant Solution Preparation and Incubation

As described in Example 4 section 2.6

2.7 Electrochemical Impedance Spectroscopy (EIS) Measurements

As described in Example 4 section 2.7

3.0 Results

Figure 20:
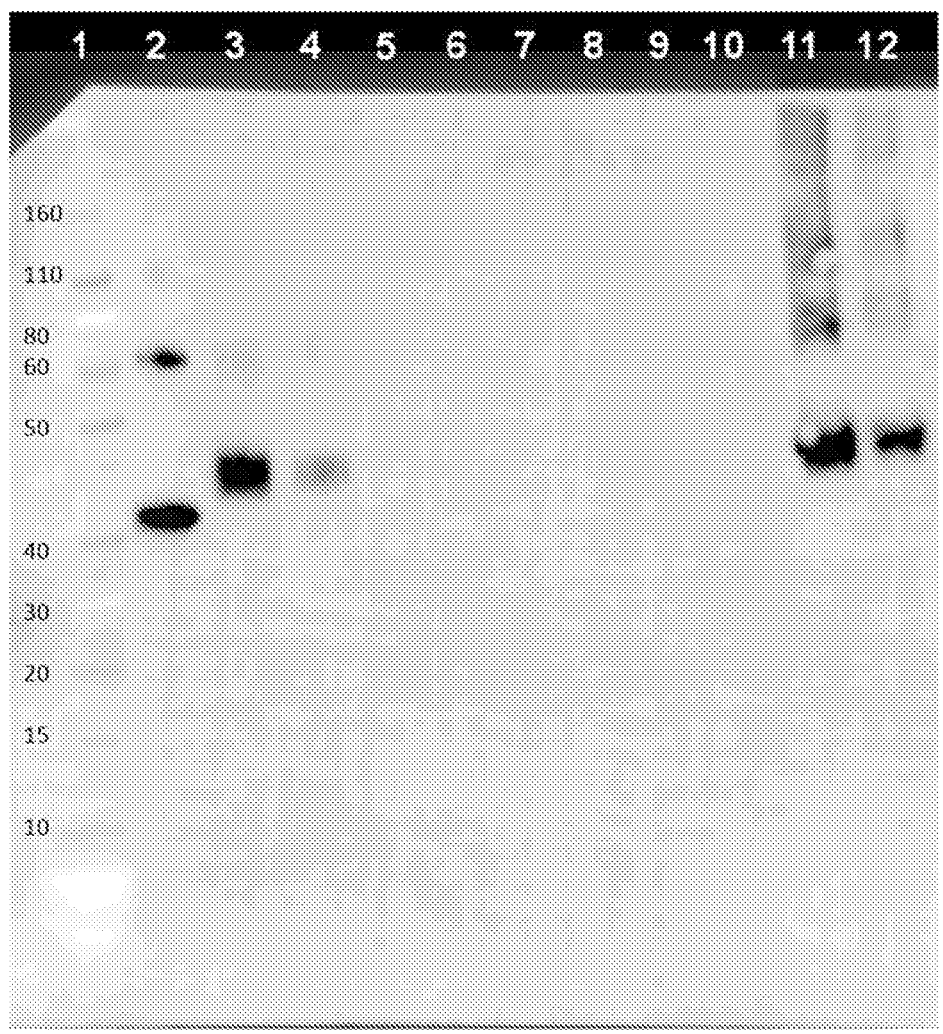
FIG. 20 shows an anti-FLAG western blot of an SDS-PAGE of an Or22a associated liposome preparation. Lanes are 1—MW standards, 2—His-FLAG-CFP western blot standard, 3—His-FLAG-OR22a purified in FC14 detergent, 4—His-FLAG-OR22a reconstituted into liposomes, 5-12: Accudenz flotation gradient fractions from bottom (lane 5) to top (lane 12). Note how the His-FLAG-OR22a bands are only present in the top two fractions indicating they have been reconstituted into liposomes.

FIG. 20 shows a western blot from an SDS-PAGE gel analysis of an example preparation of OR associated liposomes for Or22a. Lane 4 shows the final preparation of Or22a associated liposomes, when accudenz gradient ultracentrifugation (lanes 5-12) is applied to this preparation the Or22a associated liposomes float to the top of the gradient and are found in the top two gradient fractions (lanes 11 &12)[14].

Figure 21:
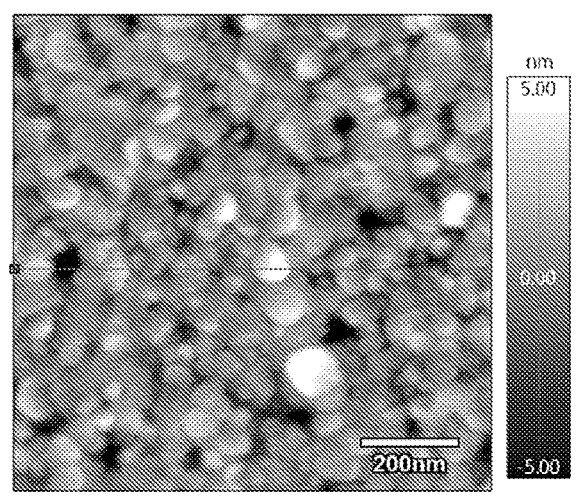
FIG. 21 shows AFM height images (a-d), roughness profile indicated by the marked line on height images (e-h), and 3D images (i-l) of bare, SAM modified, NHS-EDC coupled, and Or22a/liposomes immobilized gold surfaces, respectively.
Figure 21:
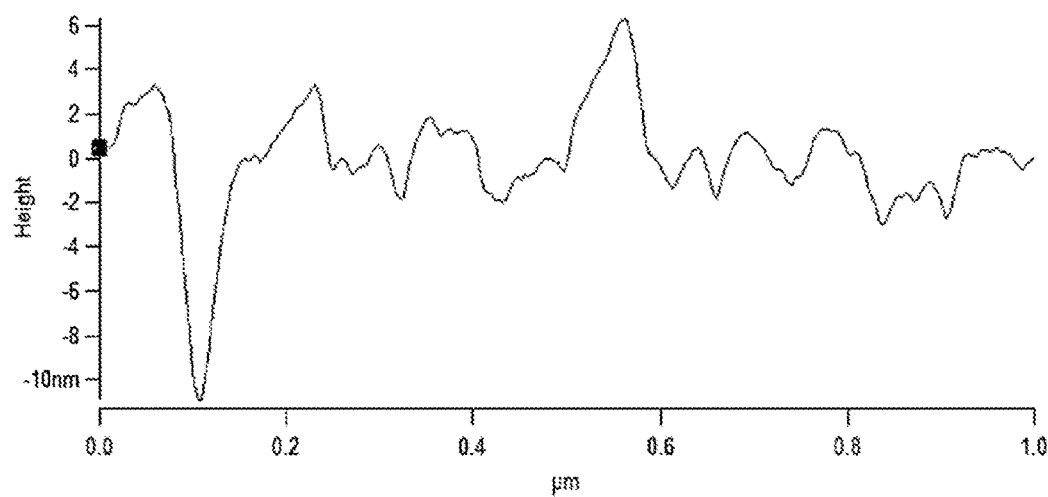
Figure 21:
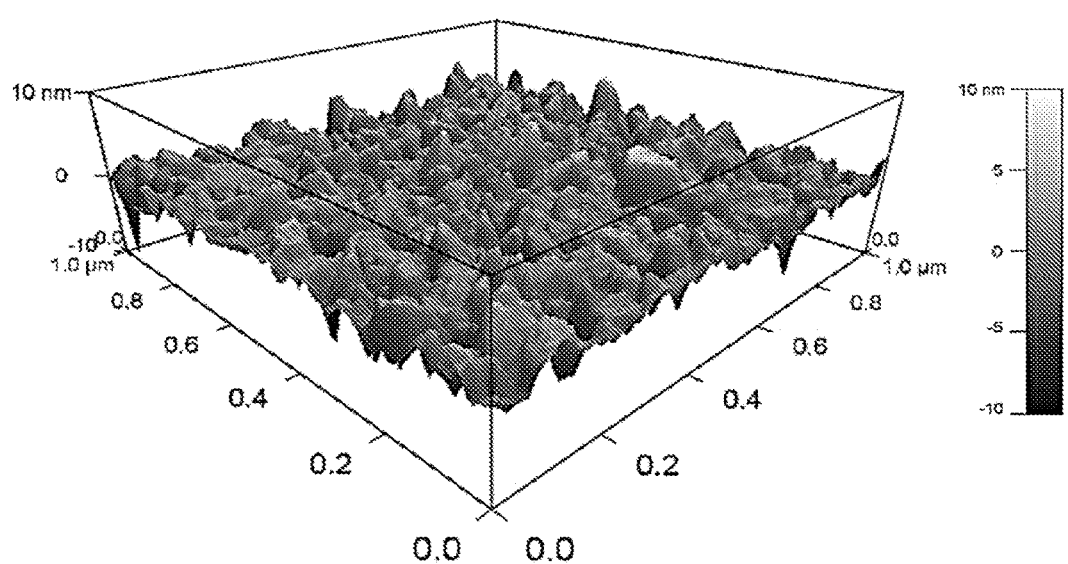
Figure 21:
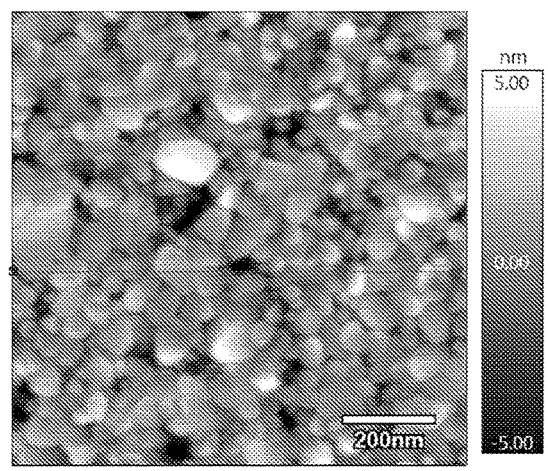
Figure 21:
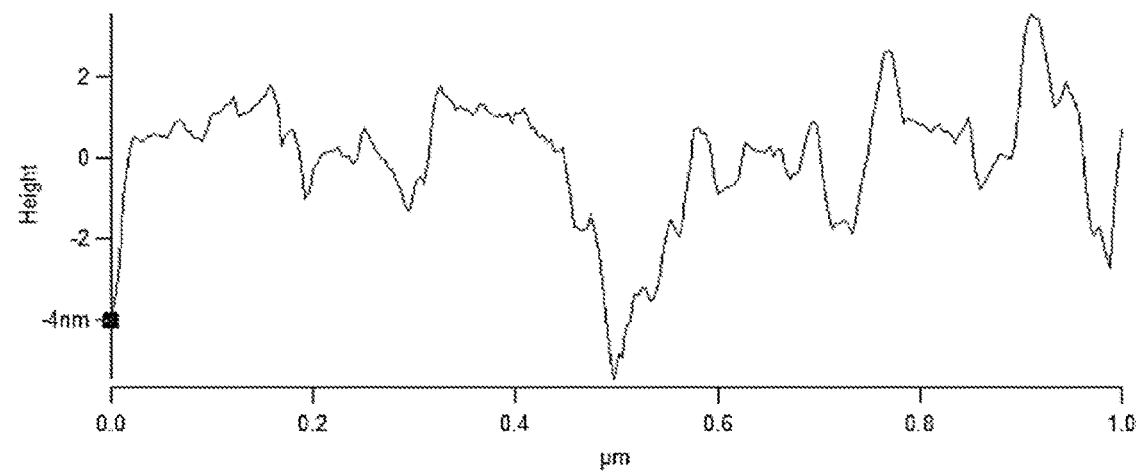
Figure 21:
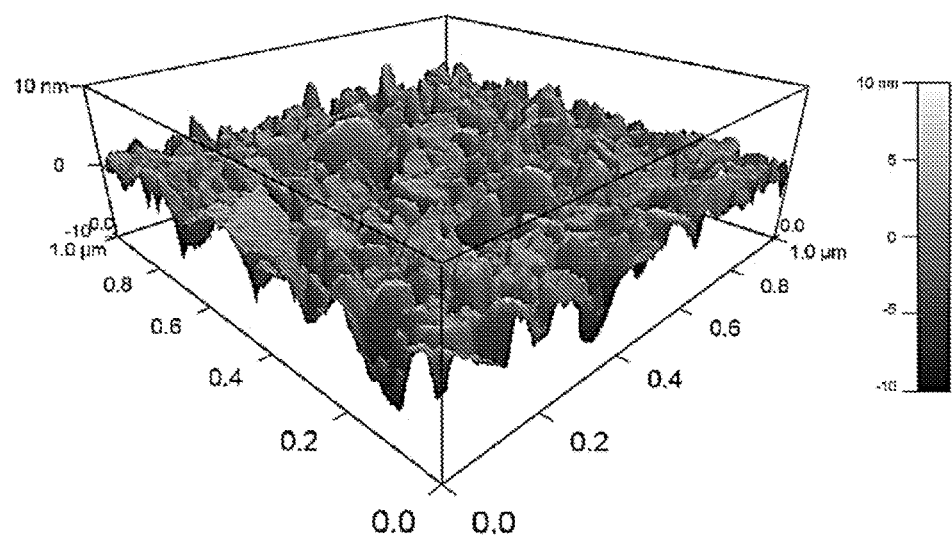
Figure 21:
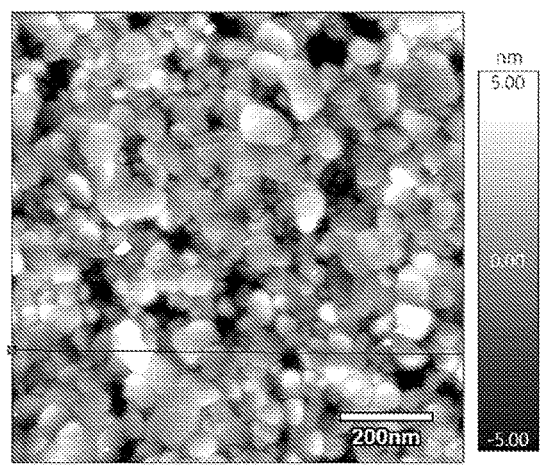
Figure 21:
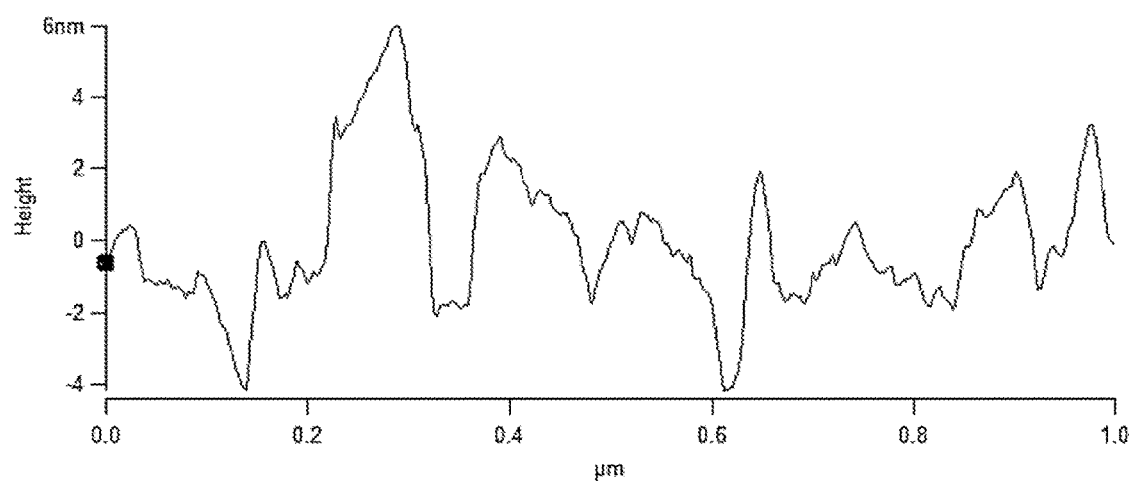
Figure 21:
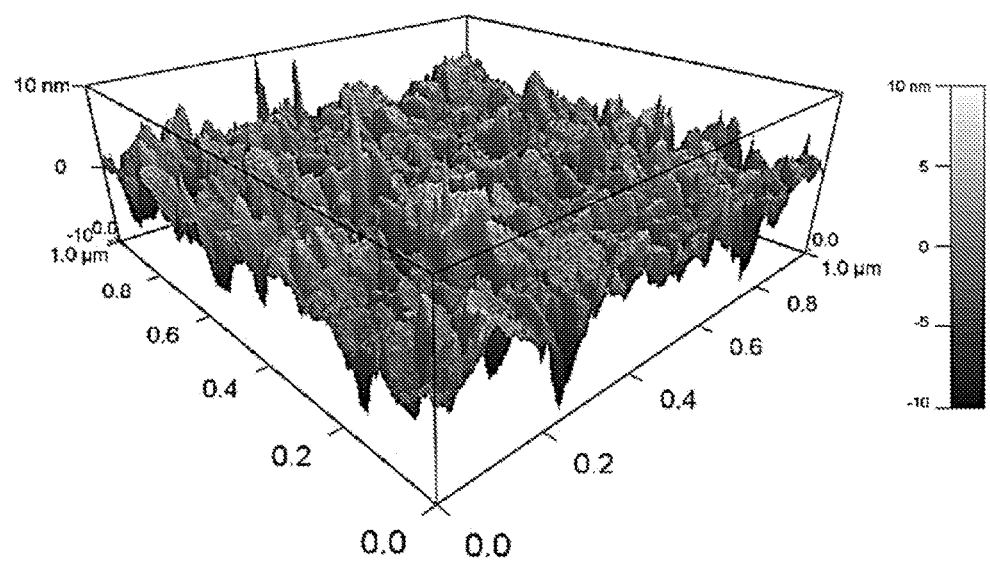
Figure 21:
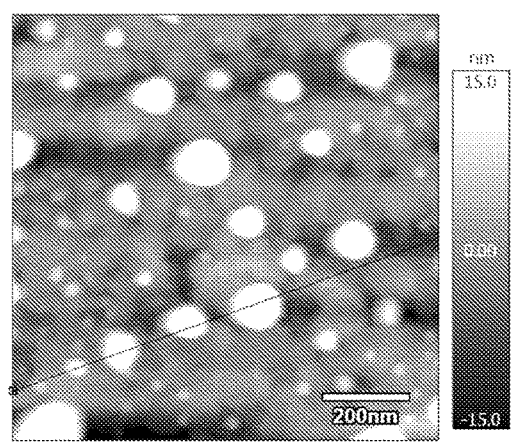
Figure 21:
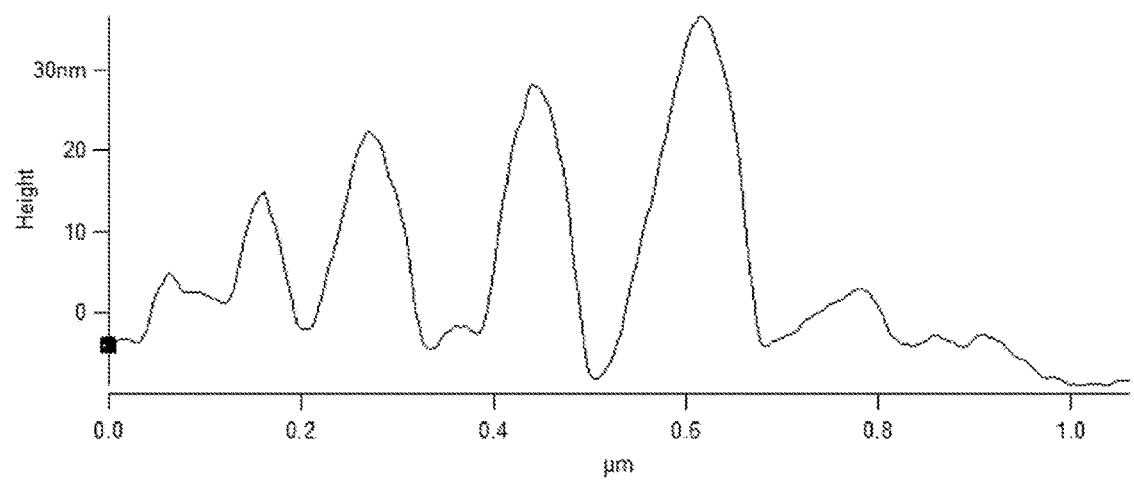
Figure 21:
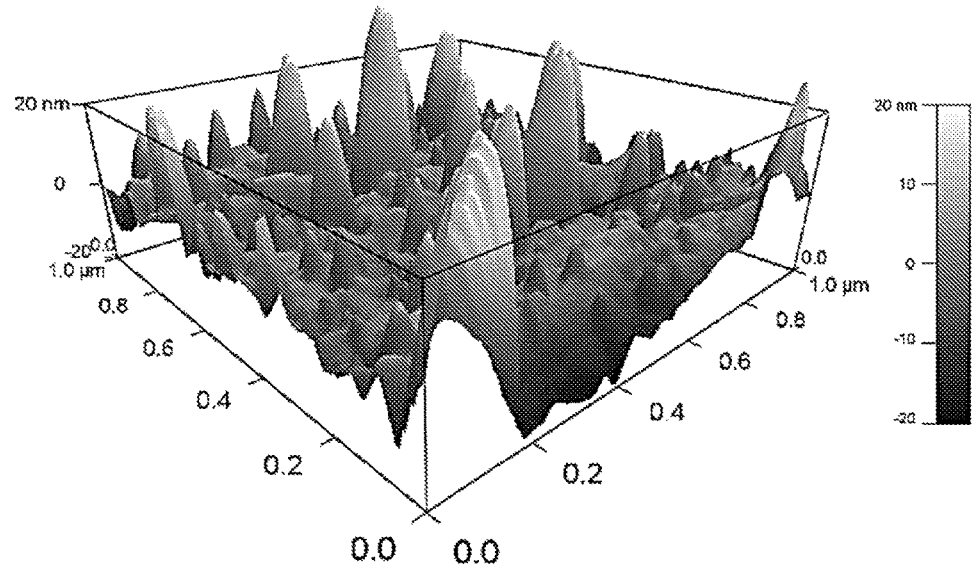

The authors used atomic force microscopy (AFM) to verify that the liposomes can be immobilised on to gold surfaces. FIG. 21 shows that a change can be seen in surface morphology and roughness profile from bare gold surface to the OR associated liposomes immobilized surface. The bare gold surface (FIG. 21(a)) shows densely packed flat gold nanocrystals of various sizes with surface roughness value of around 2 nm. After SAM modification (FIG. 21(b)) and NHS/EDC activation of SAM modified gold surface (FIG. 21(c)), negligible changes in surface morphology were observed. When OR associated liposomes were introduced to the EDC/NHS activated SAM modified gold surface (FIG. 21(d)), the change in surface morphology was noticeable showing circular shaped liposomes immobilised on the surface. Variable sized round shaped liposomes were seen all over the surface in their native form i.e. no rupture or bilayer formation was observed which also indicates ORs are well retained in the membranes of liposomes. The large increase in surface roughness values (>30 nm) also demonstrates that ORs containing liposomes were successfully attached to the NHS/EDC activated SAM modified gold surface.

Figure 22:
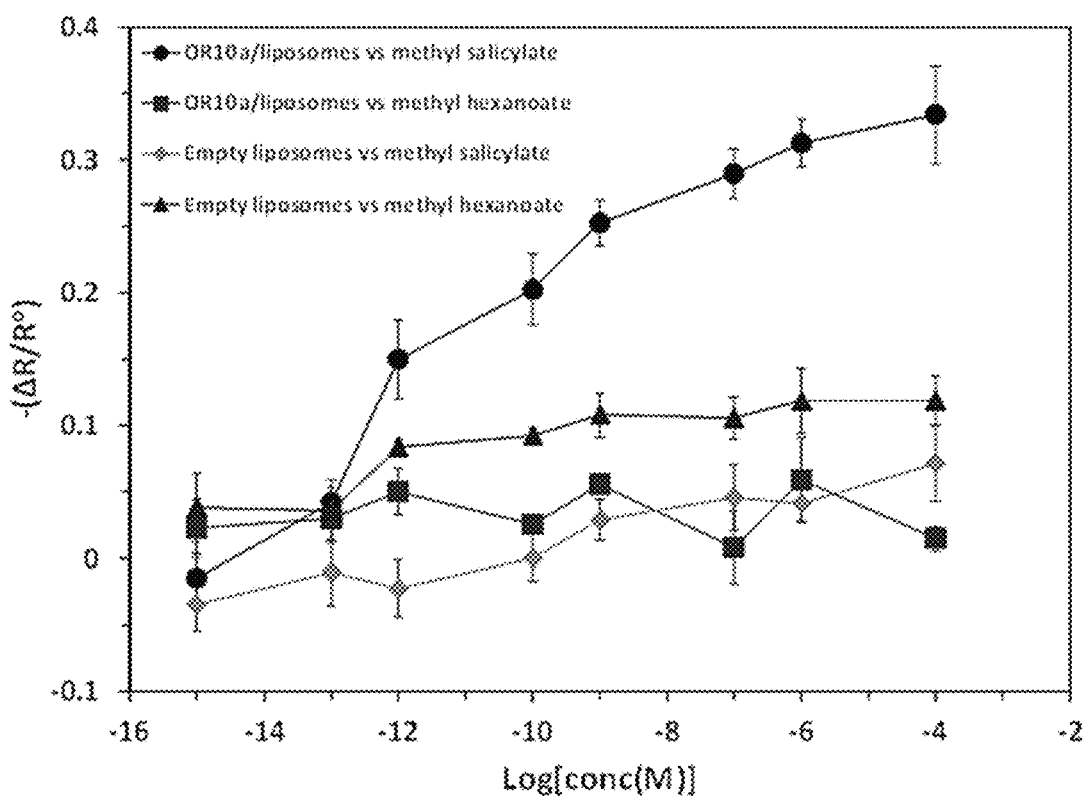
FIG. 22 shows dose response curves for gold electrodes functionalized with A) Or10a liposomes in response to the target ligand Methyl salicylate, and control ligand methyl hexanoate; C) Or22a liposomes in response to the target ligand Methyl hexanoate and control ligand Methyl salicylate; and D) Or71a liposomes in response to the target ligand 4-ethy guaiacol and control ligand E2 Hexenal. In each example target and control ligand binding measurements were also performed with gold electrodes functionalised with empty liposomes.
Figure 22:
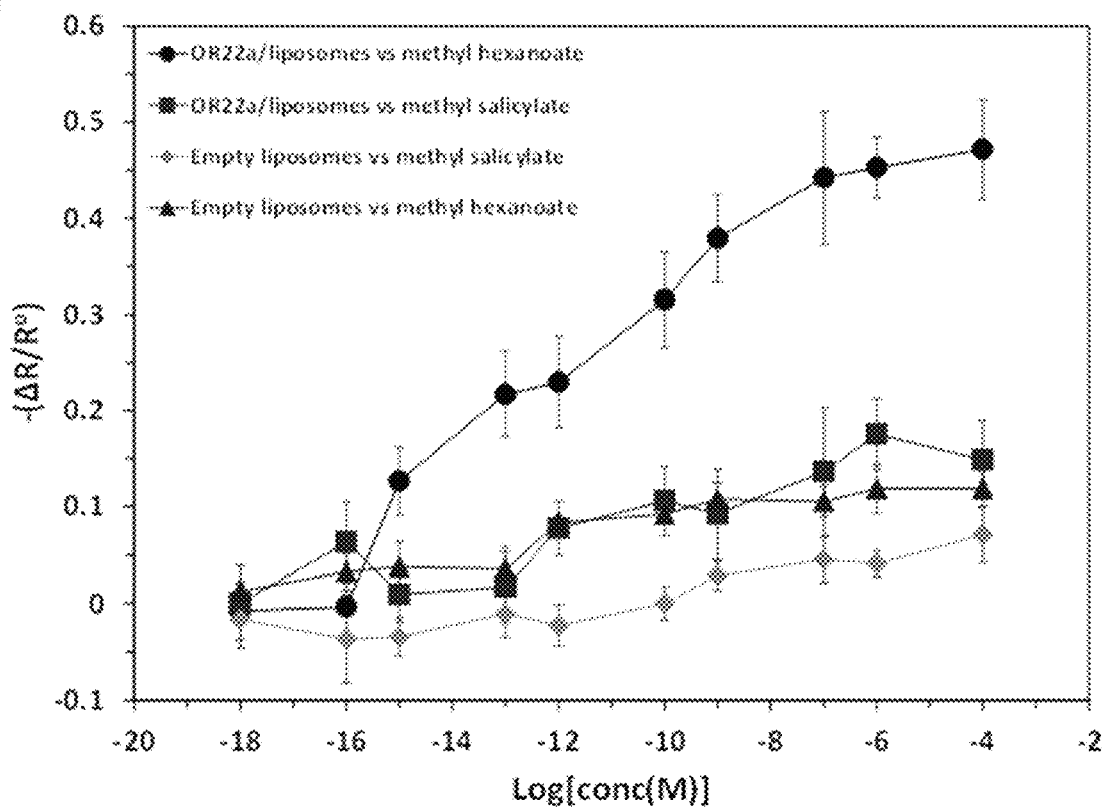
Figure 22:
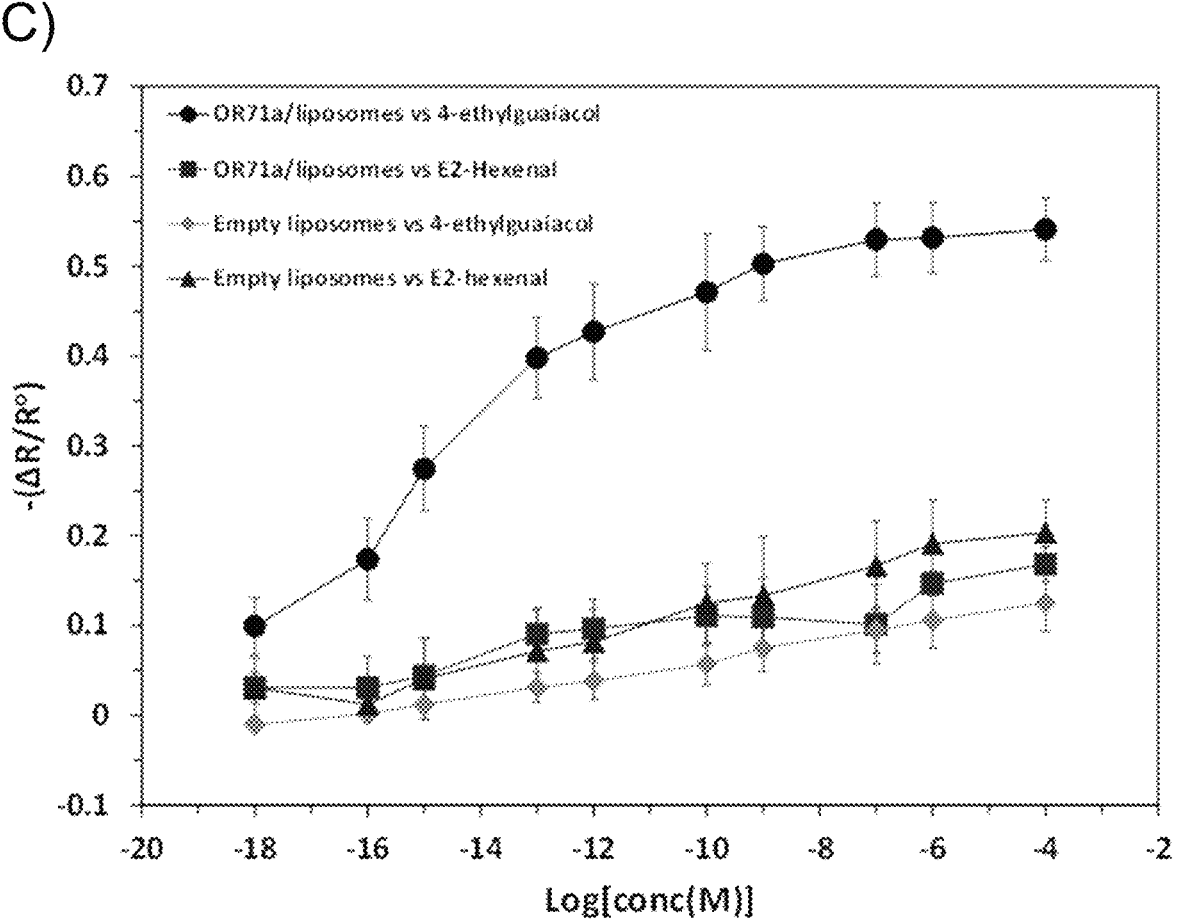

EIS measurements were performed and analysed as described in Example 1 Section 2.0. EIS measurements were performed on gold electrodes functionalised with OrX associated liposomes (either Or10a, Or22a or Or71a), or empty liposomes prior to and after target ligand or control ligand incubation with increasing concentrations. Calibration curves were obtained by defining sensor response as $\Delta R_{ct}/R^0_{ct}$ versus log[C(Ligand)] (FIGS. 22(a) to (c)). FIG. 22(a) shows that Or10a liposomes respond sensitively (LOD of 1 pM) and selectively to methyl salicylate, and as expected do not respond to the control ligand methyl hexanoate. FIG. 22(b) shows that Or22a liposomes respond sensitively (LOD of 10 fM) and selectively to methyl hexanoate, and as expected do not respond to the control ligand methyl salicylate. FIG. 22(c) shows that Or71a liposomes respond sensitively (LOD of 0.1 fM) and selectively to 4-ethyl guaiacol, and do not respond to the control ligand methyl salicylate. In each of the figures, empty nanodiscs do not respond to any of the target ligands demonstrating that the presence of each OrX is the key to the detection of each target ligand.

4. Conclusion

This study has further demonstrated the recognition ability of OrXs and promising olfactory biosensor application based on electronic device platforms. OrXs embedded in liposomes which are functionalized on the gold electrodes show extremely sensitive electrochemical impedance responses down to fM concentrations of target ligands, and exhibit a dynamic range over 8 orders of magnitude. Compared with results from empty nanodiscs functionalized electrodes, no clear impedance response to target ligands are observed. The specific binding of each OrX has also been verified by testing the response to control ligands from the OrX liposome functionalized electrodes. The OrX liposomes functionalized electrodes have shown great promise to specifically and sensitively detect their target ligands.

Example 6

Exemplification of the Sensor of the Invention with Quartz Crystal Microbalance (QCM) Piezoelectric Transducer Summary The applicants have produced a convenient piezoelectric sensor device using the *Drosophila melanogaster* Or22a[43, 63] sequence embedded in liposomes. Quartz Crystal microbalance with Dissipation monitoring (QCM-D) is a mass sensitive piezoelectric transducer, whose oscillation frequency changes with the mass loading on the crystal. The interaction between Or22a and the target ligand methyl hexanoate was detected by monitoring the oscillation frequency changes of QCM-D sensor with Or22a liposomes coupled to it. The specificity of the binding was verified by testing the response of empty liposomes coupled to the QCM-D sensor to the target ligand tested.

1. Experimental Methods 2.1 Materials 6-mercaptohexanoic acid (MHA), N-hydroxysuccinimide (NHS), 1-ethyl-3-(3-dimethylaminopropyl)-carbodiimide) (EDC), phosphate buffer saline (PBS) tablets, and methyl hexanoate were obtained from Sigma-Aldrich. Gold (100 nm) sensor crystals (QSX301) were obtained from ATA Scientific Instruments.

2.2 Preparation of OR Associated Liposomes 2.2.1 Preparation of Purified OR Subunits OR subunits were prepared as described in Example 3 section 2.2.1

2.2.2 Preparation of OR Associated Liposomes

OR22a liposomes were prepared as described in Example 1 section 1.2.

2.3 Quartz Crystal Microbalance (QCM) Preparation and Data Collection

Gold (100 nm) sensor crystals were sonicated in ethanol and milli-Q water for 15 minutes each respectively. A 5:1:1 volume ratio of milli-Q water, ammonia (25%), and hydrogen peroxide (30%) was heated to 75° C. for 5 minutes and the sonicated crystals were placed in the heated solution for 5 minutes. Then the crystals were removed from the solution and rinsed with milli-Q water before drying with nitrogen gas. The clean gold crystals were thiol-functionalized by exposing them to 2 mM ethanolic solution of MHA overnight followed by washing with ethanol solution in order to remove excess or loosely bound molecules. The SAM functionalized crystals were then placed into the Q-sense analyser instrument (Biolin Scientific) chamber and flowed with the NHS/EDC, OR22a/liposomes and various concentrations of methyl hexanoate (1.6 μM, 8 μM, 40 μM, 200 μM and 1 mM) in PBS buffer solution to measure the changes in frequency (Δf) and dissipation (ΔD) values.

3.0 Results

Figure 23:
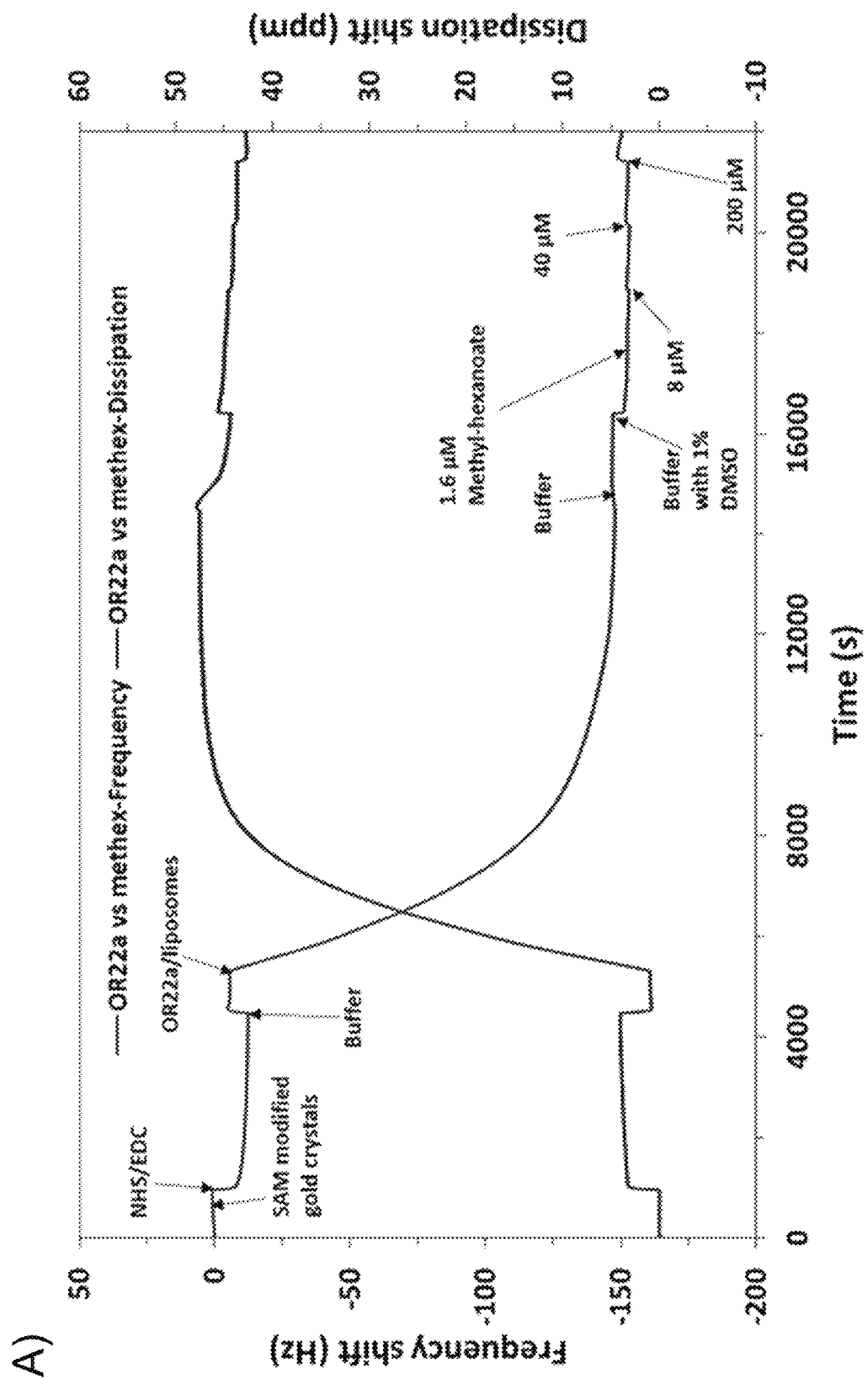
FIG. 23 (A) shows the change in frequency and dissipation on the Quartz crystal microbalance with Dissipation monitoring (QCM-D) with SAM and NHS/EDC modification, Or22a liposome immobilisation followed by binding of the target ligand methyl hexanoate. (B) Shows a close up view of the change in frequency and dissipation with increasing concentrations of methyl hexanoate (buffer only, 1.6, 8, 40 and 200 μM) for the Or22a liposome immobilised QCM-D sensor. (C) Shows the change in frequency and dissipation on the QCM-D sensor with SAM and NHS/EDC modification, empty liposome immobilisation followed by binding of the target ligand methyl hexanoate. (D) Shows a close up view of the change in frequency and dissipation with increasing concentrations of methyl hexanoate (buffer only, 1.6, 8, 40 and 200 μM) for the empty liposome immobilised QCM-D sensor.
Figure 23:
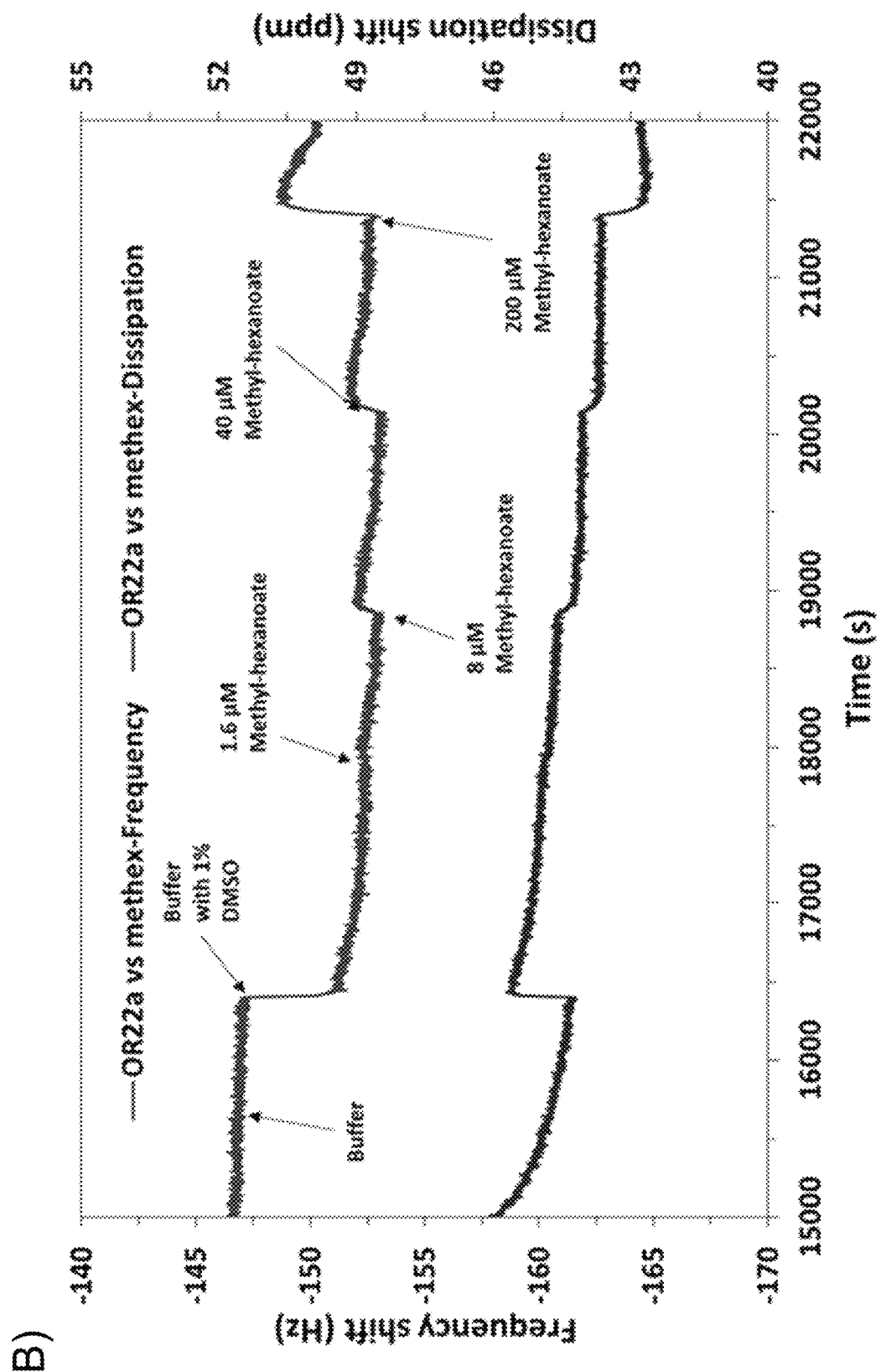
Figure 23:
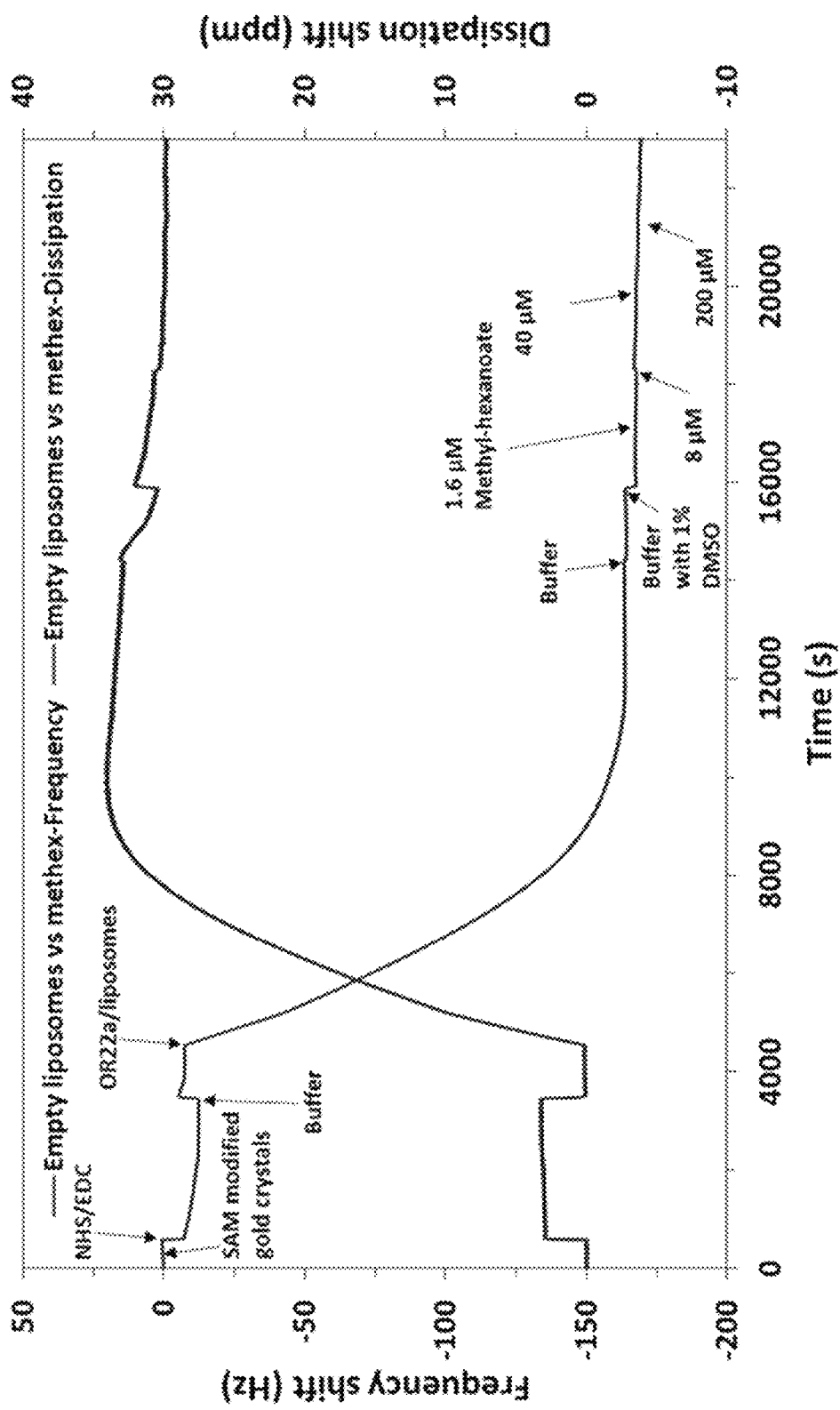
Figure 23:
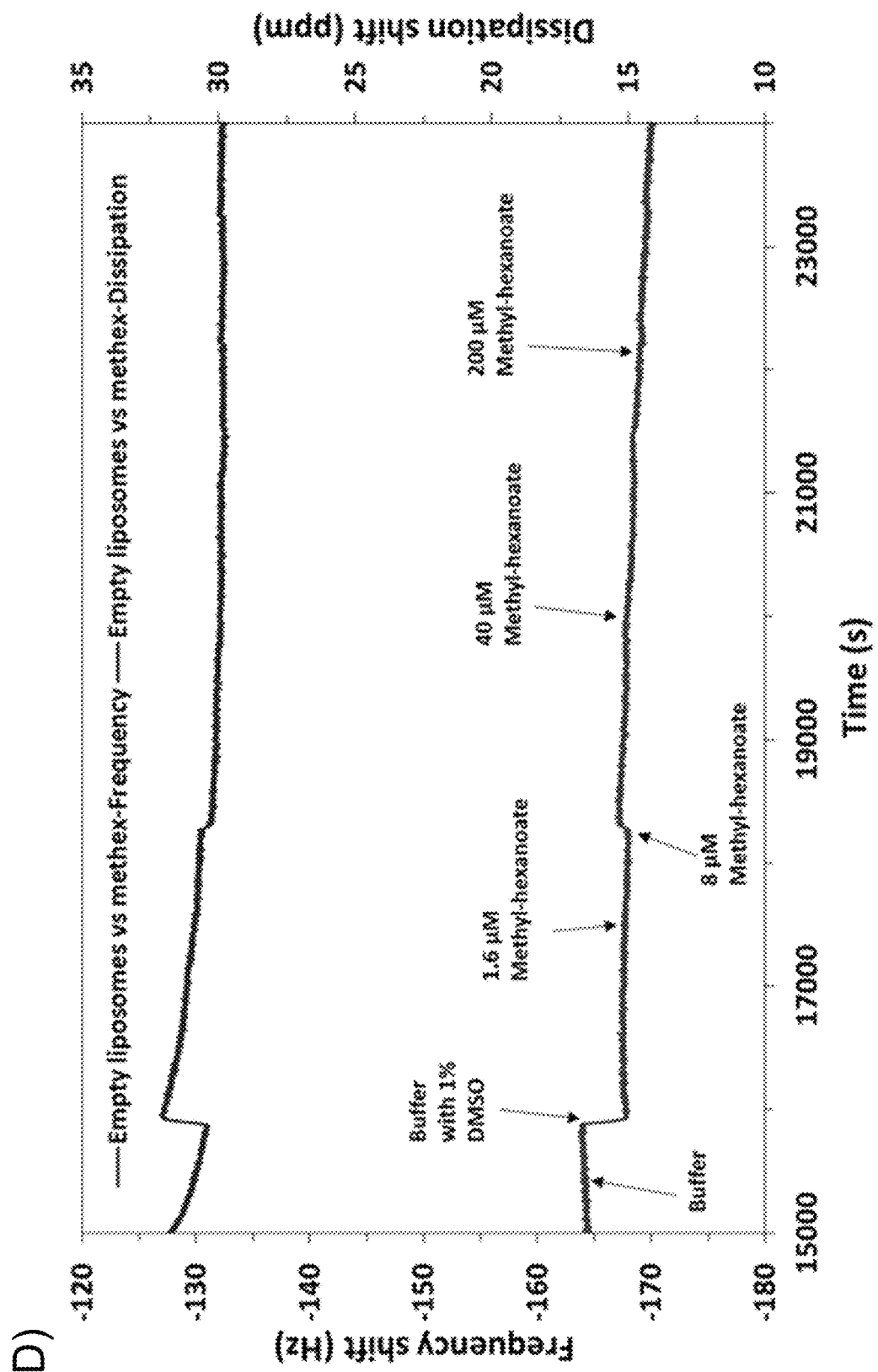

FIG. 23(a) shows the change in frequency and dissipation upon the SAM and NHS/EDC modification, followed by Or22a liposome immobilisation on the quartz crystal and then binding of the target ligand methyl hexanoate. When a binding event occurs on the crystal this results in an increase in the mass reducing the frequency of oscillation[64]. Thus the mass of the sensor increases with SAM, NHS/EDC, and Or22a liposome immobilisation. However, in the case of methyl hexanoate binding an increase in the frequency is observed (FIG. 23(b)). Without wishing to be bound by theory, the inventors suggest this loss of mass on the sensor is due to the binding of methyl hexanoate to the Or22a receptor causing a release of water and ions from inside the Or22a liposomes i.e. the Or22a is forming a functional ion channel. This increase in frequency occurs with increasing concentrations of methyl hexanoate between 1.6 to 200 μM indicating that methyl hexanoate is binding specifically to the Or22a receptor, as this increase in frequency is not observed with empty liposomes immobilised on the QCM (FIGS. 23(c) & (d)). Detection of ligand binding at the μM level equivalent to parts-per-trillion (ppt) concentration is on par with what has been seen with *C. elegans* ODR-10[65].

4. Conclusion

This study has further demonstrated the recognition ability of OrXs and promising olfactory biosensor application based on electronic device platforms. OrXs in liposomes which are functionalized on quartz crystal microbalance (QCM) piezoelectric sensors can specifically detect their target ligand. Compared with results from empty liposomes functionalized on the QCM, for which no clear piezoelectric response to the target ligands was observed. OrX liposomes functionalized QCMs show great promise to specifically and sensitively detect their target ligands.

REFERENCES

1. Montagne N, de Fouchier A, Newcomb R D, Jacquin-Joly E (2015) Advances in the identification and characterization of olfactory receptors in insects. Progress in molecular biology and translational science 130: 55-80. doi: 10.1016/bs.pmbts.2014.11.003.
2. Leary G P, Allen J E, Bunger P L, Luginbill J B, Linn C E, Jr., Macallister I E, Kavanaugh M P, Wanner K W (2012) Single mutation to a sex pheromone receptor provides adaptive specificity between closely related moth species. Proc Natl Acad Sci 109: 14081-6.
3. Kiely A, Authier A, Kralicek A V, Warr C G, Newcomb R D (2007) Functional analysis of a *Drosophila melanogaster* olfactory receptor expressed in Sf9 cells. J. Neurosci. Methods 159: 189-94. doi: S0165-0270(06)00321-9 [pii]. 10.1016/j.jneumeth.2006.07.005.
4. Claudianos C, Lim J, Young M, Yan S Z, Cristino A S, Newcomb R D, Gunasekaran N, Reinhard J (2014) Odor memories regulate olfactory receptor expression in the sensory periphery. Eur. J. Neurosci. 39: 1642-1654. doi: Doi 10.1111/Ejn.12539.
5. Jones P L, Pask G M, Rinker D C, Zwiebel L J (2011) Functional agonism of insect odorant receptor ion channels. Proc. Natl. Acad. Sci. USA 108: 8821-5.
6. WO2000US4995—Genes encoding insect odorant receptors and uses thereof.
7. WO2002US5414—Chemosensory gene family encoding gustatory and olfactory receptors and uses thereof.
8. WO2004US42372—In vivo odorant receptor systems and their uses.
9. WO2000US1823—Novel odorant receptors in *Drosophila*.
10. WO2002US9559—Efficient methods for isolating functional G-protein coupled receptors and identifying active effectors and efficient methods to isolate proteins involved in olfaction and efficient methods to isolate and identifying active effectors.
11. WO2012US34847—Composition for inhibition of insect sensing.
12. Misawa N, Mitsuno H, Kanzaki R, Takeuchi S (2010) Highly sensitive and selective odorant sensor using living cells expressing insect olfactory receptors. *Proc. Natl. Acad. Sci. U.S.A.* 107: 15340-4. doi: 10.1073/pnas.1004334107.
13. Mitsuno H, Sakurai T, Namiki S, Mitsuhashi H, Kanzaki R (2015) Novel cell-based odorant sensor elements based on insect odorant receptors. *Biosens. Bioelectron.* 65: 287-294. doi: DOI 10.1016/j.bios.2014.10.026.
14. Carraher C, Nazmi A R, Newcomb R D, Kralicek A 2013. Recombinant expression, detergent solubilisation and purification of insect odorant receptor subunits. Protein Expr Purif 90(2): 160-169.
15. Smart R, Kiely A, Beale M, Vargas E, Carraher C, Kralicek A V, Christie D L, Chen C, Newcomb R D, Warr C G. 2008. *Drosophila* odorant receptors are novel seven transmembrane domain proteins that can signal independently of heterotrimeric G proteins. Insect Biochem Mol Biol. 2008, 38(8):770-80.
16. Hopf T A, Morinaga S, Ihara S, Touhara K, Marks D S, Benton R. Amino acid coevolution reveals three-dimensional structure and functional domains of insect odorant receptors. Nat Commun. 2015, 13; 6:6077.
17. Jordan M D, Anderson A, Begum D, Carraher C, Authier A, Marshall S D, Kiely A, Gatehouse L N, Greenwood D R, Christie D L and others 2009. Odorant receptors from the light brown apple moth (*Epiphyas postvittana*) recognize important volatile compounds produced by plants. Chemical Senses 34(5): 383-394.
18. Anderson A R, Wanner K W, Trowell S C, Warr C G, Jaquin-Joly E, Zagatti P, Robertson H, Newcomb R D 2009. Molecular basis of female-specific odorant responses in *Bombyx mori*. Insect Biochemistry and Molecular Biology 39(3): 189-197.
19. Corcoran J A, Jordan M D, Carraher C, Newcomb R D 2014. A novel method to study insect olfactory receptor function using HEK293 cells. Insect Biochem Mol Biol.
20. Forstner M, Breer H, Krieger J 2009. A receptor and binding protein interplay in the detection of a distinct pheromone component in the silkmoth *Antheraea polyphemus*. International Journal of Biological Sciences 5(7): 745-757.
21. Grosse-Wilde E, Gohl T, Bouche E, Breer H, Krieger J 2007. Candidate pheromone receptors provide the basis for the response of distinct antennal neurons to pheromonal compounds. European Journal of Neuroscience 25(8): 2364-2373.
22. Grosse-Wilde E, Svatos A, Krieger J 2006. A pheromone-binding protein mediates the bombykol-induced activation of a pheromone receptor in vitro. Chemical Senses 31(6): 547-555.
23. Kumar B N, Taylor R W, Pask G M, Zwiebel L J, Newcomb R D, Christie D L 2013. A conserved aspartic acid is important for agonist (VUAA1) and odorant/tuning receptor-dependent activation of the insect odorant co-receptor (Orco). PLoS One 8(7): e70218.
24. Turner R M, Derryberry S L, Kumar B N, Brittain T, Zwiebel L J, Newcomb R D, Christie D L 2014. Mutational analysis of cysteine residues of the insect odorant co-receptor (Orco) from *Drosophila melanogaster* reveals differential effects on agonist- and odorant-tuning receptor-dependent activation. Journal of Biological Chemistry 289(46): 31837-31845.
25. Pask G M, Romaine I M, Zwiebel L J 2013. The molecular receptive range of a lactone receptor in *Anopheles gambiae*. Chemical Senses 38(1): 19-25.
26. Liu C C, Liu Y, Walker W B, Dong S L, Wang G R 2013. Identification and functional characterization of sex pheromone receptors in beet armyworm *Spodoptera exigua* (Hubner). Insect Biochemistry and Molecular Biology 43(8): 747-754.
27. Miura N, Nakagawa T, Tatsuki S, Touhara K, Ishikawa Y 2009. A male-specific odorant receptor conserved through the evolution of sex pheromones in *Ostrinia* moth species. International Journal of Biological Sciences 5(4): 319-330.
28. Mitsuno H, Sakurai T, Murai M, Yasuda T, Kugimiya S, Ozawa R, Toyohara H, Takabayashi J, Miyoshi H, Nishioka T 2008. Identification of receptors of main sex-pheromone components of three Lepidopteran species. European Journal of Neuroscience 28(5): 893-902.
29. Sakurai T, Nakagawa T, Mitsuno H, Mori H, Endo Y, Tanoue S, Yasukochi Y, Touhara K, Nishioka T 2004. Identification and functional characterization of a sex pheromone receptor in the silkmoth *Bombyx mori*. Proceedings of the National Academy of Sciences of the United States of America 101(47): 16653-16658.
30. Xu P X, Garczynski S F, Atungulu E, Syed Z, Choo Y M, Vidal D M, Zitelli C H L, Leal W S 2012. Moth Sex Pheromone Receptors and Deceitful Parapheromones. Plos One 7(7).
31. Wang G, Vasquez G M, Schal C, Zwiebel L J, Gould F 2011. Functional characterization of pheromone receptors in the tobacco budworm *Heliothis virescens*. Insect Molecular Biology 20(1): 125-133.
32. Wanner K W, Nichols A S, Allen J E, Bunger P L, Garczynski S F, Linn C E, Robertson H M, Luetje C W 2010. Sex Pheromone Receptor Specificity in the European Corn Borer Moth, *Ostrinia nubilalis*. Plos One 5(1).
33. Wang G R, Carey A F, Carlson J R, Zwiebel L J 2010. Molecular basis of odor coding in the malaria vector mosquito *Anopheles gambiae*. Proc Natl. Acad. Sci. USA 107(9): 4418-4423.
34. Geertsma, E. R., et al., *Membrane reconstitution of ABC transporters and assays of translocator function*. Nature Protocols, 2008. 3(2): p. 256-266.
35. Booth, M. A., S. Harbison, and J. Travas-Sejdic, *Development of an electrochemical polypyrrole-based DNA sensor and subsequent studies on the effects of probe and target length on performance*. Biosensors and Bioelectronics, 2011. 28(1): p. 362-367.
36. Booth, M. A., S. Harbison, and J. Travas-Sejdic, *Effects of Redox Couple on the Response of Polypyrrole-Based Electrochemical DNA Sensors*. Electroanalysis, 2012. 24(6): p. 1311-1317.
37. Zhu, B., et al., *Distinguishing cytosine methylation using electrochemical, label-free detection of DNA hybridization and ds-targets*. Biosensors and Bioelectronics, 2015. 64: p. 74-80.
38. Zhu, B., et al., *Label-free electrochemical aptasensor for femtomolar detection of 17β-estradiol*. Biosensors and Bioelectronics, 2015. 70: p. 398-403.
39. Lu, Y., et al., *Olfactory biosensor using odorant-binding proteins from honeybee: Ligands of floral odors and pheromones detection by electrochemical impedance*. Sensors and Actuators B: Chemical, 2014. 193: p. 420-427.
40. Sankaran, S., S. Panigrahi, and S. Mallik, *Odorant binding protein based biomimetic sensors for detection of alcohols associated with Salmonella contamination in packaged beef*. Biosensors and Bioelectronics, 2011. 26(7): p. 3103-3109.
41. Kuang, Z., et al., *Biomimetic Chemosensor: Designing Peptide Recognition Elements for Surface Functionalization of Carbon Nanotube Field Effect Transistors*. ACS Nano, 2010. 4(1): p. 452-458.
42. Kannan, B., et al., *High-Sensitivity, Label-Free DNA Sensors Using Electrochemically Active Conducting Polymers*. Analytical Chemistry, 2011. 83(9): p. 3415-3421.
43. Robertson H M, Warr C G, Carlson J R 2003. Molecular evolution of the insect chemoreceptor gene superfamily in *Drosophila melanogaster*. Proceedings of the National Academy of Sciences of the United States of America 100: 14537-14542.
44. Hallem E A, Carlson J R 2006. Coding of odors by a receptor repertoire. Cell 125(1): 143-160.
45. Silbering A F, Rytz R, Grosjean Y, Abuin L, Ramdya P, Jefferis G S, Benton R 2011. Complementary function and integrated wiring of the evolutionarily distinct *Drosophila* olfactory subsystems. Journal of Neuroscience 31(38): 13357-13375.
46. Boyle S M, Mclnally S, Ray A 2013. Expanding the olfactory code by in silico decoding of odor-receptor chemical space. Elife 2: e01120.
47. Hill C A, Fox A N, Pitts R J, Kent L B, Tan P L, Chrystal M A, Cravchik A, Collins F H, Robertson H M, Zwiebel L J 2002. G protein-coupled receptors in *Anopheles gambiae*. Science 298(5591): 176-178.
48. Carey A F, Wang G R, Su C Y, Zwiebel L J, Carlson J R 2010. Odorant reception in the malaria mosquito *Anopheles gambiae*. Nature 464(7285): 66-U77.
49. Wang G R, Carey A F, Carlson J R, Zwiebel L J 2010. Molecular basis of odor coding in the malaria vector mosquito *Anopheles gambiae*. Proc Natl. Acad. Sci. USA 107(9): 4418-4423.
50. Matsubara Y, Murakami Y, Kobayashi M, Morita Y, Tamiya E 2004. Application of on-chip cell cultures for the detection of allergic response. Biosensors and Bioelectronics 19(7): 741-747.
51. Figueroa X A, Cooksey G A, Votaw S V, Horowitz L F, Folch A 2010. Large-scale investigation of the olfactory receptor space using a microfluidic microwell array. Lab Chip 10(9): 1120-1127.
52. Hossein-Babaei F, Paknahad M, Ghafarinia V 2012. A miniature gas analyzer made by integrating a chemoresistor with a microchannel. Lab Chip 12(10): 1874-1880.
53. Hossein-Babaei F, Ghafarinia V 2010. Gas analysis by monitoring molecular diffusion in a microfluidic channel. Analytical Chemistry 82(19): 8349-8355.
54. Lee S H, Lim J H, Park J, Hong S, Park T H 2015. Bioelectronic nose combined with a microfluidic system for the detection of gaseous trimethylamine. Biosensors and Bioelectronics 71: 179-185.
55. Bayburt, T. H. & Sligar, S. G. Membrane protein assembly into Nanodiscs. *FEBS Lett.* 584, 1721-1727 (2010).
56. Bayburt, T. H. & Sligar, S. G. Self-assembly of single integral membrane proteins into soluble nanoscale phospholipid bilayers. *Protein Sci.* 12, 2476-2481 (2003).
57. Stern, E. et al. Importance of the debye screening length on nanowire field effect transistor sensors. *Nano Lett.* 7, 3405-3409 (2007).
58. Zheng, H. Y., A. Alsager, O., S. Wood, C., M. Hodgkiss, J. & O. V. Plank, N. Carbon nanotube field effect transistor aptasensors for estrogen detection in liquids. *J. Vac. Sci. Technol. B* 33, 06F904 (2015).
59. O. V. Plank, N., Ishida, M. & Cheung, R. Positioning of carbon nanotubes using soft-lithography for electronics applications. *J. Vac. Sci. Technol. B Microelectron. Nanom. Struct.* 23, 3178-3181 (2005).
60. Goldsmith, B. R. et al. Biomimetic chemical sensors using nanoelectronic readout of olfactory receptor proteins. *ACS Nano* 5, 5408-16 (2011).
61. Zheng, H. Y. et al. Electrostatic gating in carbon nanotube aptasensors. *Nanoscale* 8, 13659-13668 (2016).
62. Heller, I. et al. Identifying the mechanism of biosensing with carbon nanotube transistors. *Nano Lett.* 8, 591-595 (2008).
63. Dweck H K M, Ebrahim S A M, Farhan A, Hansson B S, Stensmyr M C. (2015) Olfactory proxy detection of dietary antioxidants in *drosophila*. *Curr Biol* 25:455-66.

64. Glatz R, Bailey-Hill K. (2011) Mimicking nature's noses: From receptor deorphaning to olfactory biosensing. *Prog Neurobiol* 93:270-96.

65. Du L, Chunseng W, Peng H, Zou L, Zha L, Huang L and Wang P (2013) Piezoelectric olfactory receptor biosensor prepared by aptamer-assisted immobilization. *Sensors and Actuators* 8 187: 481-487.

The invention claimed is:

1. A sensor device comprising a purified insect odorant receptor OrX subunit in electrical communication with a substrate, wherein the sensor device is configured to detect a change in an electrical characteristic of the substrate, and wherein the sensor device does not comprise an insect odorant co-receptor (Orco).

2. The sensor device of claim 1 in which the change in the electrical characteristic results from binding of an analyte to the OrX subunit.

3. The sensor device of claim 1 in which the sensor device is capable of detecting binding of an analyte to the OrX subunit by detecting the change in the electrical characteristic of the substrate.

4. The sensor device of claim 3 in which the sensor device can detect the presence of the analyte at a concentration of less than $1 \times 10^{-3}$ M.

5. The sensor device of claim 1 in which the OrX subunit is present in a form that is capable of undergoing a conformational change in response binding of an analyte.

6. The sensor device of claim 1 in which the OrX subunit is present in a membrane mimic.

7. The sensor device of claim 6 in which the membrane mimic is selected from a liposome, an amphipole, a detergent micelle, a nanovesicle, a lipid bilayer, a nanodisc, and a surfactant.

8. The sensor device of claim 1 in which the substrate is selected from, or composed of, at least one of: an electrode, a semiconductor material, carbon nanotubes (CNTs), graphene, an oxide, doped silicon, a conducting polymer, and a resonator component.

9. The sensor device of claim 1 in which the electrical characteristic is selected from at least one of: conductivity, resistance, complex resistance, impedance, electrochemical impedance, flow of current, and resonance frequency of oscillations induced by an alternating electric field.

10. A method of detecting an analyte, the method comprising the steps:
    a) binding of the analyte to the OrX subunit in the sensor device of claim 1, and
    b) detecting a change in an electrical characteristic of the substrate,
    wherein the change in the electrical characteristic of the substrate indicates detection of the analyte.

11. A method of detecting the presence of an analyte in an environment, the method comprising the steps:
    a) exposing the sensor device of claim 1 to the environment containing the analyte,
    b) binding of the analyte to the OrX subunit in the sensor device, and
    c) detecting a change in an electrical characteristic of the substrate,
    wherein the change in the electrical characteristic of the substrate indicates presence of the analyte in the environment.

12. A method of manufacturing a sensor device, the method comprising the step of establishing electrical communication between a purified insect odorant receptor OrX subunit of the sensor device and a substrate of the sensor device, wherein the sensor device is configured to detect a change in an electrical characteristic of the substrate, and wherein the sensor device does not comprise an insect odorant co-receptor (Orco).

13. A sensor device component comprising a purified insect odorant receptor OrX subunit in electrical communication with a substrate, wherein the sensor device component does not comprise an insect odorant co-receptor (Orco).

14. A sensor device comprising the sensor device component of claim 13, wherein the sensor device is configured to detect a change in an electrical characteristic of the substrate.

15. A method of assembling a sensor device, the method comprising adding the sensor device component of claim 13 to the sensor device, wherein the assembled sensor device is configured to detect a change in an electrical characteristic of the substrate.

* * * * *